United States Patent
Weaver et al.

(10) Patent No.: US 10,668,185 B2
(45) Date of Patent: Jun. 2, 2020

(54) METHODS OF MANUFACTURING INJECTABLE MICROGEL SCAFFOLDS

(71) Applicant: TEMPO THERAPEUTICS, INC., San Diego, CA (US)

(72) Inventors: Westbrook Weaver, San Diego, CA (US); Stephanie Deshayes, San Diego, CA (US); Samuel Timko, San Diego, CA (US)

(73) Assignee: TEMPO THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/457,514

(22) Filed: Jun. 28, 2019

(65) Prior Publication Data

US 2019/0321797 A1  Oct. 24, 2019

Related U.S. Application Data

(63) Continuation of application No. PCT/US2017/068243, filed on Dec. 22, 2017.
(Continued)

(51) Int. Cl.
*A61L 27/52* (2006.01)
*A61L 27/54* (2006.01)
(Continued)

(52) U.S. Cl.
CPC .............. *A61L 27/52* (2013.01); *A61L 27/14* (2013.01); *A61L 27/16* (2013.01); *A61L 27/18* (2013.01);
(Continued)

(58) Field of Classification Search
CPC ...................................................... A61L 26/00
See application file for complete search history.

(56) References Cited

U.S. PATENT DOCUMENTS

| 4,726,877 A | 2/1988 | Fryd et al. |
|---|---|---|
| 4,753,865 A | 6/1988 | Fryd et al. |

(Continued)

FOREIGN PATENT DOCUMENTS

| EP | 1041970 A1 | 10/2000 |
|---|---|---|
| EP | 1063975 A1 | 1/2001 |

(Continued)

OTHER PUBLICATIONS

Alijotas-Reig et al.: Late-Onset Inflammatory Adverse Reactions Related to Soft Tissue Filler Injections. Clin. Rev. Allergy Immunol. 45:97-108 (Aug. 2013).
(Continued)

*Primary Examiner* — Yashita Sharma
(74) *Attorney, Agent, or Firm* — Wilson Sonsini Goodrich & Rosati

(57) ABSTRACT

Disclosed herein are methods of manufacturing injectable microgel scaffolds, including methods of producing, purifying and concentrating microgel particles therein. The microgel scaffolds of the present disclosure are useful for a wide range of applications, such as stabilizing an implanted medical device in an implant site in a subject. The microgel scaffolds are fluidic during application and annealed or crosslinked after application to the implant site in the subject. The microgel scaffolds may contain various therapeutic agents, including antibiotics and analgesics, throughout the gel.

20 Claims, 12 Drawing Sheets

Related U.S. Application Data

(60) Provisional application No. 62/440,370, filed on Dec. 29, 2016.

(51) Int. Cl.
*A61L 27/56* (2006.01)
*A61L 27/16* (2006.01)
*A61L 27/18* (2006.01)
*A61L 27/14* (2006.01)
*B01J 13/00* (2006.01)
*B01J 19/00* (2006.01)
*A61L 27/58* (2006.01)

(52) U.S. Cl.
CPC .............. *A61L 27/54* (2013.01); *A61L 27/56* (2013.01); *B01J 13/0065* (2013.01); *B01J 13/0069* (2013.01); *B01J 19/0093* (2013.01); *A61L 27/58* (2013.01); *A61L 2300/802* (2013.01); *A61L 2400/06* (2013.01); *A61L 2400/12* (2013.01); *A61L 2430/30* (2013.01)

(56) References Cited

U.S. PATENT DOCUMENTS

| | | |
|---|---|---|
| 5,102,597 A | 4/1992 | Roe et al. |
| 5,124,188 A | 6/1992 | Roe et al. |
| 5,213,580 A | 5/1993 | Slepian et al. |
| 5,575,815 A | 11/1996 | Slepian et al. |
| 5,843,156 A | 12/1998 | Slepian et al. |
| 5,854,382 A | 12/1998 | Loomis |
| 6,005,020 A | 12/1999 | Loomis |
| 6,007,833 A | 12/1999 | Chudzik et al. |
| 6,028,164 A | 2/2000 | Loomis |
| 6,063,061 A | 5/2000 | Wallace et al. |
| 6,066,325 A | 5/2000 | Wallace et al. |
| 6,156,345 A | 12/2000 | Chudzik et al. |
| 6,290,729 B1 | 9/2001 | Slepian et al. |
| 6,316,522 B1 | 11/2001 | Loomis et al. |
| 6,403,758 B1 | 6/2002 | Loomis |
| 6,495,127 B1 | 12/2002 | Wallace et al. |
| 6,534,560 B2 | 3/2003 | Loomis et al. |
| 6,602,975 B2 | 8/2003 | Hubbell et al. |
| 6,660,827 B2 | 12/2003 | Loomis et al. |
| 6,669,827 B2 | 12/2003 | Austin |
| 6,924,370 B2 | 8/2005 | Chudzik et al. |
| 6,946,499 B2 | 9/2005 | Loomis et al. |
| 7,094,418 B2 | 8/2006 | Chudzik et al. |
| 7,109,255 B2 | 9/2006 | Loomis et al. |
| 7,442,384 B2 | 10/2008 | Loomis et al. |
| 7,547,445 B2 | 6/2009 | Chudzik et al. |
| 7,615,373 B2 | 11/2009 | Simpson et al. |
| 7,776,063 B2 | 8/2010 | Sawhney et al. |
| 7,785,617 B2 | 8/2010 | Shakesheff et al. |
| 7,964,217 B2 | 6/2011 | Harris |
| 8,318,193 B2 | 11/2012 | Ratner et al. |
| 8,357,378 B2 | 1/2013 | Wallace et al. |
| 8,557,288 B2 | 10/2013 | Elbert et al. |
| 8,603,511 B2 | 12/2013 | Wallace et al. |
| 8,927,022 B2 | 1/2015 | Maginness et al. |
| 9,234,171 B2 | 1/2016 | Lee et al. |
| 2002/0091229 A1 | 7/2002 | Hubbell et al. |
| 2002/0176880 A1 | 11/2002 | Cruise et al. |
| 2004/0078004 A1 | 4/2004 | Bourne et al. |
| 2005/0119762 A1 | 6/2005 | Zilla et al. |
| 2006/0147443 A1 | 7/2006 | Schense et al. |
| 2006/0257485 A1 | 11/2006 | Kumacheva |
| 2007/0141105 A1 | 6/2007 | Stein et al. |
| 2007/0167541 A1 | 7/2007 | Ruberti et al. |
| 2007/0190107 A1 | 8/2007 | Tosatti et al. |
| 2008/0193536 A1 | 8/2008 | Khademhosseini et al. |
| 2009/0011009 A1 | 1/2009 | Benita et al. |
| 2009/0294049 A1 | 12/2009 | Udipi et al. |
| 2009/0311324 A1 | 12/2009 | Steinfeld et al. |
| 2010/0036503 A1 | 2/2010 | Chen et al. |
| 2010/0068286 A1* | 3/2010 | Troiano .................. A61K 9/10 424/489 |
| 2011/0087152 A1 | 4/2011 | David et al. |
| 2011/0256628 A1 | 10/2011 | Galperin et al. |
| 2011/0257623 A1 | 10/2011 | Marshall et al. |
| 2012/0015440 A1 | 1/2012 | Otsuka et al. |
| 2012/0027775 A1 | 2/2012 | Won et al. |
| 2012/0114615 A1 | 5/2012 | Burdick et al. |
| 2012/0116511 A1 | 5/2012 | Borden |
| 2012/0156259 A1 | 6/2012 | Rau et al. |
| 2012/0202263 A1 | 8/2012 | Blakely et al. |
| 2012/0308508 A1 | 12/2012 | Saunders et al. |
| 2013/0143056 A1 | 6/2013 | Swan et al. |
| 2013/0228530 A1 | 9/2013 | Di Carlo et al. |
| 2013/0233420 A1 | 9/2013 | Di Carlo et al. |
| 2014/0112960 A1 | 4/2014 | Lin |
| 2014/0120078 A1 | 5/2014 | Wallace et al. |
| 2014/0230909 A1 | 8/2014 | Di Carlo et al. |
| 2015/0071997 A1 | 3/2015 | Garcia et al. |
| 2015/0104427 A1 | 4/2015 | Segura |
| 2015/0202305 A1 | 7/2015 | Maynard et al. |
| 2015/0290362 A1 | 10/2015 | Douglas et al. |
| 2015/0359752 A1 | 12/2015 | Lu et al. |
| 2016/0116453 A1 | 4/2016 | Lutolf et al. |
| 2016/0279283 A1* | 9/2016 | Griffin ................ A61L 26/0019 |
| 2016/0303281 A1 | 10/2016 | Salamone et al. |
| 2017/0368224 A1 | 12/2017 | Griffin et al. |
| 2018/0078671 A1 | 3/2018 | Griffin et al. |

FOREIGN PATENT DOCUMENTS

| | | |
|---|---|---|
| EP | 2542620 A1 | 1/2013 |
| EP | 2542620 B1 | 6/2016 |
| EP | 3169372 A1 | 5/2017 |
| GB | 2431104 A | 4/2007 |
| WO | WO-9509659 A1 | 4/1995 |
| WO | WO-9947129 A1 | 9/1999 |
| WO | WO-0024378 A1 | 5/2000 |
| WO | WO-02071994 A1 | 9/2002 |
| WO | WO-2005006101 A2 | 1/2005 |
| WO | WO-2005035735 A2 | 4/2005 |
| WO | WO-2011101684 A1 | 8/2011 |
| WO | WO-2012155110 A1 | 11/2012 |
| WO | WO-2013071126 A1 | 5/2013 |
| WO | WO-2014025312 A1 | 2/2014 |
| WO | WO-2016011387 A1 | 1/2016 |
| WO | WO-2016096054 A1 | 6/2016 |
| WO | WO-2017136427 A1 | 8/2017 |
| WO | WO-2017142879 A1 | 8/2017 |
| WO | WO-2018136205 A1 | 7/2018 |

OTHER PUBLICATIONS

Anna et al.: Formation of dispersions using "flow focusing" in microchannels: Applied Physics Letters, vol. 82, No. 3, pp. 364-366 (2003).

Annabi et al.: Controlling the Porosity and Microarchitecture of Hydrogels for Tissue Engineering; Tissue Engineering, vol. 16(4):371-383 (2010).

Boula et al.: Journal of Physical Chemistry C: vol. 120:386-395 (2015).

Bramfeld et al.: Scaffold Vascularization: A Challenge for Three-Dimensional Tissue Engineering.*Curr. Med. Chem.*17:3944-3967 (2010).

Burdick et al.: Controlled Degradation and Mechanical Behavior of Photopolymerized Hyaluronic Acid Networks. Biomacromolecules 6:386-391 (2005).

Burdick et al.: Hyaluronic Acid Hydrogels for Biomedical Applications; Adv. Mater.; vol. 23:H41-H56 (2011).

Cam et al.: Systemic evaluation of natural scaffolds in cutaneous wound healing; J. of Materials Chemistry B.; vo. 3 7986-7992 (epub.) (2015).

Cha et al.: microfluidics-Assisted Fabrication of Gelatin-Silica Core-Shell Microgels for Injectable Tissue Construcs, dx.doi..org/10.1021/bm401533y, Biomacromolecules 15, 283-290 (2014).

(56) References Cited

OTHER PUBLICATIONS

Chen et al.: Young's modulus measurements of soft tissues with application to elasticity imaging.*IEEE Trans. Ultrason. Ferroelectr. Freq. Control*43:191-194 (1996).
Chen et al.:Hydrogel-thickened microemulsion for topical administration of drug molecule at an extremely low concentration.*Int. J. Pharm.*341, 78-84 (2007).
Cheng et al.: Unconfined compression of white matter.*J. Biomech.* 40:117-124 (2007).
Conchouso et al.: Three-dimensional parallelization of microfluidic droplet generators for a litre per hour volume production of single emulsions. Lab. Chip 14: 3011-3020 (Aug. 2014).
Das et al.: Biomaterials and Nanotherapeutics for Enhancing Skin Wound Healing. Front Bioeng Biotechnol 4:82 (Oct. 2016).
De France et al. Structured Macroporous Hydrogels: Progress, Challenges, and Opportunities. Adv Healthc Mater 7(1):17 pgs (Jan. 2018).
Discher et al.: Growth Factors, Matrices, and Forces Combine and Control Stem Cells.*Science*324:1673-1677 (2009).
Dreifke et al.: Investigation of potential injectable polymeric biomaterials for bone regeneration; Journal of Biomedical Materials Research; vol. 101A(8:2436-2447 (2013).
Du et al.: Directed assembly of cell-laden microgels for fabrication of 3D tissue constructs. PNAS USA 34:9522-9527 (Jul. 2008).
Du et al.: Fabrication of Hexagonal-Prismatic Granular Hydrogel Sheets. Langmuir 34(11):3459-3466 (2018).
Dunne et al.: Influence of particle size and dissolution conditions on the degradation properties of polylactide-co-glycolide particles. *Biomaterials*21:1659-1668 (2000).
Dynamic Mechanical Analysis (DMA): A beginners Guide, www.Perkinelmer.com; 23 pages (2008), also available at https://www.perkinelmer.com/cmsresources/images/44-74546gde_introductiontodma.pdf (laslt visited Oct. 23, 2018) (2008).
Ehrbar et al.: Elucidating the Role of Matrix Stiffness in 3D Cell Migration and Remodeling, Biophys J., vol. 100(2):284-298 (2011).
Ergenc et al.: Recent Advances in the Modeling of EG Hydrogel Membranes for Biomedical Applications, Biomedical Applications, Biomedical Engineering, Trends in Materials Science, Mr. Anthony Laskovski (Ed.), ISBN: 978-953-307-513-6, Chapter 14, pp. 307-346 (2011).
European Application No. 15821310.8 European Search Report dated Feb. 19, 2018.
Fukano et al.:Characterization of an in vitro model for evaluating the interface between skin and percutaneous biomaterials.*Wound Repair Regen.*14: 484-491 (2006).
Fukano et al.:Epidermal and dermal integration into sphere-templated poly(2-hydroxyethyl methacrylate) implants in mice.*J. Biomed. Mater. Res. A*94A:1172-1186 (2010).
Galiano et al.: Quantitative and reproducible murine model of excisional wound healing.*Wound Repair Regen. Off. Publ. Wound Heal. Soc. Eur. Tissue Repair* Soc.12: 485-492 (2004).
Galler et al.: Self-Assembling Multidomain Peptide Hydrogels: Designed Susceptibility to Enzymatic Cleavage Allows Enhanced Cell Migration and Spreading. J. Am. Chem. Soc. 132: 3217-3223 (2010).
Garstecki et al.: Formation of droplets and bubbles in a microfluidic T-junction—scaling and mechanism of break-up.*Lab. Chip*6:437-446 (2006).
Gaulding et al.: Reversible Inter- and Intra-Microgel Cross-Linking Using Disulfides, Macromolecules; 45; 39-45 (2012).
Gorgieva et al.: Preparation, characterization, and in vitro enzymatic degradation of chitosan-gelatine hydrogel scaffolds as potential biomaterials. J. Biomed. Mater. Res. A 100:1655-1667 (2012).
Grainger. Wound healing: Enzymatically crosslinked scaffolds. Nat Mater 14:662-663 (2015).
Griffin et al.: Accelerated would healing by injectable microporous gel scaffolds assembled from annealed building blocks: Nature materials; vol. 14, No. 7, 737-744; (2015).

Griffin et al.: Hybrid photopatterned enzymatic reaction (HyPER) for in situ cell manipulation. Chembiochem Eur. J. Chem. Biol. 15:233-242 (Jan. 2014).
Guan et al.: PNIPAM microgels for biomedical applications: From Dispersed Particles to 3d Assemblies, sOFT mATTER, vol. 7:6375-6384 (2011).
Guvendiren et al.: Engineering synthetic hydrogel microenvironments to instruct stem cells. CWT Opin Biotechnol 24:841-846 (Oct. 2013).
Hillel et al.: Photoactivated Composite Biomaterial for Soft Tissue Restoration in Rodents and in Humans: Sci Transl Med.: vol. 3(93);93ra67, 24 pages including Supp. (2011).
Hoare et al.: Hydrogels in drug delivery: Progress and challenges: Polymer, vol. 49: 1993-2007 (2008).
Hollister: Porous scaffold design for tissue engineering.*Nat. Mater.* 4:518-524 (2005)
Hosokawa et al.: Handling of Picoliter Liquid Samples in a Poly(dimethylsiloxane)-Based Microfluidic Device.*Anal. Chem.*71: 4781-4785 (1999).
Hu et al.: Hydrogel Nanoparticle Dispersions with Inverse Thermoreversible Gelation, Adv. Mater., 16, No. 4, 305-309 (2004).
Huang et al.: Controlled drug release from hydrogel nanoparticle networks; Journal of Controlled Release; 94; 303-311 (2004).
Huebsch et al.:Harnessing traction-mediated manipulation of the cell/matrix interface to control stem-cell fate.*Nat. Mater.*9: 518-526 (2010).
Hunckler et al. A current affair: electrotherapy in wound healing. J Multidiscip Healthc 10:179-194 (Apr. 2017).
International Application No. PCT/US2015/040962 International Preliminary Report on Patentability dated Jan. 26, 2017.
IUPAC Gold Book: "sintering", 2 pages, also available at http://goldbook.iupac.org/html/S/S05704.html (last visited Oct. 8, 2018) (2018).
Japanese Patent Application No. 2017-502712 Office Action dated Mar. 22, 2019.
Jgamadze et al.: Colloids as mobile substrates for the implantation and integration of differentiated neurons into the mammalian brain. PloS One 7, e30293 (2012).
Jgamadze et al. Thermoswitching Microgel Carriers Improve Neuronal Cell Growth and Cell Release for Cell Transplantation. Tissue Eng. Part C Methods (Jan. 2014).
Jia et al.: Hyaluronic Acid-Based Microgels and Microgel Networks for Vocal Fold Regeneration, Biomacromolecules 7(12): 3336-3344 (2006).
Jiang et al. Cell-laden microfluidic microgels for tissue regeneration. Lab Chip 16(23):4482-4506 (Nov. 2016).
Kawakatsu et al.: Regular-sized cell creation in microchannel emulsification by visual microprocessing method.*J. Am. Oil Chem. Soc.*74:317-321 (1997).
Kim et al.: Three-Dimensional Porous Biodegradable Polymeric Scaffolds Fabricated with Biodegradable Hydrogel porogens, Tissue Engineering: Part C; vol. 15(4):583-594 (2009).
Kong et al.: Controlling rigidity and degradation of alginate hydrogels via molecular weight distribution. Biomacromolecules 5:1720-1727 (2004).
Lam et al.: Design of cell-matrix interactions in hyaluronic acid hydrogel scaffolds; Acta Biomateriallia, vol. 10, No. 4, pp. 1471-1580; XP55449152 (2014).
Lee et al.: Tissue, cell and engineering. Curr. Opin. Biotechnol. 24:827-829 (Oct. 2013).
Li et al.: DNA-templated assembly of droplet-derived PEG microtissues. *Lab. Chip*11:2967-2975 (2011).
Lin et al.: Eph/ephrin signaling in epidermal differentiation and disease.*Semin. Cell Dev. Biol.*23:92-101 (2012).
Lin et al.: Peg Hydrogels for the controlled Release of Biomelcules in Regenerative Medicine, Pharmaceutical Research, Kluwer Academic Publishers-Plenum Publishers, NL, vol. 26, No. 3, pp. 631-643, XP019686137 (2008).
Ling et al.: A cell-laden microfluidic hydrogel. Laab Chip 7(6):756-762 (Jun. 2007).
Lucas et al.:Differential Roles of Macrophages in Diverse Phases of Skin Repair.*J. Immunol.*184:3964-3977 (2010).

(56) References Cited

OTHER PUBLICATIONS

Lutolf, M. P. and Hubbell, J. A. Synthetic biomaterials as instructive extracellular microenvironments for morphogenesis in tissue engineering.*Nat. Biotechnol.*23:47-55 (2005).
Lutolf, M. P.et al.Synthetic matrix metalloproteinase-sensitive hydrogels for the conduction of tissue regeneration: Engineering cell-invasion characteristics.*Proc. Natl. Acad. Sci.*100: 5413-5418 (2003).
Madden, L. R.et al. Proangiogenic scaffolds as functional templates for cardiac tissue engineering.*Proc. Natl. Acad. Sci.*107:15211-15216 (2010).
Mallis: De Novo Program, FDA, 64 slides (Nov. 4, 2014) alhttps://www.fda.gov/downloads/training/cdrhlearn/ucm421766.pdf (last visited Oct. 4, 2018).
Muehleder et al. Connections matter: channeled hydrogels to improve vascularization. Front Bioeng Biotechnol 2:52 (Nov. 2014).
Murata: Polymerization Chapter 17: Rheology: Theory and Application to Biomaterials: pp. 403-426 (2012).
Nichols et al.: Factors affecting size and swelling of ply(ethylene glycol) microspheres formed in aqueous sodium sulfate solutions without surfactants, Biomaterials, vol. 30:5283-5291 (2009).
Nih et al. Injection of Microporous Annealing Particle (MAP) Hydrogels in the Stroke Cavity Reduces Gliosis and Inflammation and Promotes NPC Migration to the Lesion. Adv Mater 29(32):1606471 (2017).
Park et al.: Bovine Primary Chondrocyte Culture in Synthetic Matrix Metalloproteinase-Sensitive Poly(ethylene glycol)-Based Hydrogels as a Scaffold for Cartilage Repair; Tissue Engineering; vol. 10(3/4):515-522 (2004).
Parker, et al., Tissue response to mechanical vibrations for 'sonoelasticity imaging'.*Ultrasound Med. Biol.*16:241-246 (1990).
Pautot, et al., Colloid-guided assembly of oriented 3D neuronal networks.*Nat. Methods*5: 735-740 (2008).
PCT/US2015/040962 International Search Report and Written Opinion dated Oct. 7, 2015.
PCT/US2017/068243 International Search Report and Written Opinion dated May 3, 2018.
Peters, et al., Engineering vascular networks in porous polymer matrices.*J. Biomed. Mater. Res.*60:668-678 (2002).
Qi et al. DNA-directed self-assembly of shape-controlled hydrogels. Nat. Commun. 4:2275 (2013).
Renkema et al.: The effect of pH on heat denaturation and gel forming properties of soy proteins; Journal of Biotechnology; vol. 79-223-230 (2000).
Richardson, et al., Polymeric system for dual growth factor delivery. *Nat. Biotechnol.*19:1029-1034 (2001).
Rouquerol et. al.: Recommendations for the Characterization of Porous Solids, IUPAC Technical Report, Pure & Appl. Chem., vol. 66(8):1758(1994).
Rustad, K. C.et al.Enhancement of mesenchymal stem cell angiogenic capacity and stemness by a biomimetic hydrogel scaffold. *Biomaterials*33:80-90 (2012).
Sacanna et al.: Lock and key colloids; Nature, vol. 464:575-578 (2010).
Samani et al.: Measuring the elastic modulus of ex vivo small tissue samples.*Phys. Med. Biol.*48: 2183 (2003).
Saunders et al.: Microgel particles as model colloids: theory, properties and applications, Adv. Colloids interface Sci; 80 ; 1-25 (1999).
Schense et al.: Cross-linking exogenous bifunctional peptides into fibrin gels with factor XIIIa.*Bioconjug. Chem.*10:75-81 (1999).
Scott et al.: Modular scaffolds assembled around living cells using poly(ethylene glycol) microspheres with macroporation via a non-cytotoxic porogen; Acta Biomaterialia; vo. 6:29-38 (2010).
Seliktar et al.: MMP-2 sensitive, VEGF-bearing bioactive hydrogels for promotion of vascular healing.*J. Biomed. Mater. Res. A*,68:704-716 (2004).
Selimovic et al.: Microscale Strategies for Generating cell encapsulating hydrogels; Polymers, vol. 4: 1554-f1679 (2012).

Shih: Thesis: Step-Growth Thiol-ene Photopolymerization to Form Degradable, Cytocompatible and Multi-structural Hydrogels: Purdue University, Indianapolis, Indiana; 92 pages (2013).
Shin: Dissertation: Development of Cell-Laden Hydrogels with High Mechanical Strength for Tissue Engineering Applications: MIT: Department of Materials; Science and Engineering; 86 pages (2014).
Smith: Dissertation: Engineering Poly(ethylene glycol) Materials to Promote Cardiogenesis: Washington University; St. Louis, Missouri; 142 pages (2013).
Sokic et al. In situ generation of cell-laden porous MMP-sensitive PEGDA hydrogels by gelatin leaching. Macromol. Biosci.14:731-739 (May 2014).
U.S. Appl. No. 16/457,510 Restriction Requirement dated Aug. 13, 2019.
Australian Application No. 2015289474 Examination Report No. 1 dated Nov. 30, 2018.
Gan et al.: In situ gelation of P(NIPAM-HEMA) microgel dispersion and its applications as injectable 3D cellscaffold. Biomacromolecules, 10, 1410-1415, Jan. 2009.
Karg et al.: New "smart" poly(NIPAM) microgels and nanoparticle microgel hybrids: Properties and advances in characterisation, Current Opinion in Colloid & Interface Science 14; 438-450 (2009).
Stachowiak, et al., Bioactive Hydrogels with an Ordered Cellular Structure Combine Interconnected Macroporosity and Robust Mechanical Properties. Adv. Mater. 17:399-403 (2005).
Stejskalova et al. Using biomaterials to rewire the process of wound repair. Biomater Sci 5(8):1421-1434 (Jul. 2017).
Stratman, et al., Pericyte recruitment during vasculogenic tube assembly stimulates endothelial basement membrane matrix formation. *Blood*114:5091-5101 (2009).
Syrett et al.: Functional, star polymeric molecular carriers, built from biodegradable microgel/nanogel cores, Chem. Commun; 47; 1449-1451 (2011).
Thaiboonrod et al.: Doubly crosslinked poly(vinyl amine)) microgels: hydrogels of covalently inter-linked cationic microgel particles, J. Mater. Chem. B, 2014, 2, 110 (published online 2013).
Thorne et al.: Microgel applications and commercial considerations; Colloid. Polym. Sci., vol. 289:625-646 (2011).
Trentin et al.: Peptide-matrix-mediated gene transfer of an oxygen-insensitive hypoxia-inducible factor-1a variant for local induction of angiogenesis, PNAS, vol. 103(8):2506-2511 (2006).
Turturro et al.: MMP-Sensitive PEG Diacrylate Hydrogels with Spatial Variations in Matrix Properties Stimulate Directional Vascular Sprout Formation, PLos One 8(3): e58897; doi:10.1371/journal.pone.0058897 (2013).
U.S. Appl. No. 15/701,113 Office Action dated Mar. 27, 2018.
U.S. Appl. No. 15/701,113 Restriction Requirement dated Nov. 22, 2017.
Wade, R. J. & Burdick, J. A. Engineering ECM signals into biomaterials. Mater. Today 15: 454-459 (2012).
Wang, D.-A.et al.Multifunctional chondroitin sulphate for cartilage tissue-biomaterial integration.*Nat. Mater.*6:385-392 (2007).
Wang et al. Novel Biodegradable Porous Scaffold Applied to Skin Regeneration. PLoS ONE8:e56330 (Jun. 2013).
Xin et al. Assembly of PEG Microgels into Porous Cell-Instructive 3D Scaffolds via Thiol-Ene Click Chemistry. Adv Healthc Mater 7(11):e1800160 (Jun. 2018).
Yadong et al.: Self-Assembly of Monodispersed Spherical Colloids into Complex Aggregates with Well-Defined Sizes, Shapes, and Structures; Adv. Mater., 13/4; 267-271 (2001).
Yan et al.: Rheological properties of peptide-based hydrogels for biomedical and other applications: chem. Soc. Rev.; vo. 39:3528-3540 (2010).
Yang, et al., The Design of Scaffolds for Use in Tissue Engineering. Part I. Traditional Factors.*Tissue Eng.*7:679-689 (2001).
Yeh,et al.,Elastic modulus measurements of human liver and correlation with pathology.*Ultrasound Med.* Biol.28:467-474 (2002).
Yin et al.: Self-Assembly of Monodispersed Spherical Colloids into Complex Aggregates with Well-Defined Sizes, Shapes, and Structures; Adv. Mater.; 13/4; 267-271 (2001).
Yongdoo et al.: Bovine primary chondrocyte culture in synthetic matrix metalloprteinase-sensitive poly(ethylene glycol)-based hydrogels

(56) References Cited

OTHER PUBLICATIONS as a scaffold for cartilage repair, Tissue Engineering, Larchmont, NY, US, vol. 10, No. 3-4, pp. 515-522, XP002464246 (2004).
Zhou et al.: Viscoelastic Behavior and In Vivo Release Study of Microgel Dispersions with Inverse Thermoreversible Gelation, Biomacromolecules; 9/1; 142-148 (2007).
Chan et al.: Functionalizable hydrogel microparticles of tunable size and stiffness for soft-tissue filler applications. Acta Biomaterialia 10:2563-3573 (2014).
Hao et al.: Visible light cured thiol-vinyl hydrogels with tunable degradation for 3D cell culture. Acta Biomater 10:1-27 (2014).
Quinn et al.: Biocompatible, glucose-permeable hydrogel for in situ coating of implantable biosensors. Biomaterials 18:1665-1670 (1997).
Rolfe et al.: The Fibrotic Response to Implanted Biomaterials: Implications for Tissue Engineering. Regenerative Medicine and Tissue Engineering—Cells and Biomaterials 26:551-570 (2011).
Tous et al.: Injectable Acellular Hydrogels for Cardiac Repair. J. of Cardiovasc. Trans. Res. 4:528-542 (2011).
U.S. Appl. No. 16/457,517 First Action Interview Pre-Interview Communication dated Sep. 18, 2019.

\* cited by examiner

METHODS OF MANUFACTURING INJECTABLE MICROGEL SCAFFOLDS

CROSS-REFERENCE TO RELATED APPLICATIONS

This application is a continuation of International Application No. PCT/US17/068243, filed on Dec. 22, 2017, which claims the benefit of U.S. Provisional Application No. 62/440,370, filed Dec. 29, 2016, both of which are incorporated by reference herein in their entirety.

BACKGROUND OF THE DISCLOSURE

Current porous synthetic hydrogels used as such healing agents are produced by methods that require toxic removal of porogens to form pores, or degradation of encapsulated microparticles, which requires these constructs to be either cast ex vivo, preventing them from seamlessly integrating with the surrounding tissue like an injectable biomaterial or requires long-term in vivo development to resolve the porous structure.

SUMMARY OF THE DISCLOSURE

Cell migration to a site of injury or surgery is essential for healing. Therefore, wound healing agents used at these sites ideally do not impede cellular migration. Implantation of medical devices, such as biomaterials, prosthetics and cardiac pacemakers, is common practice in modern medicine. However, tissues that are subjected to medical device implantation produce a complex set of immune responses, including for example, to the device and the implantation procedure, including but not limited to inflammation, wound healing, foreign body reactions and fibrous encapsulation of the device. These responses do not always result in a desirable outcome for the patient. For instance, the site of implantation may develop scar tissue or fibrotic tissue that is deleterious to the function of the surrounding tissue and the subject.

The systems and methods disclosed herein aim to improve the tissue-device interface through the use of microporous gel systems. These microporous gel systems, in certain embodiments, are applied to a surgical void, such as a medical device implantation site, and around the medical device. A stimulus such as light is then applied to the microporous gel system to create a microporous scaffold (see e.g., FIG. 1). The microporous gel system disclosed herein can act as a buffer between the tissue and the device, promoting healing of the tissue and incorporation of the device into the tissue, while mitigating or avoiding fibrous encapsulation of the device, inflammation or infection. The presence of the interconnected pores between the medical implant and the surrounding tissue (see, e.g., FIG. 2), provided by the microporous gel system, create a unique environment that does not lead to a chronic inflammatory response or fibrous tissue formation. The ability of tissue (or cells thereof) to migrate into the material without the need for degradation is an important aspect to the invention in the context of implanted medical devices.

In some instances, microporous gel systems disclosed herein provide for prevention and treatment of infections via antimicrobial activity. In some instances, microporous gel systems disclosed herein provide for mitigation of other negative characteristics of surgical implant sites such as pain and chronic inflammation. In some instances, microporous gel systems disclosed herein provide for stable shelf products that release a tissue site treatment (e.g., an antimicrobial treatment) when placed in a surgical/implant site. Tissue site treatments may provide for minimal/absent fibrosis around a surgical site pocket via anti-fibrotic capability of microporous scaffold Tissue site treatments may provide for minimal/absent inflammation at a surgical site pocket via anti-inflammatory capability of microporous scaffolds.

In some instances, microporous gel systems disclosed herein provide for physically stabilizing medical devices in an implant or surgical site. In some instances, microporous gel systems disclosed herein provide for holding a medical device in place by a microporous scaffold. In some instances, medical device of one size can be applied to surgical/implant sites of different shapes and sizes, with extra space in the surgical/implant site and around the medical device filled by a microporous gel system disclosed herein during/after implantation. Using a microporous gel system disclosed herein, medical devices and implants of many sizes and shapes can be interfaced with surgical pockets (in a tissue) of varying sizes and shapes because excess surgical site space is filled by the microporous gel system.

Features and characteristics of microporous gel systems disclosed herein provide for applying the microporous gel systems in a manner that is custom to a subject and the features of the subject's surgical site or implant site. In some instances, methods disclosed herein comprise applying a microporous gel system during implantation of a medical device. In some instances, methods disclosed herein comprise applying a microporous gel system during implantation of a medical device. In some instances, methods disclosed herein comprise applying a microporous gel system after implantation of a medical device. In some instances, methods disclosed herein comprise filling an implantation site or surgical site with a microporous gel system during at least one of before, during, and after implant positioning in the surgical site.

As one of skill in the art will understand from the description and examples presented herein, medical device manufacturing (size, shape, etc.) is not dependent upon manufacturing of microporous scaffolds disclosed herein, or vice versa. Advantageously, the adaptable, customizable microporous scaffolds disclosed herein may be applied immediately to medical devices of any shape, size, etc., and/or surgical pockets of any shape, size, etc.

Disclosed herein, in some aspects, are systems comprising: a collection of flowable microgel particles, wherein the flowable microgel particles comprise a backbone polymer; at least one annealing component; and a medical device, wherein the flowable microgel particles are capable of being linked together via the at least one annealing component to form a stabilized scaffold having interstitial spaces therein. Also disclosed herein, in some aspects, are systems comprising: a collection of flowable microgel particles, wherein the flowable microgel particles comprise a backbone polymer; at least one annealing component; and a medical device, wherein the flowable microgel particles are linked together via the at least one annealing component to form a stabilized scaffold having interstitial spaces therein. The systems may comprise an intercrosslinker that links the flowable microgel particles together via the at least one annealing component. The systems may comprise an annealing agent that links the flowable microgel particles together via the at least one annealing component. The annealing agent may be an intercrosslinking agent. The systems may comprise a first annealing component and a second annealing component. The first annealing component and the second annealing component may be the same. The first annealing component and the second annealing component may be different. The at least one annealing component may be a substrate for an enzyme of a mammalian subject. In some instances, a first annealing component and a second annealing component are linked together when exposed to a condition in a mammalian subject. The medical device may be a medical implant. The medical device may comprise an electrode. The medical device may comprise an electrical component. The medical device may comprise a coating, wherein the coating comprises at least one of the annealing component and an annealing agent. The medical implant may be a cardiac implantable electronic device. The cardiac implantable electronic device may be a pacemaker. The cardiac implantable electronic device may be a defibrillator. The medical implant may be a neural implantable electronic device. The stabilized scaffold may maintain placement of the medical device in a surgical void of a subject. The stabilized scaffold may have a custom form determined by the medical device and the surgical void. In some instances, the stabilized scaffold comprises non-covalent bonds between the flowable microgel particles. In some instances, the stabilized scaffold comprises covalent bonds between the flowable microgel particles. In some instances, systems comprise a therapeutic agent. In some instances, the therapeutic agent is an anti-inflammatory agent, an antimicrobial agent, or an analgesic. In some instances, the therapeutic agent is incorporated in the stabilized scaffold. In some instances, systems comprise a therapeutic agent, wherein the stabilized scaffold releases the therapeutic agent from the stabilized scaffold when the stabilized scaffold is present in a mammalian subject. In some instances, the stabilized scaffold releases at least a portion of the therapeutic agent from the stabilized scaffold in less than one day from its initial presence in the mammalian subject. In some instances, the stabilized scaffold releases the therapeutic agent from the stabilized scaffold over a period of less than 1 day to 100 days. In some instances, systems comprise a therapeutic agent releasing agent that releases the therapeutic agent from the stabilized scaffold. In some instances, the therapeutic agent is released by tissue mediated hydrolysis. In some instances, the therapeutic agent is released by passive hydrolysis. In some instances, the therapeutic agent is released by a temperature change. In some instances, systems comprise a nanoparticle. In some instances, the therapeutic agent is connected to or contained within the nanoparticle. In some instances, the nanoparticle is a mesoporous silica nanoparticle. In some instances, the nanoparticle comprises poly(lactic-co-glycolic acid). In some instances, the nanoparticle comprises chitosan. In some instances, the nanoparticle comprises hyaluronic acid. In some instances, the nanoparticle comprises a poly(anhydride), a poly(amide), a poly(ortho ester), a polycaprolactone, or a combination thereof. In some instances, the nanoparticle comprises a polymer with a lower critical solution temperature (LCST). In some instances, the polymer is poly(N-isopropylacrylamide) or a co-polymer thereof. In some instances, the nanoparticle comprises a polymer with an upper critical solution temperature (UCST). In some instances, the polymer is poly(hydroxyethylmethacrylate), polyethylene oxide, or poly(ethyleneoxide)-poly (propyleneoxide)-poly(ethyleneoxide). In some instances, the nanoparticle comprises a self-immolating polymer. In some instances, the polymer is poly(p-aminobenzyl oxycarbonyl). In some instances, the polymer is capped with a cage that can be released upon a stimulus. In some instances, the system comprises a core-shell nanoparticle system. In some instances, a first portion of the flowable microgel particles comprises the core-shell nanoparticle system and wherein the second portion of flowable microgel particles comprises a shell-dissolving agent, wherein the shell-dissolving agent is capable of releasing the therapeutic agent when the first portion of the flowable microgel particles is in contact with the second portion of flowable microgel particles. In some instances, systems comprise a first container containing the first portion and a second container containing the second portion. In some instances, the intercrosslinker is degradable in a mammalian subject. In some instances, systems comprise a cell adhesive peptide. In some instances, the annealing agent comprises a light source. In some instances, the collection of flowable microgel particles and annealing agent are stored or administered from a single container. In some instances, at least two of the flowable microgel particles are present in separate containers. In some instances, the first annealing component and the second annealing component are present in separate containers. In some instances, systems comprise an application device, wherein the application device is configured to apply the flowable microgel particles and the at least one annealing component to a tissue of a subject. In some instances, the application device comprises a syringe, a spatula, a squeezable tube or a cannula. In some instances, the application device comprises a multi-barrel syringe, and wherein at least a first portion of the flowable microgel particles or a first portion of the annealing component is in a first barrel, and a second portion of the flowable microgel particles or a second portion of the annealing component is in a second barrel. In some instances, the microporous gel system has a shelf life of at least about one year at room temperature.

Disclosed herein, in some aspects, are systems comprising: a collection of flowable microgel particles, wherein the flowable microgel particles comprise a backbone polymer; at least one annealing component; and a medical device, wherein the flowable microgel particles are capable of being linked together via the at least one annealing component to form a stabilized scaffold having interstitial spaces therein, for use in the treatment of a wound or surgical site.

Disclosed herein, in some aspects are methods of treating a site of a medical device in a tissue of a subject comprising administering to the site: a collection of flowable microgel particles, wherein the flowable microgel particles comprise a backbone polymer; at least one annealing component; and a medical device, wherein the flowable microgel particles are capable of being linked together via the at least one annealing component to form a stabilized scaffold having interstitial spaces therein.

Disclosed herein, in some aspects, are methods of reducing or preventing fibrosis at a site of a medical device in a tissue of a subject comprising administering to the site: a collection of flowable microgel particles, wherein the flowable microgel particles comprise a backbone polymer; at least one annealing component; and a medical device, wherein the flowable microgel particles are capable of being linked together via the at least one annealing component to form a stabilized scaffold having interstitial spaces therein.

Disclosed herein, in some aspects, are methods of reducing or preventing inflammation at a site of a medical device in a tissue of a subject comprising administering to the site: a collection of flowable microgel particles, wherein the flowable microgel particles comprise a backbone polymer; at least one annealing component; and a medical device, wherein the flowable microgel particles are capable of being linked together via the at least one annealing component to form a stabilized scaffold having interstitial spaces therein.

In some instances, the medical device is a surgical device. In some instances, the medical device is a medical implant. In some instances, methods comprise administering at least one of the annealing component and the flowable microgel particles to the site before administering the medical device to the site. In some instances, methods comprise administering at least one of the annealing component and the flowable microgel particles to the site after administering the medical device to the site. In some instances, methods comprise co-administering at least one of the annealing component and the flowable microgel particles, and the medical device to the site. In some instances, methods comprise administering at least one of the annealing component and the flowable microgel particles with a syringe, cannula, squeezable tube or spatula. In some instances, methods comprise administering an annealing agent. In some instances, methods comprise administering the annealing agent before administering at least one of the annealing component and the flowable microgel particles. In some instances, methods comprise administering the annealing agent after administering at least one of the annealing component and the flowable microgel particles. In some instances, methods comprise co-administering the annealing agent and at least one of the annealing component and the flowable microgel particles. In some instances, methods comprise administering a therapeutic agent to the site. In some instances, methods comprise administering a therapeutic agent releasing agent to the site, wherein the therapeutic agent releasing agent releases the therapeutic agent from the stabilized scaffold to the site or tissue. In some instances, methods comprise incorporating the therapeutic agent into the stabilized scaffold. In some instances, the stabilized scaffold comprises a core-shell nanoparticle system wherein the therapeutic agent is connected to or contained within the core-shell nanoparticle system, comprising applying an external stimulus to the stabilized scaffold to release the therapeutic agent to the site or tissue. In some instances, the external stimulus selected from light, electromagnetic radiation, or temperature change. In some instances, methods comprise changing a condition of the site after formation of the stabilized scaffold. In some instances, methods comprise changing a condition of the site before formation of the stabilized scaffold. In some instances, changing the condition comprises at least one of changing temperature of the site, changing pH of the site, changing chemistry of the site, applying an exogenous enzyme, activating an endogenous enzyme, applying a magnetic field, applying a form of radiation, applying light, and applying ultrasound.

Disclosed herein, in some aspects, are methods of treating a heart condition comprising administering to a subject in need thereof: a collection of flowable microgel particles, wherein the flowable microgel particles comprise a backbone polymer; at least one annealing component; and a cardiac implantable electronic device, wherein the flowable microgel particles are capable of being linked together via the at least one annealing component to form a stabilized scaffold having interstitial spaces therein. In some instances, the heart condition is a heart arrhythmia. In some instances, the heart condition is a sustained ventricular tachycardia. In some instances, the heart condition is a ventricular fibrillation.

Disclosed herein, in some aspects are methods of treating a neurological condition comprising administering to a subject in need thereof: a collection of flowable microgel particles, wherein the flowable microgel particles comprise a backbone polymer; at least one annealing component; and a neural implantable electronic device, wherein the flowable microgel particles are capable of being linked together via the at least one annealing component to form a stabilized scaffold having interstitial spaces therein.

Disclosed herein, in some aspects, are methods of producing a microporous scaffold, comprising: synthesizing a first portion of flowable microgel particle in the presence of a first annealing component and a second annealing component, wherein there is more of the first annealing component than the second annealing component to produce a first functionalized microgel particle; synthesizing a second portion of flowable microgel particle in the presence of the first annealing component and the second annealing component, wherein there is more of the second annealing component than the first annealing component to produce a second functionalized microgel particle; combining the first functionalized microgel particle and the second functionalized microgel particle such that the first functionalized microgel particle and the second functionalized microgel particle connect, thereby producing a microporous scaffold of microgel particles having interstitial spaces therebetween. In some instances, there is at least 1% more of the first annealing component than the second annealing component in step (a). In some instances, there is at least 1% more of the second annealing component than the first annealing component in step (b). In some instances, at least one of the first annealing component and the second annealing component comprise a functional group selected from a vinyl sulfone, thiol, amine, imidazole, aldehyde, ketone, hydroxyl, azide, alkyne, vinyl, alkene, maleimide, carboxyl, N-hydroxysuccinimide (NHS) ester, isocyanate, isothiocyanate, hydroxylamine, and thione. In some instances, the first functionalized microgel particle and the second functionalized microgel particle connect through a reaction selected from Michael addition, amide bond coupling, Diels-Alder cycloaddition, Huisgen 1,3-dipolar cycloaddition, reductive amination, carbamate linkage, ester linkage, thioether linkage, disulfide bonding, hydrazone bonding, oxime coupling, and thiourea coupling. In some instances, the first functionalized microgel particle and the second functionalized microgel particle connect to produce a covalent bond. In some instances, the first functionalized microgel particle and the second functionalized microgel particle connect to produce a non-covalent bond. In some instances, the first functionalized microgel particle and the second functionalized microgel particle connect to produce a connection selected from a C—C bond, an amide bond, an amine bond, a carbamate linkage, an ester linkage, a thioether linkage, a disulfide bond, a hydrazine bond, an oxime coupling and a thiourea coupling. In some instances, at least one step of the method is performed in situ.

Disclosed herein, in some aspects, are methods of producing a microporous scaffold, comprising: synthesizing flowable microgel particles; contacting a first portion of the flowable microgel particles with a first annealing component to produce a first functionalized microgel particle; contacting a second portion of the flowable microgel particles with a second annealing component to produce a second functionalized microgel particle; combining the first functionalized microgel particle and the second functionalized microgel particle such that the first functionalized microgel particle and the second functionalized microgel particle connect, thereby producing a microporous scaffold of microgel particles having interstitial spaces therebetween. In some instances, at least one of the first annealing component and the second annealing component comprise a reactive moiety selected from a catechol, a sialic acid, a boronic acid, a molecular cage, adamantane, biotin, and streptavidin. In some instances, the molecular cage is selected from a cyclodextrin, a cucurbituril, a calixarene, a pillararene, a crown ether, a cavitand, a cryptand, and a carcerand. In some instances, the first functionalized microgel particle and the second functionalized microgel particle connect through a covalent bond. In some instances, the covalent bond is selected from an amide, ester, C—C bond, carbamate, disulfide bond, oxime, thiourea, hydrazone, and imine. In some instances, the first functionalized microgel particle and the second functionalized microgel particle connect through a non-covalent bond. In some instances, the non-covalent bond is selected from an electrostatic interaction, a hydrogen bond, a cation-π, π-π stack, a metal-ligand bond, a van der Waals interaction, and a non-covalent host-guest inclusion complex. In some instances, at least one step of the method is performed in situ. In some instances, methods comprise contacting the first functionalized microgel particle and the second functionalized microgel particle with an intercrosslinker in order to connect the first functionalized microgel particle and the second functionalized microgel particle. In some instances, contacting occurs in situ. In some instances, contacting occurs after synthesizing the flowable microgel particles. In some instances, the intercrosslinker comprises at least one functional group. In some instances, the intercrosslinker comprises at least two functional groups. In some instances, at least one functional group is selected from a vinyl sulfone, a thiol, an amine, an imidazole, an aldehyde, a ketone, a hydroxyl, an azide, an alkyne, a vinyl, an alkene, a maleimide, a carboxyl, a N-Hydroxysuccinimide (NHS) ester, an isocyanate, an isothiocyanate, ahydroxylamine, and a thione. In some instances, connecting the first functionalized microgel particle and the second functionalized microgel particle comprises a reaction selected from Michael addition, amide bond coupling, Diels-Alder cycloaddition, Huisgen 1,3-dipolar cycloaddition, reductive amination, carbamate linkage, ester linkage, thioether linkage, disulfide bond, hydrazone bond, oxime coupling, and thiourea coupling. In some instances, methods comprise contacting the first functionalized microgel particle and the second functionalized microgel particle with an intercrosslinking agent. In some instances, the intercrosslinking agent comprises a reducing agent. In some instances, the reducing agent comprises at least one of dithiothreitol, dithioerythritol, L-glutathione, and tris (2-carboxyethyl) phosphine hydrochloride. In some instances, the intercrosslinking agent comprises an oxidizing agent. In some instances, the oxidizing agent comprises at least one of horseradish peroxidase (HRP), sodium periodate, and silver nitrate. In some instances, the intercrosslinking agent induces self-crosslinking of functional groups present on at least one of the annealing component flowable microgel particles or annealing components to produce a crosslinkage. In some instances, the crosslinkage comprises at least one of a covalent bond, a coordination complex, a hydrogen bond, an electrostatic interaction, a cation-π interaction, a π-π stack, and a van der Waals interaction. In some instances, methods comprise contacting the first functionalized microgel particle and the second functionalized microgel particle with the intercrosslinking agent in situ. In some instances, methods comprise applying an external stimulus to the microporous scaffold to release the intercrosslinker. In some instances, applying an external stimulus to the microporous scaffold occurs indirectly by applying the external stimulus to tissue around the microporous scaffold. In some instances, the external stimulus is selected from light, an electromagnetic field, ultrasound, heat, cooling, and a combination thereof. In some instances, methods comprise incorporating a therapeutic agent into the stabilized scaffold. In some instances, incorporating comprises at least one of diffusing the therapeutic agent into the collection of flowable microgel particles; covalently linking the therapeutic agent to the flowable microgel particles; and photo-caging the therapeutic agent to the microgel particles. In some instances, incorporating comprises encapsulating the therapeutic agent in a nanoparticle, and mixing the therapeutic agent and the nanoparticle with the flowable microgel particles. In some instances, the nanoparticle and the therapeutic agent are lyophilized, comprising dissolving the nanoparticle and the therapeutic agent in aqueous buffer prior to mixing the nanoparticle and the therapeutic agent with the flowable microgel particles. In some instances, transferring and removing occur substantially simultaneously.

Disclosed herein, in some aspects, are methods of purifying flowable microgel particles comprising: obtaining a membrane filtration system; transferring flowable microgel particles from a first solvent to a second solvent, wherein the second solvent is immiscible with the first solvent, by controlled addition of a third solvent to the first solvent such that a single miscible phase containing the flowable microgel particles is maintained; and removing an impurity from the flowable microgel particles. In some instances, transferring and removing occur substantially simultaneously. In some instances, the membrane filtration system requires a single miscible phase for function. In some instances, the membrane filtration system is selected from tangential flow filtration (TFF), ultrafiltration-diafiltration (UFDF), microfiltration-diafiltration (MFDF), or hollow-fiber-diafiltration (HFDF). In some instances, the first solvent is a non-polar oil and the second solvent is water. In some instances, the third solvent is an alcohol solution. In some instances, the impurity is a surfactant.

Disclosed herein, in some aspects, are methods of concentrating flowable microgel particles in a solution or suspension comprising: pumping the flowable microgel particles through a membrane filtration system while a continuous phase volume is removed; continually concentrating the flowable microgel particles at a controlled membrane flux; and maintaining a wall shear stress inside the membrane filtration system. In some instances, the membrane filtration system is selected from tangential flow filtration (TFF), ultrafiltration-diafiltration (UFDF), microfiltration-diafiltration (MFDF), or hollow-fiber-diafiltration (HFDF). In some instances, the membrane flux is controlled between 100 and 1000 L/m²h. In some instances, the wall shear stress is maintained between $100 \text{ s}^{-1}$ and $10{,}000 \text{ s}^{-1}$.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 10A shows multinucleated giant cell (MNGC) formation. FIG. 10B shows acute inflammation. FIG. 10C shows wound atrophy was reduced the microporous scaffold.

FIG. 11A shows re-epithelialization. FIG. 11B shows quantification of fibrosis.

FIG. 12A shows quantification of vessel ingrowth. FIG. 12B shows sizes of vessels formed. FIG. 12C shows the percentage of vessels larger than 10 μm.

DETAILED DESCRIPTION OF THE DISCLOSURE

Figure 1:
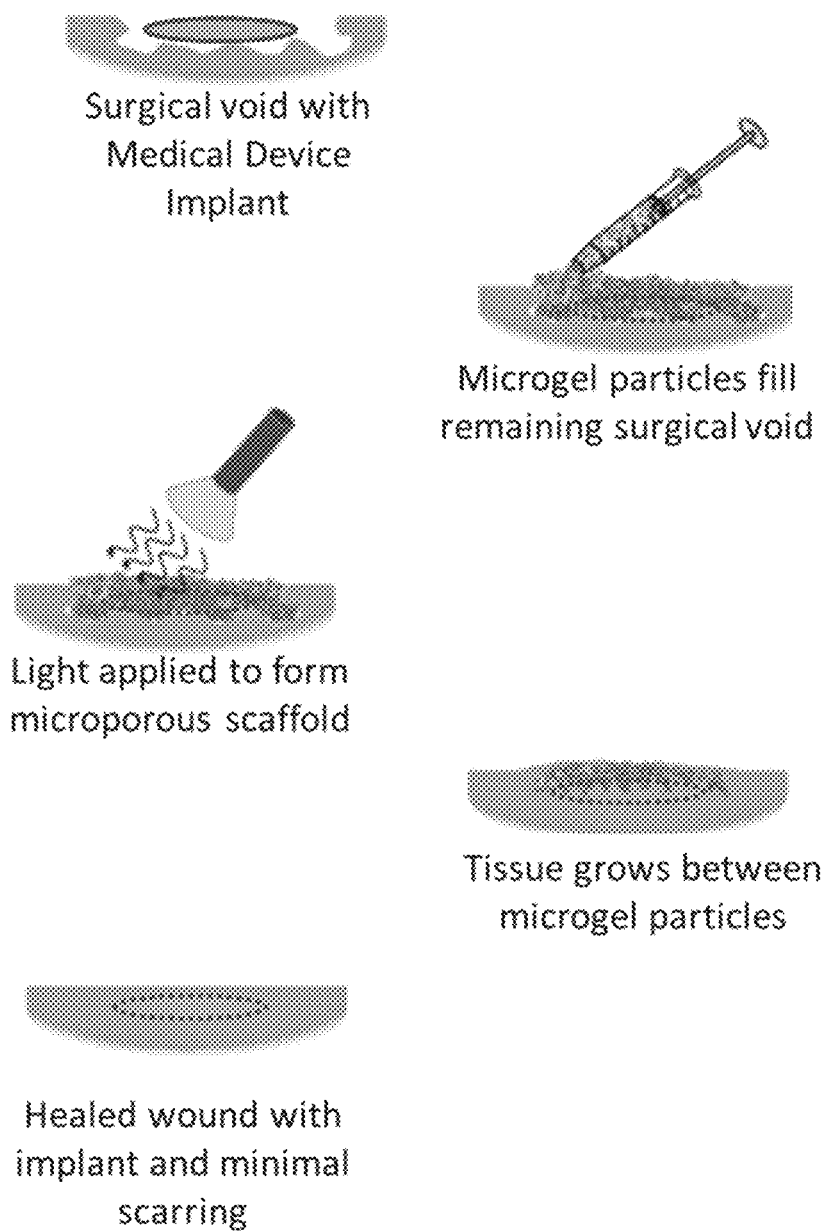
FIG. 1 shows an exemplary application of a microporous gel disclosed herein to a wound void with a medical device implant. A syringe applicator of a solution of free flowing microgel particles is applied to the wound void. Microgel particles are annealed using light energy to form a porous network. The porous network allows cells to migrate through the gel, with the result of improving the health of the wound-device interface.
Figure 2:
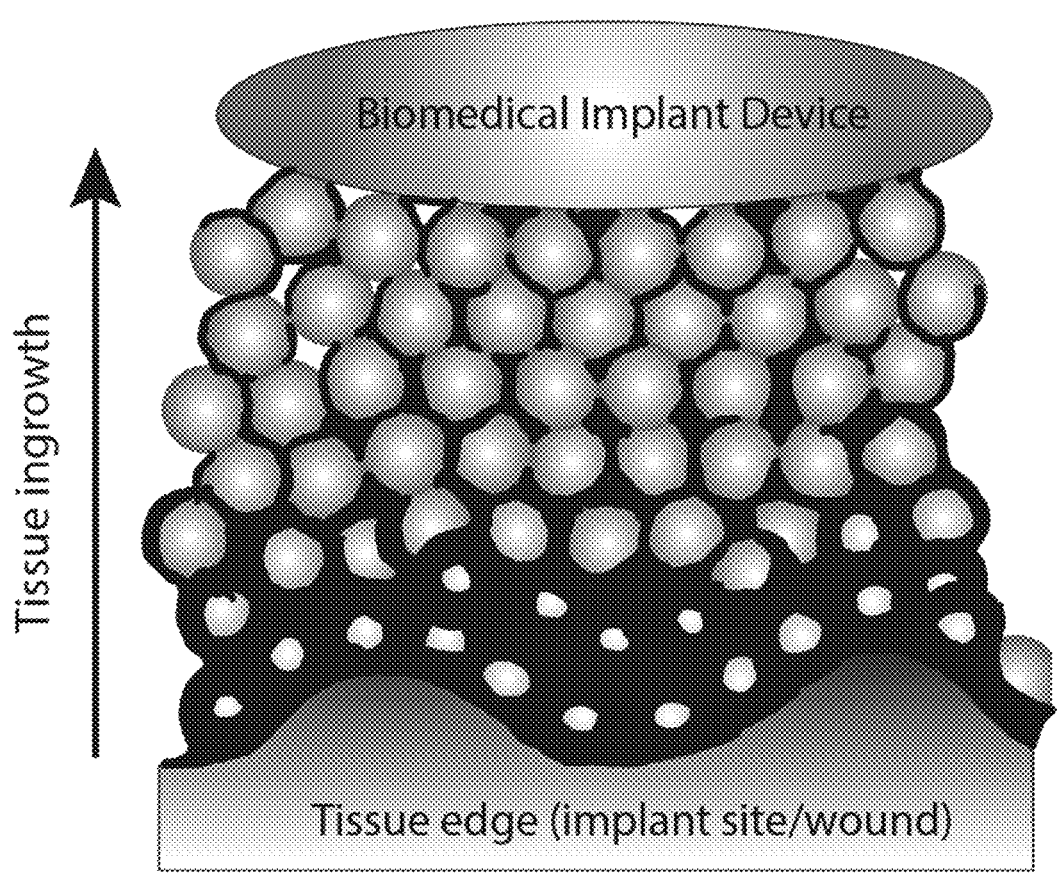
FIG. 2 shows an exemplary wound, wherein a microporous scaffold has been formed between the medical implant and the surrounding tissue. The presence of interconnected pores, with or without cells that have migrated into the microporous scaffold, are represented by the black color between the silver spherical shapes, the latter of which represent the microgel particles.

Medical devices, such as implants and surgical instruments, are used for a wide variety of applications. Use of these tools can be complicated by inflammation, infection, pain, scarring, and inability of an implant site or surgical site to heal or repair. The microporous gel systems disclosed herein may initially exist in a fluidic state, as a composition of flowable microgel particles in a solution. For example, in certain application, this solution is applied to the implant or surgical site in a subject before, after and/or concurrently with application of the medical device to improve the health and healing of the site. Due to its fluidic nature, the microporous gel system completely fills any space that may remain in the site surrounding the medical device. Once the solution and medical device are applied, an annealing agent is added or activated to anneal the microgel particles, creating a microporous scaffold. The microporous gel systems disclosed herein, unlike other porous gel systems, do not require porogens to produce the micropores of the scaffold. Instead, the microporous gel systems disclosed herein comprise microgel particles that are annealed and/or crosslinked together while allowing for micropores to form between the microgel particles. Cells of the subject can, in certain applications, migrate through the micropores of the scaffold aiding in healing the site. By way of non-limiting example, healing the site may comprise vascularizing, depositing extracellular matrix, and producing proteins and enzymes that aid in healing. In addition to aiding healing, the annealed scaffold may act as a functional glue to maintain the medical device placement in the site. The nature of the fluid-to-scaffold property in vivo provides a custom fit for the device; for example, a one-size-fits-all for the medical device. The microporous gel systems may also comprise therapeutic agents to treat the site for inflammation, pain or infection. The therapeutic agents include, but are not limited to, anti-inflammatory agents, analgesics, and antimicrobials. Therapeutic agents specific to the site may also be used. For example, the medical implant may be a cardiac pacemaker, and a therapeutic agent specific to the implantation site may be an antimicrobial agent.

Certain Terminologies

Unless defined otherwise, all technical and scientific terms used herein have the same meaning as is commonly understood by one of skill in the art to which the claimed subject matter belongs. It is to be understood that the foregoing general description and the following examples are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. For example, "about 5 μL" means "about 5 μL" and also "5 μL." Generally, the term "about" includes an amount that would be expected to be within experimental error. The term "about" includes values that are within 10% less to 10% greater of the value provided. For example, "about 50%" means "between 45% and 55%." Also, by way of example, "about 30" means "between 27 and 33."

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human.

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value. A p-value of less than 0.05 is considered statistically significant.

As used herein, the term "treating" and "treatment" refers to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission (whether partial or total), whether detectable or undetectable. Alternatively, treatment is "effective" if the progression of a disease is reduced or halted. Those in need of treatment include those already diagnosed with a disease or condition, as well as those likely to develop a disease or condition due to genetic susceptibility or other factors which contribute to the disease or condition, such as a non-limiting example, weight, diet and health of a subject are factors which may contribute to a subject likely to develop diabetes mellitus. Those in need of treatment also include subjects in need of medical or surgical attention, care, or management.

Without further elaboration, it is believed that one skilled in the art, using the preceding description, can utilize the present invention to the fullest extent. The following examples are illustrative only, and not limiting of the remainder of the disclosure in any way whatsoever.

Systems

Provided herein are systems comprising a microporous gel system disclosed herein and a medical device disclosed herein. Microporous gel systems disclosed herein generally comprise a collection of flowable microgel particles and at least one annealing component. Microporous gel systems disclosed herein may comprise an annealing agent that links the flowable microgel particles together via the annealing component to form a stabilized scaffold. The microporous gel system may also simply be referred to herein as a "gel" or "hydrogel." Alternatively, or additionally, microporous gel systems disclosed herein may comprise a crosslinker that links the flowable microgel particles together via the annealing component. In general, resulting stabilized scaffolds comprise interstitial spaces therein. By way of non-limiting example, medical devices include cardiac implantable electronic devices and neural implantable electronic devices.

Systems disclosed herein may comprise a container to contain the microporous gel system, e.g., a bottle, tube, syringe, syringe barrel, or plastic bag. Systems disclosed herein may comprise an application device for applying the microporous gel system to a tissue defect. The container may be the application device, may be used with the application device, or may be used instead of the application device.

The collection of flowable microgel particles and an annealing agent may be stored in a single container. The collection of flowable microgel particles and annealing agent may be administered from a single container. Additional components of the systems, such as crosslinkers, therapeutic agents, therapeutic agent releasing agents, nanoparticles, and cell adhesive peptides, including all those disclosed herein, may be stored or administered from the single container or a separate container.

The collection of flowable microgel particles may be stored in a first container and the annealing agent may be stored in a second container. The collection of flowable microgel particles may be administered from a first container and the annealing agent may be administered from a second container.

In some instances, a first portion of the flowable microgel particles is administered from a first container and a second portion of the flowable microgel particles is administered from a second container. Contents of first and second containers may be administered sequentially. Contents of first and second containers may be administered simultaneously.

Any one of the systems disclosed herein may comprise an application device to apply the microporous gel system to a tissue of a subject. By way of non-limiting example, the application device may comprise a syringe, a spatula, a squeezable tube, a cannula, or any combination thereof. The application device may comprise a needle. The needle may be blunt so as to avoid damaging or piercing a tissue. The microporous gel may have a viscosity low enough before annealing to be sprayed on the tissue of the subject. Thus, the application device may comprise a spray mechanism.

Containers and application devices disclosed herein encompass a wide range of volumes that are suitable for application to a wound, surgical or implant site receiving a medical device. Volumes include, but are not limited to, about 0.1 mL to about 0.5 L, about 0.1 mL to about 0.2 L, about 0.1 mL to about 0.1 L, about 0.1 mL to about 75 mL, about 0.1 mL to about 60 mL, about 0.1 mL to about 50 mL, about 0.1 mL to about 25 mL, about 0.1 mL to about 20 mL, about 0.1 mL to about 10 mL, about 1 mL to about 0.5 L, about 1 mL to about 0.2 L, about 1 mL to about 1 L, about 1 mL to about 75 mL, about 1 mL to about 60 mL, about 1 mL to about 50 mL, about 1 mL to about 25 mL, about 1 mL to about 20 mL, or about 1 mL to about 10 mL.

Microporous Gel Systems

Provided herein are methods and systems for treating a condition in a subject in need thereof, comprising administering to the subject a microporous gel system disclosed herein. Microporous gel systems may also simply be referred to herein as a "gel" or "hydrogel." The microporous gel systems disclosed herein may take different forms, and, unless otherwise specified, the various terms that are used to reference these forms, such as microporous gel scaffold, stabilized scaffold, collection of flowable microgel particles, and microporous gel, may be used interchangeably herein. The microporous gel system may be administered to a site in the subject before, after or simultaneously with application of an implant or surgical device disclosed herein to the site. The microporous gel systems disclosed herein may comprise a collection of flowable microgel particles comprising a backbone polymer and an annealing component. Flowable microgel particles may also be referred to herein simply as "microgel particles." Methods of synthesizing flowable microgel particles are disclosed herein.

Flowable Microgel Particles

The flowable microgel particles may be spherical particles or roughly spherical particles. The flowable microgel particles may be irregular shaped or polygonal shaped. The flowable microgel particles may have a diameter or dimension (e.g., length, width, height, axis). The flowable microgel particles may have an average diameter or dimension of about 10 micrometers. The flowable microgel particles may have an average diameter or dimension of about 15 micrometers. The flowable microgel particles may have an average diameter or dimension of about 25 micrometers. The flowable microgel particles may have a diameter or dimension of about 50 micrometers. The flowable microgel particles may have an average diameter or dimension of about 100 micrometers. The flowable microgel particles may have an average diameter or dimension of about 150 micrometers. The flowable microgel particles may have an average diameter or dimension of about 200 micrometers. The flowable microgel particles may have a diameter or dimension within the range of about 10 micrometers to about 500 micrometers. The flowable microgel particles may have a diameter or dimension within the range of about 10 micrometers to about 200 micrometers. The flowable microgel particles may have a diameter or dimension within the range of about 15 micrometers to about 200 micrometers. The flowable microgel particles may have a diameter or dimension within the range of about 15 micrometers to about 150 micrometers. The flowable microgel particles may have a diameter or dimension within the range of about 30 micrometers to about 100 micrometers.

The flowable microgel particles may have an average diameter or dimension of 10 micrometers. The flowable microgel particles may have an average diameter or dimension of 15 micrometers. The flowable microgel particles may have an average diameter or dimension of 25 micrometers. The flowable microgel particles may have a diameter or dimension of 50 micrometers. The flowable microgel particles may have an average diameter or dimension of 100 micrometers. The flowable microgel particles may have an average diameter or dimension of 150 micrometers. The flowable microgel particles may have an average diameter or dimension of 200 micrometers. The flowable microgel particles may have a diameter or dimension within the range of 10 micrometers to 500 micrometers. The flowable microgel particles may have a diameter or dimension within the range of 10 micrometers to 200 micrometers. The flowable microgel particles may have a diameter or dimension within the range of 15 micrometers to 200 micrometers. The flowable microgel particles may have a diameter or dimension within the range of 15 micrometers to 150 micrometers. The flowable microgel particles may have a diameter or dimension within the range of 30 micrometers to 100 micrometers. The diameter or dimension of the flowable microgel particles may depend on a component or property of a solvent in which they are dispersed before the microporous gel system becomes a stabilized scaffold. The solvent may be water. The solvent may be isotonic with blood of the subject. The solvent may be a saline solution. The solvent may be a buffered saline solution. In certain embodiments, the solvent is acidic. The solvent may have a pH of about 4 to about 7. The solvent may have a pH of about 3, about 4, about 5, about 6, or about 7. In certain embodiments, the solvent is alkaline. The solvent may have a pH greater than 7. The solvent may have a pH of about 8, about 9 or about 10.

Backbone Polymers

Flowable microgel particles disclosed herein comprise at least one backbone polymer. By way of non-limiting example, the backbone polymer may comprise a polymer selected from poly(ethylene glycol), hyaluronic acid, polyacrylamide, or polymethacrylate. The backbone polymer of the flowable microgel particles disclosed herein may comprise a hydrophilic polymer, amphiphilic polymer, synthetic or natural polymer (e.g., poly(ethylene glycol) (PEG), poly(propylene glycol), poly(hydroxyethylmethacrylate), hyaluronic acid (HA), gelatin, fibrin, chitosan, heparin, heparan, and synthetic versions of HA, gelatin, fibrin, chitosan, heparin, or heparan). The backbone polymer of the flowable microgel particles disclosed herein may be made from any natural (e.g., modified HA) or synthetic polymer (e.g., PEG) capable of forming a hydrogel. The backbone polymer may comprise a natural polymer containing nitrogen, such as proteins and derivatives, including crosslinked or modified gelatins, and keratins. The backbone polymer may comprise a vinyl polymer such as poly(ethyleneglycol) acrylate, poly(ethyleneglycol) methacrylate, poly(ethyleneglycol) vinyl sulfone, poly(ethyleneglycol) maleimide, poly(ethyleneglycol) norbornene, poly(ethyleneglycol) allyl. The backbone polymer may comprise a polyacrylamide or a polymethacrylates. The backbone polymer may comprise a polyester, a polyamide, a polyurethane, and a mixture or copolymer thereof. The backbone polymer may comprise a graft copolymer obtained by initializing polymerization of a synthetic polymer on a preexisting natural polymer.

The flowable microgel particles disclosed herein may, alternatively or additionally to the backbone polymer, comprise a suitable support material. The support material may be suitable for most tissue engineering/regenerative medicine applications. The support material is generally biocompatible and preferably biodegradable. Examples of suitable support material include, but are not limited to, natural polymeric carbohydrates and their synthetically modified, crosslinked, or substituted derivatives, such as gelatin, agar, agarose, crosslinked alginic acid, chitin, substituted and crosslinked guar gums, cellulose esters, especially with nitrous acids and carboxylic acids, mixed cellulose esters, and cellulose ethers; natural polymers containing nitrogen, such as proteins and derivatives, including crosslinked or modified gelatins, and keratins; vinyl polymers such as poly(ethyleneglycol)acrylate/methacrylate/vinyl sulfone/maleimide/norbornene/allyl, polyacrylamides, polymethacrylates, copolymers and terpolymers of the above polycondensates, such as polyesters, polyamides, and other polymers, such as polyurethanes; and mixtures or copolymers of the above classes, such as graft copolymers obtained by initializing polymerization of synthetic polymers on a preexisting natural polymer. A variety of biocompatible and biodegradable polymers are available for use in therapeutic applications; examples include: polycaprolactone, polyglycolide, polylactide, poly(lactic-co-glycolic acid) (PLGA), and poly-3-hydroxybutyrate.

The backbone polymer may be present at a concentration of about 1% w/v to about 15% w/v of the microporous gel. The backbone polymer may be present at a concentration of 1% w/v to 15% w/v of the microporous gel. The backbone polymer may be present at a concentration of about 2% w/v to about 10% w/v of the microporous gel. The backbone polymer may be present at a concentration of 2% w/v to 10% w/v of the microporous gel. The backbone polymer may be present at a concentration of about 1% w/v of the microporous gel. The backbone polymer may be present at a concentration of about 2% w/v of the microporous gel. The backbone polymer may be present at a concentration of about 3% w/v of the microporous gel. The backbone polymer may be present at a concentration of about 4% w/v of the microporous gel. The backbone polymer may be present at a concentration of about 5% w/v of the microporous gel. The backbone polymer may be present at a concentration of about 6% w/v of the microporous gel. The backbone polymer may be present at a concentration of about 7% w/v of the microporous gel. The backbone polymer may be present at a concentration of about 8% w/v of the microporous gel. The backbone polymer may be present at a concentration of about 9% w/v of the microporous gel. The backbone polymer may be present at a concentration of about 10% w/v of the microporous gel. The backbone polymer may be present at a concentration of about 11% w/v of the microporous gel.

The backbone polymer may be present at a concentration of 12% w/v of the microporous gel.

Annealing Components

Microporous gel systems disclosed herein generally comprise at least one annealing component. In many cases, annealing components are merely functional groups comprising a reactive moiety. By way of non-limiting example, the reactive moiety may comprise at least one functional group selected from a vinyl sulfone, thiol, amine, imidazole, aldehyde, ketone, hydroxyl, azide, alkyne, vinyl, alkene, maleimide, carboxyl, N-hydroxysuccinimide (NHS) ester, isocyanate, isothiocyanate, hydroxylamine, and thione. The annealing component may comprise a vinyl group. The annealing component may comprise a free cysteine. The annealing component may comprise a thiol. The annealing component may comprise an amine. The annealing component may comprise a reactive moiety. The reactive moiety may comprise a catechol (e.g., L-DOPA, dopamine). The reactive moiety may comprise sialic acid (e.g. neuraminic acid). The reactive moiety may comprise boronic acid (e.g., 3-aminophenylboronic acid). The reactive moiety may comprise a molecular cage (e.g., cyclodextrin, cucurbituril, calixarene, pillararene, crown ether, cavitand, cryptands carcerand). The reactive moiety may comprise adamantane. The reactive moiety may comprise biotin. The reactive moiety may comprise streptavidin.

Annealing components disclosed herein may include large biological molecules. The annealing component may comprise a peptide. The annealing component may consist essentially of a peptide. In some instances, the annealing component comprises a nucleic acid. The annealing component may consist essentially of a nucleic acid. The annealing component may comprise a protein. The annealing component may comprise an antibody or antigen binding antibody fragment. The annealing component may comprise an epitope. The annealing component may comprise an enzymatic substrate. The annealing component may be provided by the subject. By way of non-limiting example, the annealing component may comprise a transglutaminase substrate (e.g., fibrin). A non-limiting example of a transglutaminase is enzyme Factor XIII. In this case, endogenous Factor XIII acts as an annealing agent on fibrin to form γ-glutamyl-ϵ-lysyl amide cross links between fibrin molecules. Another non-limiting example of an annealing component is a collagen peptide. The collagen peptide may be a K peptide (K-peptide: Ac-FKGGERCG-NH2). The collagen peptide may be a Q peptide (Q peptide: Ac-NQEQVSPLG-GERCG-NH2). In some instances, K peptide and Q peptide serve as annealing components as well as cell adhesive peptides.

Crosslinkers

Microporous gel systems disclosed herein may comprise at least one crosslinker. In some instances, at least a portion of the flowable microgel particles comprise a crosslinker. In some instances, at least a portion of the flowable microgel particles are interlinked by a crosslinker. The crosslinker may be an intracrosslinker, providing intracrosslinking (intracrosslinks) within the flowable microgel particles. The crosslinker may be an intercrosslinker, providing intercrosslinking (intercrosslinks) between flowable microgel particles. The crosslinker may be an extracrosslinker, providing extracrosslinking (extracrosslinks) between the flowable microgel particles and a substrate. The substrate may be tissue. The substrate may be a medical device.

Generally, crosslinkers disclosed herein comprise at least two functional groups. The crosslinker may comprise a first functional group and a second functional group. The first functional group and the second functional group may be the same. The first functional group and the second functional group may be different. Crosslinkers disclosed herein may also be referred to as multifunctionalized crosslinkers.

Crosslinkers may be degradable. Crosslinkers disclosed herein may comprise a peptide. Crosslinkers disclosed herein may comprise an amino acid. Crosslinkers may comprise a non-peptide polymer. Degradable crosslinkers may also be random sequences, Omi target sequences, Heat-Shock Protein target sequences. The crosslinker may comprise an amino acid having D chirality. The crosslinker may comprise an amino acid having L chirality. Crosslinkers may comprise hydrolytically degradable natural and synthetic polymers consisting of the same backbones listed above (e.g., heparin, alginate, poly(ethyleneglycol), polyacrylamides, polymethacrylates, copolymers and terpolymers of the listed polycondensates, such as polyesters, polyamides, and other polymers, such as polyurethanes). The crosslinker may be synthetically manufactured or naturally isolated. The crosslinker may comprise DNA oligonucleotides with sequences corresponding to: restriction enzyme recognition sequences, CpG motifs, Zinc finger motifs, CRISPR or Cas-9 sequences, Talon recognition sequences, and transcription factor-binding domains. The crosslinker may be activated on at least two ends by a reactive group, defined as a chemical group allowing the crosslinker to participate in the crosslinking reaction to form a polymer network or gel (intracrosslinking within particles) or to anneal particles together (intercrosslinking between particles) or to anneal the particles to a substrate (extracrosslinking between particles and a substrate), where these functionalities can include: cysteine amino acids, synthetic and naturally occurring thiol-containing molecules, carbene-containing groups, vinyl-containing groups, activated esters, acrylates, norbornes, primary amines, hydrazides, phosphenes, azides, epoxy-containing groups, SANPAH containing groups, and diazirine containing groups. In some instances, flowable microgel particles themselves may act as crosslinkers.

Intracrosslinkers

In some instances, intracrosslinkers disclosed herein are crosslinkers that participate in the crosslinking reaction to form a polymer network or gel or microgel. In some instances, intracrosslinkers disclosed herein are crosslinkers that participate in the crosslinking reaction to form microgel particles. Often, the intracrosslinker is functionalized with two or more functional groups. By way of non-limiting example, the functional groups of the intracrosslinker may be selected from a vinyl sulfone, a thiol, an amine, an imidazole, an aldehyde, a ketone, a hydroxyl, an azide, an alkyne, a vinyl, an alkene, a maleimide, a carboxyl, a N-Hydroxysuccinimide (NHS) ester, an isocyanate, an isothiocyanate, ahydroxylamine, and a thione. The intracrosslinker may be homofunctional (same functional groups) or heterofunctional (different functional groups). Examples of crosslinking reactions carried out by intracrosslinker include, but are not limited to, Michael addition, amide bond coupling, "click" chemistry (e.g. Diels-Alder cycloaddition, Huisgen 1,3-dipolar cycloaddition), reductive amination, carbamate linkage, ester linkage, thioether linkage, disulfide bond, hydrazone bond, oxime coupling, thiourea coupling. By way of non-limiting example, an intracrosslinker may be a matrix metalloprotease (MMP)-degradable crosslinker. Examples of MMP-degradable crosslinkers are synthetically manufactured or naturally isolated peptides with sequences corresponding to MMP-1 target substrate, MMP-2 target substrate, MMP-9 target substrates. An intracrosslinker may be a dithiol-poly(ethylene glycol). An intracrosslinker may be a diamine-poly(ethylene glycol). An intracrosslinker may be a diamine-poly(ethylene glycol). An intracrosslinker may be a 4-ARM-poly(ethylene glycol)-thiol. An intracrosslinker may be a 4-ARM-poly(ethylene glycol)-vinyl sulfone. An intracrosslinker may be a 8-ARM-poly(ethylene glycol)-thiol. An intracrosslinker may be a 8-ARM-poly(ethylene glycol)-vinyl sulfone.

Intercrosslinkers

In some instances, intercrosslinkers disclosed herein that participate in the crosslinking reaction between particles to anneal particles together. Often, the intercrosslinker is functionalized with two or more functional groups. By way of non-limiting example, the functional groups of the intercrosslinker may be selected from a vinyl sulfone, a thiol, an amine, an imidazole, an aldehyde, a ketone, a hydroxyl, an azide, an alkyne, a vinyl, an alkene, a maleimide, a carboxyl, a N-Hydroxysuccinimide (NHS) ester, an isocyanate, an isothiocyanate, ahydroxylamine, and a thione. The multifunctionalized crosslinker may be homofunctional (combination of same functional groups) or heterofunctional (combination of different functional groups). Examples of crosslinking reactions carried out by intercrosslinker include, but are not limited to, Michael addition, amide bond coupling, "click" chemistry (e.g. Diels-Alder cycloaddition, Huisgen 1,3-dipolar cycloaddition), reductive amination, carbamate linkage, ester linkage, thioether linkage, disulfide bond, hydrazone bond, oxime coupling, thiourea coupling. An intercrosslinker may be a dithiol-poly(ethylene glycol). An intercrosslinker may be a diamine-poly(ethylene glycol). An intercrosslinker may be a dithiol-oligo(ethylene glycol). An intercrosslinker may be a diamine-oligo(ethylene glycol). An intercrosslinker may be an ethylenediamine. An intercrosslinker may be a butylenediamine.

Extracrosslinkers

In some instances, extracrosslinkers disclosed herein participate in the crosslinking reaction between particles and a substrate (particle-substrate annealing). By way of non-limiting example, the functional groups of the extracrosslinker may be selected from a vinyl sulfone, a thiol, an amine, an imidazole, an aldehyde, a ketone, a hydroxyl, an azide, an alkyne, a vinyl, an alkene, a maleimide, a carboxyl, a N-Hydroxysuccinimide (NHS) ester, an isocyanate, an isothiocyanate, ahydroxylamine, and a thione. The extracrosslinker may be homofunctional (same functional groups) or heterofunctional (different functional groups). Examples of crosslinking reactions carried out by extracrosslinkers disclosed herein include, but are not limited to, Michael addition, amide bond coupling, "click" chemistry (e.g. Diels-Alder cycloaddition, Huisgen 1,3-dipolar cycloaddition), reductive amination, carbamate linkage, ester linkage, thioether linkage, disulfide bond, hydrazone bond, oxime coupling, thiourea coupling. By way of non-limiting example, an extracrosslinker may be a matrix metalloprotease (MMP)-degradable crosslinker. Examples of MMP-degradable crosslinkers are synthetically manufactured or naturally isolated peptides with sequences corresponding to MMP-1 target substrate, MMP-2 target substrate, MMP-9 target substrates. An extracrosslinker may be a dithiol-poly(ethylene glycol). An extracrosslinker may be a diamine-poly(ethylene glycol). An extracrosslinker may be a diamine-poly(ethylene glycol). An extracrosslinker may be a 4-ARM-poly(ethylene glycol)-thiol. An extracrosslinker may be a 4-ARM-poly(ethylene glycol)-vinyl sulfone. An intracrosslinker may be a 8-ARM-poly(ethylene glycol)-thiol. An extracrosslinker may be a 8-ARM-poly(ethylene glycol)-vinyl sulfone.

Annealing Agents

Provided herein are microporous gel systems comprising at least one annealing agent disclosed herein. The annealing agent may be a crosslinking agent disclosed herein. The annealing agent may comprise a photoinitiator. By way of non-limiting example, the photoinitiator may be Eosin Y. The annealing agent may be triethanolamine. The annealing agent may be a transglutaminase enzyme. The annealing agent may be enzyme Factor XIII. The annealing agent may comprise a free radical transfer agent. The annealing agent may comprise an electron transfer agent. Examples of additional and alternative annealing agents, by way of non-limiting example, include active esters and nucleophiles, catechols that crosslink upon oxidation, and other redox sensitive molecules.

Crosslinking Agents

Microporous gel systems may comprise a crosslinking agent. The crosslinking agent may be an intracrosslinking agent for providing intracrosslinks within flowable microgel particles. In general, intracrosslinking agents do not form crosslinks (e.g., they are not part of the bonds), but instead initiate intracrosslinking reactions between intracrosslinkers. The crosslinking agent may be an intercrosslinking agent for providing intercrosslinks between flowable microgel particles. The crosslinking agent may be an extracrosslinking agent for providing extracrosslinks between flowable microgel particles and a substrate. A crosslinking agent may comprise a reducing agent. Non-limiting examples of reducing agents are dithiothreitol, dithioerythritol, L-glutathione, and tris (2-carboxyethyl) phosphine hydrochloride. Crosslinking agents disclosed herein may comprise an oxidizing agent. Non-limiting examples of oxidizing agents are horseradish peroxidase (HRP), sodium periodate, and silver nitrate. Crosslinking agents disclosed herein may comprise a metal complexing agent. Crosslinking agents disclosed herein may comprise a catalyst. The crosslinking agent may be a base. Non-limiting examples of bases are triethylamine, triethanolamine, 4-dimethylaminopyridine, triphenylphosphine. The crosslinking agent may induce self-crosslinking of the annealing components present on the flowable microgel particles. Resulting crosslinkages, by way of non-limiting example, may comprise at least one of a covalent bond, a coordination complex, a hydrogen bond, an electrostatic interaction, a cation-π interaction, a π-π stacking, and a van der Waals interaction.

Cell Adhesive Peptides

Microporous gel systems may comprise a cell adhesive peptide disclosed herein. The flowable microgel particles may comprise a cell adhesive peptide. The cell adhesive peptide may be any peptide that promotes adherence of a cell to the microgel particles. The cell adhesive peptide may be at least a portion of an extracellular matrix protein. The cell adhesive peptide may be at least a portion of a collagen. The cell adhesive peptide may be at least a portion of a fibronectin. The cell adhesive peptide may be an integrin. The cell adhesive peptide may be a ligand to a receptor expressed on the cell. The cell adhesive peptide may be a cluster of differentiation (CD) protein. The cell adhesive peptide may be a naturally-occurring peptide. The cell adhesive peptide may be a synthetic peptide. The cell adhesive peptide may be homologous to the naturally-occurring peptide. The cell adhesive peptide may be at least about 70% homologous to a naturally-occurring peptide. The cell adhesive peptide may be at least about 80% homologous to a naturally-occurring peptide. The cell adhesive peptide may be at least about 90% homologous to a naturally-occurring peptide. The cell adhesive peptide may be at least 70% homologous to a naturally-occurring peptide. The cell adhesive peptide may be at least 80% homologous to a naturally-occurring peptide. The cell adhesive peptide may be at least 90% homologous to a naturally-occurring peptide. The cell adhesive peptide may be on a surface of the microgel particle. By way of non-limiting example, the cell adhesive peptide may comprise tripeptide Arginine-Glycine-Aspartate (RGD). The cell adhesive peptide may comprise K peptide (K peptide: Ac-FKGGERCG-NH2). The cell adhesive peptide may comprise Q peptide (Q peptide: Ac-NQEQVSPLGGERCG-NH2).

Microporous Scaffolds

As one of skill in the art would understand from the instant disclosure, microporous gel systems, or components thereof, as disclosed herein, may be initially fluidic in nature and eventually become a non-fluidic, microporous scaffold that provide a buffer between a medical device and a tissue. The non-fluidic, microporous scaffold may be referred to herein simply as a "microporous scaffold." The microporous scaffold may be flexible or compressible, with a foam or sponge-like quality. The microporous scaffold may be more rigid than a foam or sponge, in order to provide more support to an implanted medical device. The gel before annealing may have a compressive modulus (mechanical stiffness) of about 200-1000 Pa. The gel before annealing may have a compressive modulus (mechanical stiffness) of about 200-500 Pa. The gel before annealing may have a compressive modulus (mechanical stiffness) of about 500-1000 Pa. Once annealed, the gel may have a compressive modulus of about 1,500 Pa to about 200,000 Pa. Once annealed, the gel may have a compressive modulus of about 1,500 Pa to about 10,000 Pa. Once annealed, the gel may have a compressive modulus of about 10,000 Pa to about 50,000 Pa. Once annealed, the gel may have a compressive modulus of about 50,000 Pa to about 125,000 Pa. Once annealed, the gel may have a compressive modulus of about 125,000 Pa to about 200,000 Pa.

The microporous scaffold may be non-fluidic due to reactions that take place during or after the application of the microporous gel system components. The reactions may result in production of a covalent bond between two or more flowable microgel particles. The reactions may result in production of a covalent bond between two or more annealing components disclosed herein. Such a microporous scaffold may be referred to herein as a "stabilized scaffold." By way of non-limiting example, reactions that may result in a covalent bond include Michael addition, amide bond coupling, "click" chemistry reactions (e.g. Diels-Alder cycloaddition, Huisgen 1,3-dipolar cycloaddition), reductive amination, carbamate linkage, ester linkage, thioether linkage, oxime coupling, and thiourea coupling. Alternatively or additionally, reactions may result in production of a non-covalent bond between two or more flowable microgel particles. By way of non-limiting example, reactions that may result in a non-covalent bond include electrostatic interactions, hydrogen bonding, cation-π, π-π stacking, metal-ligand binding, and van der Waals interactions.

Microporous scaffolds disclosed herein may comprise at least one of a bond, a linkage, an interaction, a coupling and a connection between flowable microgel particles. In some instances, the bond, linkage, interaction, coupling or connection is between two annealing components. In some instances, the bond, linkage, interaction or connection is between an annealing component and a functional group on a backbone polymer of a flowable microgel particle. In some instances, the bond, linkage, interaction, coupling or connection is between two functional groups on the backbone polymers two flowable microgel particles. In some instances, the bond, linkage, interaction, coupling or connection is between a crosslinker and a functional group on a backbone polymer of a flowable microgel particle. In some instances, the bond, linkage, interaction, coupling or connection is between a crosslinker and an annealing component. In some instances, the bond is a covalent bond. In some instances, the bond is a non-covalent bond. In some instances, the bond is selected from an amide bond, an imine bond, an ester bond, a C—C bond through Michael addition, a disulfide bond, a hydrazone bond, a hydrogen bond, and a metal ligand bond. In some instances, the ester bond comprises a cyclic boronate ester. In some instances, the linkage is selected from a carbamate linkage, an ester linkage, and a thioether linkage. In some instances, the coupling is selected from an oxime coupling, and a thiourea coupling. In some instances, the interaction is selected from an electrostatic interaction and a van der Waals interaction. In some instances, the bond, linkage, interaction, coupling or connection is a result of a reaction between two functional groups. Non-limiting examples of such functional groups include a vinyl sulfone, a thiol, an amine, an imidazole, an aldehyde, a ketone, a hydroxyl, an azide, an alkyne, a vinyl, an alkene, a maleimide, a carboxyl, a N-Hydroxysuccinimide (NHS) ester, an isocyanate, an isothiocyanate, a hydroxylamine, a thione.

The interstitial spaces within the stabilized scaffold of microgel particles may occupy about 10% of the total volume of the stabilized scaffold. The interstitial spaces within the stabilized scaffold of microgel particles may occupy about 20% of the total volume of the stabilized scaffold. The interstitial spaces within the stabilized scaffold of microgel particles may occupy about 30% of the total volume of the stabilized scaffold. The interstitial spaces within the stabilized scaffold of microgel particles may occupy about 40% of the total volume of the stabilized scaffold. The interstitial spaces within the stabilized scaffold of microgel particles may occupy about 50% of the total volume of the stabilized scaffold. The interstitial spaces within the stabilized scaffold of microgel particles may occupy about 60% of the total volume of the stabilized scaffold. The interstitial spaces within the stabilized scaffold of microgel particles may occupy about 70% of the total volume of the stabilized scaffold. The interstitial spaces within the stabilized scaffold of microgel particles may occupy 10% of the total volume of the stabilized scaffold. The interstitial spaces within the stabilized scaffold of microgel particles may occupy 20% of the total volume of the stabilized scaffold. The interstitial spaces within the stabilized scaffold of microgel particles may occupy 30% of the total volume of the stabilized scaffold. The interstitial spaces within the stabilized scaffold of microgel particles may occupy 40% of the total volume of the stabilized scaffold. The interstitial spaces within the stabilized scaffold of microgel particles may occupy 50% of the total volume of the stabilized scaffold. The interstitial spaces within the stabilized scaffold of microgel particles may occupy 60% of the total volume of the stabilized scaffold. The interstitial spaces within the stabilized scaffold of microgel particles may occupy 70% of the total volume of the stabilized scaffold.

The interstitial spaces within the stabilized scaffold of microgel particles may occupy about 80% to about 70% of the total volume of the stabilized scaffold. The interstitial spaces within the stabilized scaffold of microgel particles may occupy about 75% to about 70% of the total volume of the stabilized scaffold.

The interstitial spaces within the stabilized scaffold of microgel particles may occupy about 5% to about 70% of the total volume of the stabilized scaffold. The interstitial spaces within the stabilized scaffold of microgel particles may occupy about 5% to about 65% of the total volume of the stabilized scaffold. The interstitial spaces within the stabilized scaffold of microgel particles may occupy about 5% to about 55% of the total volume of the stabilized scaffold. The interstitial spaces within the stabilized scaffold of microgel particles may occupy about 5% to about 50% of the total volume of the stabilized scaffold. The interstitial spaces within the stabilized scaffold of microgel particles may occupy about 5% to about 45% of the total volume of the stabilized scaffold. The interstitial spaces within the stabilized scaffold of microgel particles may occupy about 5% to about 40% of the total volume of the stabilized scaffold.

The interstitial spaces within the stabilized scaffold of microgel particles may occupy 5% to 70% of the total volume of the stabilized scaffold. The interstitial spaces within the stabilized scaffold of microgel particles may occupy 5% to 65% of the total volume of the stabilized scaffold. The interstitial spaces within the stabilized scaffold of microgel particles may occupy 5% to 55% of the total volume of the stabilized scaffold. The interstitial spaces within the stabilized scaffold of microgel particles may occupy 5% to 50% of the total volume of the stabilized scaffold. The interstitial spaces within the stabilized scaffold of microgel particles may occupy 5% to 45% of the total volume of the stabilized scaffold. The interstitial spaces within the stabilized scaffold of microgel particles may occupy 5% to 40% of the total volume of the stabilized scaffold.

The interstitial spaces within the stabilized scaffold of microgel particles may occupy about 10% to about 80% of the total volume of the stabilized scaffold. The interstitial spaces within the stabilized scaffold of microgel particles may occupy about 10% to about 75% of the total volume of the stabilized scaffold. The interstitial spaces within the stabilized scaffold of microgel particles may occupy about 10% to about 70% of the total volume of the stabilized scaffold. The interstitial spaces within the stabilized scaffold of microgel particles may occupy about 10% to about 65% of the total volume of the stabilized scaffold. The interstitial spaces within the stabilized scaffold of microgel particles may occupy about 10% to about 55% of the total volume of the stabilized scaffold. The interstitial spaces within the stabilized scaffold of microgel particles may occupy about 10% to about 50% of the total volume of the stabilized scaffold. The interstitial spaces within the stabilized scaffold of microgel particles may occupy about 10% to about 45% of the total volume of the stabilized scaffold. The interstitial spaces within the stabilized scaffold of microgel particles may occupy about 10% to about 40% of the total volume of the stabilized scaffold.

The interstitial spaces within the stabilized scaffold of microgel particles may occupy 10% to 80% of the total volume of the stabilized scaffold. The interstitial spaces within the stabilized scaffold of microgel particles may occupy 10% to 75% of the total volume of the stabilized scaffold. The interstitial spaces within the stabilized scaffold of microgel particles may occupy 10% to 70% of the total volume of the stabilized scaffold. The interstitial spaces within the stabilized scaffold of microgel particles may occupy 10% to 65% of the total volume of the stabilized scaffold. The interstitial spaces within the stabilized scaffold of microgel particles may occupy 10% to 55% of the total volume of the stabilized scaffold. The interstitial spaces within the stabilized scaffold of microgel particles may occupy 10% to 50% of the total volume of the stabilized scaffold. The interstitial spaces within the stabilized scaffold of microgel particles may occupy 10% to 45% of the total volume of the stabilized scaffold. The interstitial spaces within the stabilized scaffold of microgel particles may occupy 10% to 40% of the total volume of the stabilized scaffold.

The interstitial spaces within the stabilized scaffold of microgel particles may occupy about 15% to about 80% of the total volume of the stabilized scaffold. The interstitial spaces within the stabilized scaffold of microgel particles may occupy about 15% to about 75% of the total volume of the stabilized scaffold. The interstitial spaces within the stabilized scaffold of microgel particles may occupy about 15% to about 70% of the total volume of the stabilized scaffold. The interstitial spaces within the stabilized scaffold of microgel particles may occupy about 15% to about 65% of the total volume of the stabilized scaffold. The interstitial spaces within the stabilized scaffold of microgel particles may occupy about 15% to about 55% of the total volume of the stabilized scaffold. The interstitial spaces within the stabilized scaffold of microgel particles may occupy about 15% to about 50% of the total volume of the stabilized scaffold. The interstitial spaces within the stabilized scaffold of microgel particles may occupy about 15% to about 45% of the total volume of the stabilized scaffold. The interstitial spaces within the stabilized scaffold of microgel particles may occupy about 15% to about 40% of the total volume of the stabilized scaffold.

The interstitial spaces within the stabilized scaffold of microgel particles may occupy 15% to 80% of the total volume of the stabilized scaffold. The interstitial spaces within the stabilized scaffold of microgel particles may occupy 15% to 75% of the total volume of the stabilized scaffold. The interstitial spaces within the stabilized scaffold of microgel particles may occupy 15% to 70% of the total volume of the stabilized scaffold. The interstitial spaces within the stabilized scaffold of microgel particles may occupy 15% to 65% of the total volume of the stabilized scaffold. The interstitial spaces within the stabilized scaffold of microgel particles may occupy 15% to 55% of the total volume of the stabilized scaffold. The interstitial spaces within the stabilized scaffold of microgel particles may occupy 15% to 50% of the total volume of the stabilized scaffold. The interstitial spaces within the stabilized scaffold of microgel particles may occupy 15% to 45% of the total volume of the stabilized scaffold. The interstitial spaces within the stabilized scaffold of microgel particles may occupy 15% to 40% of the total volume of the stabilized scaffold.

The interstitial spaces within the stabilized scaffold of microgel particles may occupy about 20% to about 80% of the total volume of the stabilized scaffold. The interstitial spaces within the stabilized scaffold of microgel particles may occupy about 20% to about 75% of the total volume of the stabilized scaffold. The interstitial spaces within the stabilized scaffold of microgel particles may occupy about 20% to about 70% of the total volume of the stabilized scaffold. The interstitial spaces within the stabilized scaffold of microgel particles may occupy about 20% to about 65% of the total volume of the stabilized scaffold. The interstitial spaces within the stabilized scaffold of microgel particles may occupy about 20% to about 55% of the total volume of the stabilized scaffold. The interstitial spaces within the stabilized scaffold of microgel particles may occupy about 20% to about 50% of the total volume of the stabilized scaffold. The interstitial spaces within the stabilized scaffold of microgel particles may occupy about 20% to about 45% of the total volume of the stabilized scaffold. The interstitial spaces within the stabilized scaffold of microgel particles may occupy about 20% to about 40% of the total volume of the stabilized scaffold.

The interstitial spaces within the stabilized scaffold of microgel particles may occupy 20% to 80% of the total volume of the stabilized scaffold. The interstitial spaces within the stabilized scaffold of microgel particles may occupy 20% to 75% of the total volume of the stabilized scaffold. The interstitial spaces within the stabilized scaffold of microgel particles may occupy 20% to 70% of the total volume of the stabilized scaffold. The interstitial spaces within the stabilized scaffold of microgel particles may occupy 20% to 65% of the total volume of the stabilized scaffold. The interstitial spaces within the stabilized scaffold of microgel particles may occupy 20% to 55% of the total volume of the stabilized scaffold. The interstitial spaces within the stabilized scaffold of microgel particles may occupy 20% to 50% of the total volume of the stabilized scaffold. The interstitial spaces within the stabilized scaffold of microgel particles may occupy 20% to 45% of the total volume of the stabilized scaffold. The interstitial spaces within the stabilized scaffold of microgel particles may occupy 20% to 40% of the total volume of the stabilized scaffold.

Microporous Gel System Stability

The microporous gel systems disclosed herein may have a shelf life of at least about six months. The microporous gel systems disclosed herein may have a shelf life of at least about seven months. The microporous gel systems disclosed herein may have a shelf life of at least about eight months. The microporous gel systems disclosed herein may have a shelf life of at least about nine months. The microporous gel systems disclosed herein may have a shelf life of at least about ten months. The microporous gel systems disclosed herein may have a shelf life of at least about eleven months. The microporous gel systems disclosed herein may have a shelf life of at least about one year. The microporous gel systems disclosed herein may have a shelf life of at least about fourteen months. The microporous gel systems disclosed herein may have a shelf life of at least about sixteen months. The microporous gel systems disclosed herein may have a shelf life of at least about eighteen months. The microporous gel systems disclosed herein may have a shelf life of at least about twenty months. The microporous gel systems disclosed herein may have a shelf life of at least about twenty-two months. The microporous gel systems disclosed herein may have a shelf life of at least about two years. The microporous gel systems disclosed herein may have a shelf life of at least about three years. The microporous gel systems disclosed herein may have a shelf life of at least about four years. The microporous gel systems disclosed herein may have a shelf life of at least about five years. The microporous gel systems disclosed herein may have a shelf life of at least six months. The microporous gel systems disclosed herein may have a shelf life of at least seven months. The microporous gel systems disclosed herein may have a shelf life of at least eight months. The microporous gel systems disclosed herein may have a shelf life of at least nine months. The microporous gel systems disclosed herein may have a shelf life of at least ten months. The microporous gel systems disclosed herein may have a shelf life of at least eleven months. The microporous gel systems disclosed herein may have a shelf life of at least one year. The microporous gel systems disclosed herein may have a shelf life of at least fourteen months. The microporous gel systems disclosed herein may have a shelf life of at least sixteen months. The microporous gel systems disclosed herein may have a shelf life of at least eighteen months. The microporous gel systems disclosed herein may have a shelf life of at least twenty months. The microporous gel systems disclosed herein may have a shelf life of at least twenty-two months. The microporous gel systems disclosed herein may have a shelf life of at least two years. The microporous gel systems disclosed herein may have a shelf life of at least three years. The microporous gel systems disclosed herein may have a shelf life of at least four years. The microporous gel systems disclosed herein may have a shelf life of at least five years.

The microporous gel systems disclosed herein, or components thereof, may be stable (e.g., have a shelf life) up to a temperature disclosed herein. The microporous gel systems disclosed herein, or components thereof, may be stable at up to a temperature when in a dissolved state, a fluidic state, a lyophilized state, or a dehydrated state. The microporous gel systems, or components thereof, may be stable at room temperature (about 25° C.). The microporous gel systems, or components thereof, may be stable at 25° C. The microporous gel systems, or components thereof, may be stable at about 25° C. to about 35° C. The microporous gel systems, or components thereof, may be stable at 25° C. to 35° C. The microporous gel systems, or components thereof, may be stable up to about 35° C., up to about 40° C., up to about 45° C., up to about 50° C., up to about 55° C., up to about 60° C., up to about 65° C., up to about 70° C., up to about 75° C., up to about 80° C., up to about 85° C., up to about 90° C., up to about 95° C., up to about 100° C., up to about 105° C., up to about 110° C., up to about 115° C., up to about 120° C., up to about 125° C., up to about 130° C., up to about 135° C., up to about 140° C., up to about 145° C., or up to about 150° C. The microporous gel systems, or components thereof, may be stable up to 35° C., up to 40° C., up to 45° C., up to 50° C., up to 55° C., up to 60° C., up to 65° C., up to 70° C., up to 75° C., up to 80° C., up to 85° C., up to 90° C., up to 95° C., up to 100° C., up to 105° C., up to 110*C, up to 115° C., up to 120° C., up to 125° C., up to 130° C., up to 135° C., up to 140° C., up to 145° C., or up to 150° C.

In some instances the stability or shelf life of the microporous gel system is increased by storing the microporous gel system, or a component thereof, below room temperature. Below room temperature may be about 20° C. to about −80° C., about 20° C. to about −20° C., about 20° C. to about 0° C., or about 20° C. to about 4° C. Below room temperature may be 20° C. to −80° C., 20° C. to −20° C., 20° C. to 0*C, or 20° C. to 4° C.

The microporous gel systems disclosed herein may have a shelf life of at least about one year at about 25° C. The microporous gel systems disclosed herein may have a shelf life of at least about one year at about 4° C. The microporous gel systems disclosed herein may have a shelf life of at least about one year at about 25° C. to about 35° C. The microporous gel systems disclosed herein may have a shelf life of at least about one year at about 4° C. to about 35° C. The microporous gel systems disclosed herein may have a shelf life of at least one year at 25° C. The microporous gel systems disclosed herein may have a shelf life of at least one year at 4° C. The microporous gel systems disclosed herein may have a shelf life of at least one year at 25° C. to 35° C.

The microporous gel systems disclosed herein may have a shelf life of at least one year at 4° C. to 35° C.

Medical Devices

Provided herein are methods and systems for treating a condition in a subject in need thereof, comprising administering to the subject a medical device disclosed herein. The medical device may be administered to a site in the subject before, after or simultaneously with application of a microporous gel system disclosed herein. The medical device may at least partially contain the microporous gel system. The medical device may be coated with the microporous gel system. Medical devices of many different shapes and sizes will be compatible with the microporous gel systems and stabilized scaffolds disclosed herein. Due to the initial fluidic nature of the microporous gel systems disclosed herein, the microporous gel system can coat portions or shapes of various medical devices before it becomes a stabilized scaffold. In some aspects, the stabilized scaffold is conformed to the shape and size of the device. In some aspects, the stabilized scaffold is adapted to the shape and size of the device. For the same reason that the microporous gel system is compatible with medical devices of many shapes and sizes (e.g., its fluidic nature), it is also compatible with implant sites of various shapes and sizes. Thus, the microporous gel system can adapt to, conform to, or custom fill various implant sites before it becomes the stabilized scaffold.

The medical device may be an implant. The implant may be a temporary implant. A temporary implant may be an implant that remains in the subject for more than one day, but not more than one week. A temporary implant may be an implant that remains in the subject for more than one week, but not more than one month. The implant may be a permanent implant. The implant may be an organ, artificial or donor. The implant may be a biomaterial, such as a mesh or fabric. The implant may be a printed device or tissue. As used herein, an implant is a medical device that is administered to a subject that remains in the subject after administration. The implant may be functional due to its physical structure. The implant may be functional due to an active function that it performs. The implant may comprise a glucose sensor. The implant may comprise a glucose dispenser. The implant may comprise a cell-based therapy delivered in a device (e.g., an islet cell transplantation).

The medical device may be a surgical device. As used herein, a surgical device is a structure that is used in the subject during a procedure, and that does not remain in the subject after the procedure. By way of non-limiting example, the surgical device may be a laser, scalpel or needle. The procedure may be a surgical procedure. The surgical procedure may comprise a modification of a tissue of the subject. The modification may comprise cutting the tissue. The procedure may be a non-surgical procedure. By way of non-limiting example, the non-surgical procedure may comprise insertion of a catheter or application of an ostomy device.

The medical device may be a vascular stent. The medical device may be a prosthetic device. The medical device may be an orthopedic implant, such as an artificial knee, meniscus, hip, elbow or portion thereof. The medical device may be a dental implant. The medical device may be a breast implant. The medical device may be a spinal implant, such as a screw, rod or artificial disc. The medical device may be an intra-uterine device. The medical device may be an ear tube. The medical device may be an artificial eye lens.

Provided herein are methods and systems for treating a heart arrhythmia in a subject in need thereof, comprising administering to the subject a Cardiac Implantable Electronic Device (CIED) and a microporous gel system disclosed herein. The CIED may be a device that is capable of correcting or improving an abnormal heart rhythm. CIEDs may include, but are not limited to, cardiac pacemakers and implantable cardioverter defibrillators.

Provided herein are methods and systems for treating a condition in a subject in need thereof, comprising administering to the subject a Neural Implantable Electronic Device (NIED), and a microporous gel system disclosed herein. NIEDs include, but are not limited to, a neural implant, a brain implant, and a spinal implant. The implant may also be referred to as neural stimulator or prosthetic. The microporous scaffolds disclosed herein may provide an interface between the NIED and a neuron or a brain. The microporous scaffolds disclosed herein may provide an interface between the NIED and subcutaneous or connective tissue. The NIED may comprise an electrode. NIEDs may include, but are not limited to computer chips, an electro echocardiogram array, a spinal cord stimulator. The NIED may be a device that produces a deep brain stimulation. The NIED may be a device that produces a vagus nerve stimulation. The NIED may be a neuroimaging device or a neurological activity recording device. The NIED may be a brainstem implant. The NIED may be a device that is placed in or on a brain. The NIED may be placed in a sensory organ (e.g., ear, eye, nose, brain, skin). The NIED may be placed in a spine or brain stem of a subject. The NIED may be a device that is placed in or on an eye. The NIED may be a device that is placed in or on an ear, such as a cochlear implant, by way of non-limiting example. The NIED may comprise a computer chip. The microporous scaffolds disclosed herein may provide an interface between the computer chip and a neuron or a brain (brain-computer interface). The NIED may be a device that stimulates, blocks or records signals from neurons. The NIED may be a device that re-wires the brain or re-wires neurons in the subject. Re-wiring may comprise forming or blocking a neural synapse.

The medical devices disclosed herein may be connected to a computer or in communication with a computer. The medical devices disclosed herein may be battery operated. The medical devices disclosed herein may be connected or in communication with a recording device, a stimulating device, an electrical device, a power source, a computer, a controller, or any combination thereof.

Medical devices disclosed herein may comprise a coating. In some instances, medical devices disclosed herein do not comprise a coating. In some instances, medical devices disclosed herein are pre-coated with a coating. In some instances, the coating comprises a coating functional group that acts as an annealing component. In some instances, the coating comprises a coating functional group that is capable of binding a flowable microgel particle disclosed herein. In some instances, some instances, the coating comprises a coating functional group that is capable of reacting with a flowable microgel particle disclosed herein. In some instances, the coating comprises a coating functional group that is capable of binding an annealing component disclosed herein. In some instances, the coating comprises a coating functional group that is capable of reacting with an annealing component disclosed herein. In some instances, the coating comprises a coating functional group that is capable of binding a crosslinker disclosed herein. In some instances, the coating comprises a coating functional group that is capable of reacting with a crosslinker disclosed herein. In some instances, the coating functional group is an annealing component. The functional group may become a part of an extracrosslink between the medical device and the flowable microgel particle.

Systems disclosed herein may comprise a device coating agent, wherein the device coating agent enables coating of the microporous gel system to the medical device. The systems disclosed herein may comprise a device coating agent, wherein the device coating agent promotes coating of the microporous gel system to the medical device. The systems disclosed herein may comprise a device coating agent, wherein the device coating agent enables adhesion of the microporous gel system to the medical device. The systems disclosed herein may comprise a device coating agent, wherein the device coating agent promotes adhesion of the microporous gel system scaffold to the medical device.

Systems disclosed herein may comprise a device coating agent, wherein the device coating agent enables adhesion of the stabilized scaffold to the medical device. The systems disclosed herein may comprise a device coating agent, wherein the device coating agent promotes adhesion of the stabilized scaffold to the medical device. The device coating agent may be applied to the medical device. The device coating agent may be a component of the microporous gel system. The device coating agent may be mixed with the microporous gel system or component thereof, prior to use. The device coating agent may comprise a ceramic, also referred to in the art as a bioceramic or a bioglass. The device coating agent may comprise a polymer. The polymer may comprise polyethylene glycol. The polymer may comprise a polyvinyl group. The polymer may comprise a parylene. The polymer may comprise a poly-N-vinylpyrrolidone) (PNP). The polymer may comprise a polyurethane. The polymer may comprise hyaluronan or hyaluronic acid.

Therapeutic Agents

Provided herein are systems comprising a therapeutic agent disclosed herein. Non-limiting examples of therapeutic agents are anti-inflammatory agents, antimicrobial agents, and analgesics. The therapeutic agent may be incorporated in the flowable microgel particles. The therapeutic agent may be incorporated in the flowable microgel particles before forming the stabilized scaffold. The therapeutic agent may be mixed with the flowable microgel particles and/or annealing agent before forming the stabilized scaffold. The therapeutic agent may be incorporated in the stabilized scaffold after forming the stabilized scaffold. The therapeutic agent may be released from the stabilized scaffold into or on to the site or tissue of the subject. For example, the therapeutic agent may be incorporated in the stabilized scaffold and released as the stabilized scaffold is degraded in the tissue or as the stabilized scaffold is infiltrated by cells of the tissue or subject. The therapeutic agent may be released either by an internal trigger such as tissue mediated and/or enzyme mediated hydrolysis, hydrolysis not mediated by tissue or enzymes, enzymolysis, redox change, temperature change or by an external trigger such as light, electromagnetic field, ultrasound. Alternatively or additionally, the system may comprise a therapeutic agent. The therapeutic agent may be released from the stabilized scaffold by addition of therapeutic agent-releasing agent. The therapeutic agent may be connected to or contained within a nanoparticle or nanoparticle system disclosed herein. In some instances, the medical device comprises a therapeutic agent disclosed herein. Systems disclosed herein may comprise a single therapeutic agent or a combination of a plurality of therapeutic agents.

Figure 3:
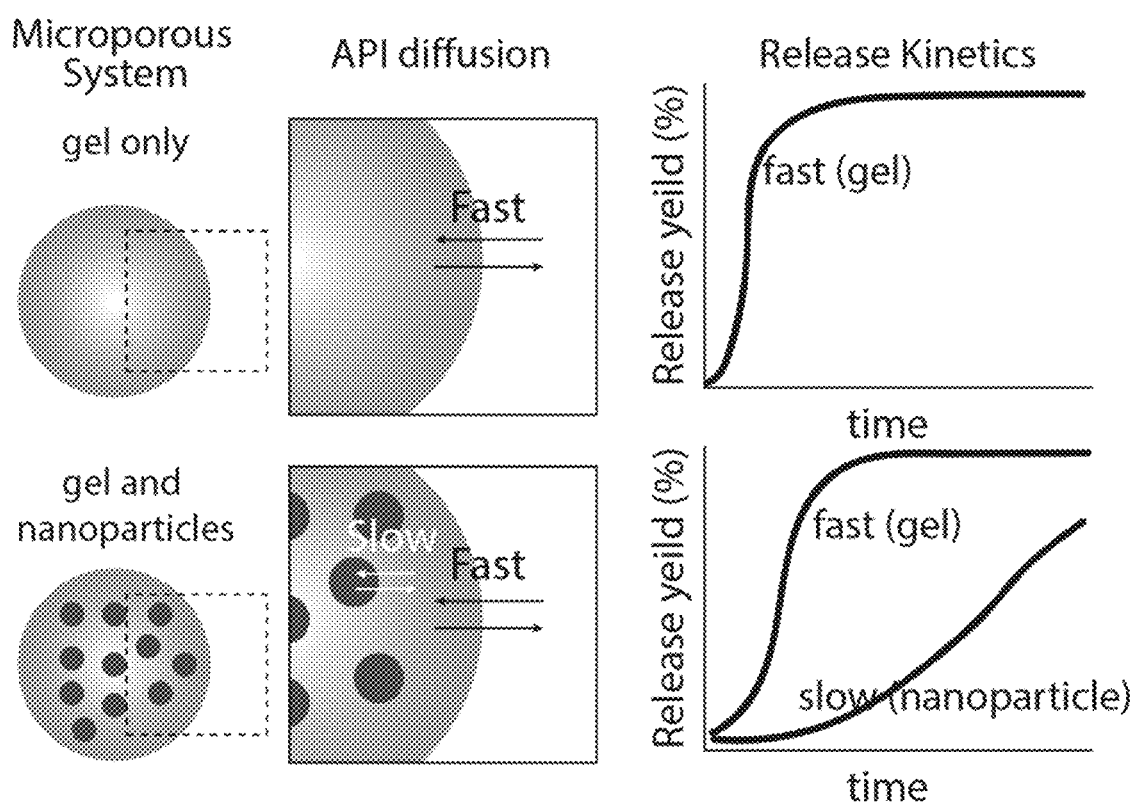
FIG. 3 shows an exemplary method of controlling the release of diffusible molecules (active pharmaceutical ingredients) into the microporous gel. By combining multiple diffusion rates, dependent upon diffusion rates only (gel) and multiple mechanisms including enzymatic, hydrolytic, photonic, and thermal (nanoparticles), the microporous gel can achieve highly complex release profiles DIRECTLY to the cells growing through it (unlike any other scaffolding systems).

Provided herein are systems comprising a therapeutic agent, wherein the therapeutic agent is incorporated in the stabilized scaffold and released from the stabilized scaffold. In certain embodiments, the therapeutic agent is released from the stabilized scaffold at more than one rate, see, e.g., FIG. 3. In certain embodiments, the therapeutic agent is actively released. In some embodiments, the therapeutic agent is passively released, also referred to as "diffused." The therapeutic agent may be released in less than about one day. The therapeutic agent may be released in less than about a week. The therapeutic agent may be released in less than about one month. The therapeutic agent may be released in less than one day. The therapeutic agent may be released in less than a week. The therapeutic agent may be released in less than one month. At least a portion of the therapeutic agent may be released in less than about one day. A least a portion of the therapeutic agent may be released in less than about one week. At least a portion of the therapeutic agent may be released in less than about one month. At least a portion of the therapeutic agent may be released in less than one day. At least a portion of the therapeutic agent may be released in less than one week. At least a portion of the therapeutic agent may be released in less than one month. The therapeutic agent may be released from the stabilized scaffold over a period of about 1 day to about 1 week. The therapeutic agent may be released from the stabilized scaffold over a period of about 1 day to about 2 weeks. The therapeutic agent may be released from the stabilized scaffold over a period of about 1 day to about 3 weeks. The therapeutic agent may be released from the stabilized scaffold over a period of about 1 day to about 100 days. At least a portion of the therapeutic agent may be released over a period of about 1 day to about 100 days. The therapeutic agent may be released from the stabilized scaffold over a period of 1 day to 1 week. The therapeutic agent may be released from the stabilized scaffold over a period of 1 day to 2 weeks. The therapeutic agent may be released from the stabilized scaffold over a period of 1 day to 3 weeks. The therapeutic agent may be released from the stabilized scaffold over a period of 1 day to 100 days. At least a portion of the therapeutic agent may be released over a period of 1 day to 100 days. The portion of the therapeutic agent may be about 1% to about 50% of the therapeutic agent. The portion of the therapeutic agent may be about 10% to about 50% of the therapeutic agent. The portion of the therapeutic agent may be about 10% to about 80% of the therapeutic agent. The portion of the therapeutic agent may be about 1% to about 10%. The portion of the therapeutic agent may be 1% to 50% of the therapeutic agent. The portion of the therapeutic agent may be 10% to 50% of the therapeutic agent. The portion of the therapeutic agent may be 10% to 80% of the therapeutic agent. The portion of the therapeutic agent may be 1% to 10%.

The therapeutic agent may be present in the microporous gel system at a concentration of about 1 µg/mL to about 1 mg/mL. The therapeutic agent may be present in the microporous gel system at a concentration of about 1 µg/mL, about 5 µg/mL, about 10 µg/mL, about 20 µg/mL, about 30 µg/mL, about 40 µg/mL, about 50 µg/mL, about 60 µg/mL, about 70 µg/mL, about 80 µg/mL, about 90 µg/mL, or about 100 µg/mL. The therapeutic agent may be present in the microporous gel system at a concentration of about 100 µg/mL, about 200 µg/mL, about 300 µg/mL, about 400 µg/mL, about 500 µg/mL, about 600 µg/mL, about 700 µg/mL, about 800 µg/mL, about 900 µg/mL, or about 1 mg/mL. The therapeutic agent may be present in the microporous gel system at a concentration of about 1 mg/mL to about 10 mg/mL. The therapeutic agent may be present in the microporous gel system at a concentration of about 10 mg/mL to about 350 mg/mL. The therapeutic agent may be present in the microporous gel system at a concentration of about 50 mg/mL to about 300 mg/mL. The therapeutic agent may be present in the microporous gel system at a concentration of about 5 mg/mL, about 10 mg/mL, about 20 mg/mL, about 40 mg/mL, about 60 mg/mL, about 80 mg/mL, about 100 mg/mL, about 150 mg/mL, about 200 mg/mL, about 250 mg/mL, about 300 mg/mL, about 350 mg/mL, or about 400 mg/mL. The therapeutic agent may be present in the microporous gel system at a concentration of 1 μg/mL to 1 mg/mL. The therapeutic agent may be present in the microporous gel system at a concentration of 1 μg/mL, 5 μg/mL, 10 μg/mL, 20 μg/mL, 30 μg/mL, 40 μg/mL, 50 μg/mL, 60 μg/mL, 70 μg/mL, 80 μg/mL, 90 μg/mL, or 100 μg/mL. The therapeutic agent may be present in the microporous gel system at a concentration of 100 μg/mL, 200 μg/mL, 300 μg/mL, 400 μg/mL, 500 μg/mL, 600 μg/mL, 700 μg/mL, 800 μg/mL, 900 μg/mL, or 1 mg/mL. The therapeutic agent may be present in the microporous gel system at a concentration of 1 mg/mL to 10 mg/mL. The therapeutic agent may be present in the microporous gel system at a concentration of 10 mg/mL to 350 mg/mL. The therapeutic agent may be present in the microporous gel system at a concentration of 50 mg/mL to 300 mg/mL. The therapeutic agent may be present in the microporous gel system at a concentration of 5 mg/mL, 10 mg/mL, 20 mg/mL, 40 mg/mL, 60 mg/mL, 80 mg/mL, 100 mg/mL, 150 mg/mL, 200 mg/mL, 250 mg/mL, 300 mg/mL, 350 mg/mL, or 400 mg/mL.

Provided herein are systems and methods that comprise anti-inflammatory agents, combinations thereof, and uses thereof. The anti-inflammatory agent may be a steroidal or hormonal agent. The anti-inflammatory agent may be a non-steroidal anti-inflammatory agent. The anti-inflammatory agent may be synthetic or non-naturally-occurring. The anti-inflammatory agent may be naturally-occurring. By way of non-limiting example, the anti-inflammatory agent may be ibuprofen, aspirin, natural or synthetic corticosteriods, an anti-inflammatory neuropeptide α-melanocyte stimulating hormone (α-MSH), dexamethasone, or meloxicam, or combinations thereof.

Provided herein are systems and methods that comprise antimicrobial agents, combinations thereof, and uses thereof. The antimicrobial agent may be an antibacterial agent, also referred to as an antibiotic. The antimicrobial agent may be selected from an antibacterial agent, an antifungal agent, an antimycotic agent, an antiparasitic agent, or an antiseptic agent. By way of non-limiting example, the antibiotic may be a β-lactam (e.g., penam, cephem, monobactam, carbapenem, penicillin, cefriaxone), a macrolide (e.g., erythromycin), an aminoglycoside (e.g., tobramycin, neomycin, ampicillin, aminopenicillin, amoxicillin, kanamycin), a glycopeptide antibiotic (e.g., vancomycin), a quinolone (e.g., ciprofloxacin levofloxacin, moxifloxacin), a tetracycline, a phenicol or a sulfonamide.

Provided herein are systems comprising a combination of antimicrobial agents. The combination of antimicrobial agents may comprise a combination of antibiotics. The combination of antibiotics may be selected from a combination of a β-lactam, a macrolide, an aminoglycoside, a glycopeptide antibiotic, a quinolone, a tetracycline, a phenicol, a sulfonamide. The antibiotic may be present in the microporous gel system or the stabilized scaffold at a minimal inhibitory concentration. The antibiotic may be present in the microporous gel system or the stabilized scaffold at a concentration that is bactericidal at the implant site or surgical site. The antibiotic may be present in the microporous gel system or the stabilized scaffold at a concentration that is bacteriostatic at the implant site or surgical site.

Provided herein are systems comprising an antimicrobial agent, wherein the antimicrobial agent is incorporated in the stabilized scaffold and released from the stabilized scaffold. The antimicrobial agent may be released from the stabilized scaffold at a rate. In certain embodiments, the antimicrobial agent is released from the stabilized scaffold at more than one rate, see, e.g., FIG. 3. In certain embodiments, the antimicrobial agent is actively released. In some embodiments, the antimicrobial agent is passively released, also referred to as "diffused." The antimicrobial agent may be an antibiotic. The antimicrobial agent may be released over the period of at least about one week. The antimicrobial agent may be released over the period of at least about ten days. The antimicrobial agent may be released over the period of at least about two weeks. The antimicrobial agent may be released over the period of at least about three weeks. The antimicrobial agent may be released over the period of at least about four weeks. The antimicrobial agent may be released over the period of one week. The antimicrobial agent may be released over the period often days. The antimicrobial agent may be released over the period of two weeks. The antimicrobial agent may be released over the period of three weeks. The antimicrobial agent may be released over the period of four weeks. The antimicrobial agent may be released at a rate that reduces or kills microbes at the implant site or surgical site. The amount of antimicrobial agent, and the rate at which it is released at the implant site or surgical site, may be considered bactericidal. The antimicrobial agent may be released at a rate that maintains microbe presence at the implant site or surgical site, but prevents growth of microbes at the implant site or surgical site. The amount of antimicrobial agent, and the rate at which it is released at the implant site or surgical site, may be considered bacteriostatic.

Provided herein are systems that comprise an agent that prevents, alleviates or reduces pain or discomfort at the implant site or surgical site. Provided herein are systems and methods that comprise at least one analgesic, combinations of analgesics, or a use thereof. By way of non-limiting example, the analgesic may be paracetamol (also known as acetaminophen), an opioid, a non-steroidal anti-inflammatory drug (NSAID), a cyclooxygenase inhibitor, a cannabinoid, a ketamine, and a combination thereof. Alternatively, or additionally, the systems and methods may comprise a local anesthetic or a use thereof. By way of non-limiting example, the local anesthetic may be benzocaine, chloroprocaine, cyclomethycaine, dimethocaine/larocaine, piperocaine, propoxycaine, procaine/novocaine, proparacaine, tetracaine/amethocaine, chloroprocaine, saxitoxin, neosaxitoxin, tetrodotoxin, menthol, or eugenol, or a combination thereof. In certain embodiments, the system to method comprises a combination of the local anesthetic with a vasoconstrictor, or a used thereof. A non-limiting example of a vasoconstrictor is epinephrine. Provided herein are therapeutic agents disclosed herein and methods of incorporating the therapeutic agents into the microporous gel systems disclosed herein. The therapeutic agent may be directly incorporated in the microporous gel system disclosed herein. For example, the therapeutic agent may be loaded into or on to the microgel particles of the microporous gel system. The therapeutic agent may be passively loaded into the microporous gel via diffusion. The therapeutic agent may be passively loaded into the microporous gel via entrapment. The therapeutic agent may be directly incorporated in the microporous gel system by a covalent linkage between the therapeutic agent and a polymer or crosslinker of the microporous gel system. The therapeutic agent may be directly incorporated in the microporous gel system by immobilization of the therapeutic agent via a photo-caging method. The therapeutic agent may be loaded in a nanoparticle (a therapeutic agent-loaded nanoparticle). The microporous gel systems disclosed herein may comprise a mixture of therapeutic agent-loaded microparticles and therapeutic agent-loaded nanoparticles embedded into the microgel particles. Methods for incorporating therapeutic agent-loaded nanoparticles into the microporous gel system may comprise dissolving lyophilized therapeutic agent-loaded nanoparticles in an aqueous buffer prior to mixing the therapeutic agent-loaded nanoparticles with the microporous gel system. Methods for incorporating therapeutic agent-loaded nanoparticles into the microporous gel system may comprise directly embedding the therapeutic agent-loaded nanoparticles into the microgel particles during the microgel fabrication. The microporous gel systems disclosed herein may comprise a mixture of therapeutic agent-loaded microparticles and therapeutic agent-loaded nanoparticles embedded into the microgel particles.

Provided herein are systems that comprise a microporous gel system disclosed herein, wherein the microporous gel system releases a therapeutic agent disclosed herein into a tissue or biological fluid of a subject. Release of therapeutic agents may occur via passive diffusion from the microgel particles and/or nanoparticles (see, e.g., FIG. 3). Release of therapeutic agents may occur via an active release. The active release may be initiated by an external stimulus. The external stimulus, by way of non-limiting example, may be light (e.g., UV or NIR), a change of temperature, ultrasound, or a magnetic field. The active release may be initiated by an internal stimulus. The internal stimulus may be produced by the subject. The internal stimulus, by way of non-limiting example, may be a pH change, a redox reaction, enzymatic activity, or chemical activity.

Therapeutic agents disclosed herein may be delivered in nanoparticles. By way of non-limiting example, nanoparticles may comprise a polymer selected from poly(lactic-co-glycolic acid) (PLGA) or a copolymer thereof, a poly (anhydride), a poly(amide), a poly(ortho ester), a polycaprolactone. The nanoparticle may comprise hyaluronic acid. The nanoparticle may comprise chitosan. The nanoparticle may be a mesoporous silica nanoparticle. The nanoparticle may comprise a polymer with a lower critical solution temperature (LCST), such as poly(N-isopropylacrylamide) (PNIPAm) or co-polymer of PNIPAm, by way of non-limiting example. The nanoparticle may comprise a polymer with an upper critical solution temperature (UCST) such as poly(hydroxyethylmethacrylate) (PHEMA) or polyethylene oxide (PEO) or poly(ethyleneoxide)-poly(propyleneoxide)-poly(ethyleneoxide) (PEO-PPO-PEO). The nanoparticle may comprise a self-immolating polymer such as poly(p-aminobenzyl oxycarbonyl) (poly(PABC)) that is capped with a cage that can be released upon a stimulus (e.g., light, temperature, pH, redox, enzyme). In self-immolating systems, a single cleavage event of an end-cap can trigger an entire chain to degrade into small molecules, allowing the entrapped drug to be released. For instance, silver nitrate (used as an oxidizing agent) can be encapsulated into thermosensitive liposomes (made of 90 mol % dipalmitoyl phosphatidylcholine and 10 mol % of 1-palmitoyl lysophosphatidylcholine). The silver nitrate-loaded liposomes are entrapped in DOPA-functionalized microgel particles and are stable at room temperature. By way of non-limiting example, nanoparticles may comprise liposomes or lipid vesicles. At body temperature, the lipid bilayer of the liposomes is more permeable allowing silver nitrate to be released and oxidize the catechol of the DOPA moieties into reactive quinones that can further react with another DOPA group leading to the crosslinking of the DOPA-functionalized microgel particles.

Provided herein are systems that comprise a core-shell nanoparticle system in which the shell responds to a stimulus. The core or shell may comprise any combination of the materials that are components of the nanoparticles disclosed herein. This core shell system may enable the nanoparticles to retain a cargo, such as a therapeutic agent disclosed herein, while being stored in an aqueous environment (e.g., inside the microgel solution in a syringe). The cargo may be released by applying an external stimulus to the tissue site (e.g., light, electromagnetic radiation). The cargo may be released by an internal stimulus, present in a tissue of the subject, (e.g., enzymes, redox potential, pH, temperature). The microporous gel system may comprise a first portion of microgel particles and a second portion of microgel particles, wherein the first portion of microgel particles comprises the core-shell nanoparticle system, and wherein the second portion of microgel particles comprises an agent that dissolves the shell and initiates release of the cargo from the first portion of microgel particles. The methods disclosed herein may comprise delivering the first portion and the second portion of microgel particles simultaneously or sequentially, through a single or multiple syringes or multi-barrel syringe/cannula/tube systems.

Methods and Systems for Producing Microporous Gel Systems

Provided herein are methods and systems for producing microporous gel systems. One of skill in the art understands that methods for producing microporous gel systems described herein may be performed with manufacturing systems comprising reagents and materials employed by the methods. In some instances, the methods comprise synthesizing flowable microgel particles. The term "flowable microgel particle," as described herein, includes a hydrogel particle. Generally, flowable microgel particles disclosed herein comprise a high water content and "intra-crosslinks" (crosslinks within the particles). In general, a high water content is a water content greater than 50% to up to about 99.9% water. In some instances, the water content is about 60% to about 99.9%. In some instances, the water content is about 70% to about 99.9%. The intra-crosslinks may be physical, chemical, or a combination thereof.

Synthesis of Flowable Microgel Particles

The microgel particles may be synthesized using a microfluidic device (one particle at a time per channel). The microgel particles may be synthesized by water-in-oil emulsion as described in greater detail herein. The microgel particles may be synthesized by water-in-oil emulsion with mechanical stirring. The microgel particles may be synthesized by water-in-oil emulsion using a static mixer. The microgel particles may be synthesized using in-line flow-through synthesis. The microgel particles may be synthesized using a parallel production method (multiple particles at a time per channel). Methods of synthesizing flowable microgel particles disclosed herein are described in further detail throughout the instant disclosure.

Methods disclosed herein may comprise synthesizing microgel particles by a water-in-oil emulsion process. In some instances, the methods being with obtaining an oil or an oil mixture. By way of non-limiting example, the oil may be a light mineral oil (LMO) or a heavy mineral oil (HMO). In some instances, oil mixtures comprise a surfactant. Different surfactants can be employed. The surfactant may be a nonionic surfactant. Non-limiting examples of nonionic surfactants are Span80, Span20, Tween20, Tween40, Tween60, Tween80, and tocopheryl polyethylene glycol 1000 succinate (TPGS). The surfactant may be an anionic surfactant. Non-limiting examples of anionic surfactants are sodium dodecyl sulfate (SDS), sodium lauryl ether sulfate (SLES), and perfluorooctanesulfonate. The surfactant may be a cationic surfactant. Non-limiting examples of cationic surfactants are cetyltrimethylammonium bromide (CTAB), and hexadecylpyridium bromide. The surfactant may be an amphoteric surfactant. Non-limiting examples of amphoteric surfactants are betaine citrate, lauryl betaine, sodium, and (carboxymethyl) dimethyloleyl ammonium hydroxide. The concentration of the surfactant may vary from 0.01 to 5% v/v.

In some instances, methods comprise adding the surfactant to the oil. In some instances, methods comprise adding the surfactant to the oil prior to the addition of an aqueous solution/mixture to the oil. In some instances, methods comprise adding the surfactant to an aqueous solution/mixture described herein. In some instances, having a surfactant in the aqueous phase is beneficial because if the surfactant has a high-water solubility it is easy to remove during purification.

The oil or oil mixture may be added to a bioreactor vessel through a micron filter and stirred. In some instances, the bioreactor vessel contains a volume from about 100 milliliters to about 1 liter. In some instances, the bioreactor vessel contains a volume from about 1 liter to about 10 liters. In some instances, the bioreactor vessel contains a volume from about 10 liters to about 100 liters. In some instances, the bioreactor vessel contains a volume from about 100 liters to about 1000 liters. In some instances, the bioreactor vessel contains a volume from about 100 liters to about 10,000 liters. In some instances, the bioreactor vessel contains a volume from about 10 liters to about 1000 liters. In some instances, the bioreactor vessel contains a volume from about 1000 liters to about 10,000 liters. In some instances, the micron filter has a pore size of about 0.1 μm to about 1 μm. In some instances, the micron filter has a pore size of about 0.2 μm.

In some instances, methods of synthesizing microgel particles comprise modifying a backbone polymer. In some instances, methods comprise attaching one or more functional groups to the backbone polymer. In some instances, only one functional group is attached, and the resulting backbone polymer is referred to as a polymerization monomer. In some instances, two or more functional groups are attached, and the resulting backbone polymer is referred to as an intracrosslinking component. The term, "intracrosslinking component," as used herein, generally refers to molecules that participate in the formation of the intracrosslinks (they form the crosslink bonds). In some instances, an intracrosslinking component is also an intracrosslinker.

In some instances, methods of synthesizing microgel particles comprise mixing two or more types of intracrosslinking components. In some instances, methods of synthesizing microgel particles comprise mixing two or more types of intracrosslinking components and an intracrosslinking agent. In some instances, methods of synthesizing microgel particles comprise mixing an intracrosslinking component and an intracrosslinking agent. In some instances, methods of synthesizing microgel particles comprise mixing a polymerizing agent and a polymerization monomer.

In some instances, methods comprise obtaining a solution of at least one of an intracrosslinking component. In some instances, methods comprise preparing a solution of at least one of an intracrosslinking component. In some instances, methods comprise including an intracrosslinking agent in the solution. In other instances, an intracrosslinking agent is not required because the intracrosslining component(s) self-crosslink without a crosslinking agent. Methods may comprise filtering the solution. The solution may comprise a backbone polymer. The solution may comprise a peptide. The solution may comprise a buffer or buffering agent. The solution may comprise a base catalyst.

By way of non-limiting example, a solution comprising backbone polymer: 4-arm poly(ethylene glycol) functionalized with four vinyl sulfone groups (PEG-VS) and limiting amounts of K-peptide (Ac-FKGGERCG-NH2), Q-peptide (Ac-NQEQVSPLGGERCG-NH2), and RGD (Ac-RGD-SPGERCG-NH2); may be mixed with MMP-degradable peptide with thiol-containing cysteines on the N and C termini. Both the functionalized PEG-VS and MMP-degradable peptide provide intracrosslinking components; PEG-VS provides four vinyl sulfone groups and MMP-degradable peptide provides two thiol groups. Upon mixing of the PEG-VS and MMP-degradable peptide (both intracrosslinking components) in the presence of triethanolamine, a base catalyst and intracrosslinking agent, intracrosslinking takes place and particles are formed. K-peptide (Ac-FKG-GERCG-NH2), Q-peptide (Ac-NQEQVSPLGGERCG-NH2), and RGD (Ac-RGDSPGERCG-NH2); intracrosslinker; and base catalyst: triethanolamine.

The concentration of 4-arm poly(ethylene glycol) vinyl sulfone (PEG-VS) (20 kDa) may be about 5% w/v to about 15% w/v. The concentration of 4-arm poly(ethylene glycol) vinyl sulfone (PEG-VS) may be about 10% w/v. The PEG-VS may be PEG-VS (20 kDa). The concentration of K-peptide may be about 100 μM to about 1 mM. The concentration of K-peptide may be about 500 μM. The concentration of Q-peptide may be about 100 μM to about 1 mM. The concentration of Q-peptide may be about 500 μM. The concentration of RGD may be about 0.1 mM to about 10 mM. The concentration of RGD may be about 1 mM. The concentration of triethanolamine may be about 50 mM to about 500 mM. The concentration of triethanolamine may be about 300 mM. The pH of triethanolamine may be about 7 to about 9. The pH of triethanolamine may be about 7.75.

In some instances, methods comprise obtaining an intracrosslinker solution. In some instances, methods comprise preparing an intracrosslinker solution. The intracrosslinker solution may comprise a degradable peptide. The intracrosslinker solution may comprise di-cysteine MMP-sensitive peptide. The concentration of the intracrosslinker in the intracrosslinker solution may be about 1 mM to about 50 mM. The concentration of the intracrosslinker in the intracrosslinker solution may be about 5 mM to about 15 mM. The method may comprise filtering the intracrosslinker solution.

Methods of producing may comprise mixing the intracrosslinking agent with the crosslinker solution to produce an aqueous mixture. In some instances, methods comprise adding the aqueous mixture to the oil in an oil container. In some instances, methods comprise adding an aqueous mixture to oil at a volume fraction of the aqueous phase into the oil phase. The volume fraction may be about 1% to about 10% v/v/w/o. In some instances, methods comprise injecting the aqueous mixture into the oil. Injecting may comprise the use of a peristaltic pump. In some instances, the peristaltic pump is operated at about 100 mL/min to about 200 mL/min. In some instances, the peristatic pump is operated at about 150 mL/min. In some instances, the peristatic pump is operated at about 135 mL/min. In some instances injecting is performed immediately after mixing. The methods may comprise stirring the oil as the aqueous mixture is added. The speed of stirring (agitation) may vary from 100-20,000 rpm, depending upon the size of the reaction vessel and the size of particles needed. Different impeller types may be used for the agitation (turbine overhead stirrer, paddle overhead stirrer, blade stirrer, dissolver stirrer, spiral stirrer, propeller stirrer, double impeller). Stirring may occur for at least 1 hour. Stirring may occur for at least 2 hours. Stirring may occur for about 1 hour to about 24 hours. When stirring stops, flowable microgel particles settle to the bottom of the oil container. The final size of the flowable microgel particles may be dependent upon the concentrations of the materials, the speed of stirring, volume fraction, and speed of injection of the aqueous phase to the oil phase.

In some instances, the methods may comprise a base-catalyzed Michael addition. The base may be an amine (e.g. triethanolamine, trimethylamine), an amidine (e.g. 1,8-diazabicycloundec-7-ene (DBU), 1,5-diazabicyclo[4.3.0]non-5-ene (DBN)), an imidazole, a pyridine (e.g. 4-dimethylaminopyridine (DMAP)), an amine (e.g., n-pentylamine), a phosphine (e.g. tri-n-propylphosphine, dimethylphenylphosphine, methyldiphenylphosphine, triphenylphosphine). In some instances, the base is added to the oil prior to addition of an aqueous phase to oil. In some instances, the base is added to a solution disclosed herein prior to formation of an aqueous mixture. In some instances, it is beneficial to add the base to the oil because it ensures initiation of the gelation occurs only when the aqueous mixture is added to the oil.

In some instances, methods comprise synthesizing flowable microgel particles by pumping the aqueous mixture into the oil and mixing the resulting emulsion with a static mixer connected to a reaction vessel. The flowable microgel particles that are generated by the static mixer are collected in the reaction vessel and kept under gentle agitation until the reaction is complete. In this method, a base catalyst may be added to the oil to prevent a gelation reaction from occurring in the aqueous mixture before particle dispersion in the static mixer. Benefits of using a static mixer include, but are not limited to the following: gelation may occur when both phases are in contact in the static mixer; less oil is required; and a greater particle concentration is obtained. Thus, large manufacturing scales are achievable.

Purifying Flowable Microgel Particles

Methods disclosed herein may comprise purifying flowable microgel particles. In some instances, methods comprise synthesizing and purifying flowable microgel particles simultaneously. In some instances, methods comprise purifying flowable microgel particles after synthesizing the flowable microgel particles. In some instances, purifying flowable microgel particles comprises performing membrane separation of the flowable microgel particles from unwanted components. Different types of filtration membranes may be used (e.g., hollow fiber membranes with different pore sizes, different lumen IDs or flat sheet membrane). In some instances, membrane separation comprises tangential flow filtration (TFF). In some instances, membrane separation comprises ultrafiltration-diafiltration (UFDF). In some instances, membrane separation comprises microfiltration-diafiltration (MFDF)). In some instances, membrane separation comprises hollow-fiber-diafiltration (HFDF). TFF generally comprises a membrane filtration and separation technique. TFF may be used herein to purify and concentrate flowable microgel particles. TFF may comprise generating a feed stream of a solution of flowable microgel particles that passes parallel to a membrane face. One portion of the solution may pass through the membrane (permeate) while the remainder (retentate) is recirculated back to the feed reservoir. This system may be referred to as diafiltration. This system may allow molecules (in the permeate) smaller than the membrane pores to move toward and through the membrane while the larger molecules, such as the flowable microgel particles, remain in the retentate. In some instances, the flow in the filtration system may be controlled by a peristaltic pump. In some instances, the flow in the filtration system may be controlled by a Quattroflow pump or any positive displacement pump. In some instances, the filtration system may be closed to surrounding environment. In some instances, the filtration system may be open to surrounding environment.

Methods of purifying may comprise removing excess oil from the flowable microgel particles. Methods of purifying may comprise dispersing the particles in an alcohol solution. Methods of purifying may comprise removing excess oil and surfactant that are not miscible in water while keeping the particles (mainly composed of water) dispersed and sufficiently swollen and ensuring no particle aggregation. Methods of purifying may comprise slowly transferring the particles into an aqueous buffer while preventing the surfactant from precipitating. Transferring rate may be linked to the flux of filtrate passing through the membrane, and occur at a rate of about 1 to about 1000 LMH (liters/m²h). Transferring may occur at a rate of about 100 to about 500 LMH. Transferring may occur at a rate of about 200 to about 300 LMH. This transition rate may be particularly important to ensure that a surfactant does not precipitate on to (and within) the flowable microgel particles, rendering the particles unsuitable for a microporous scaffold. The transition rate may achieve at least one of (i) particle hydrogel mesh swelling, which is a product of the affinity for certain solvents for a given hydrogel polymer backbone/crosslinker system, and (ii) solubility of the surfactant in the continuous phase outside of the particle.

Figure 9:
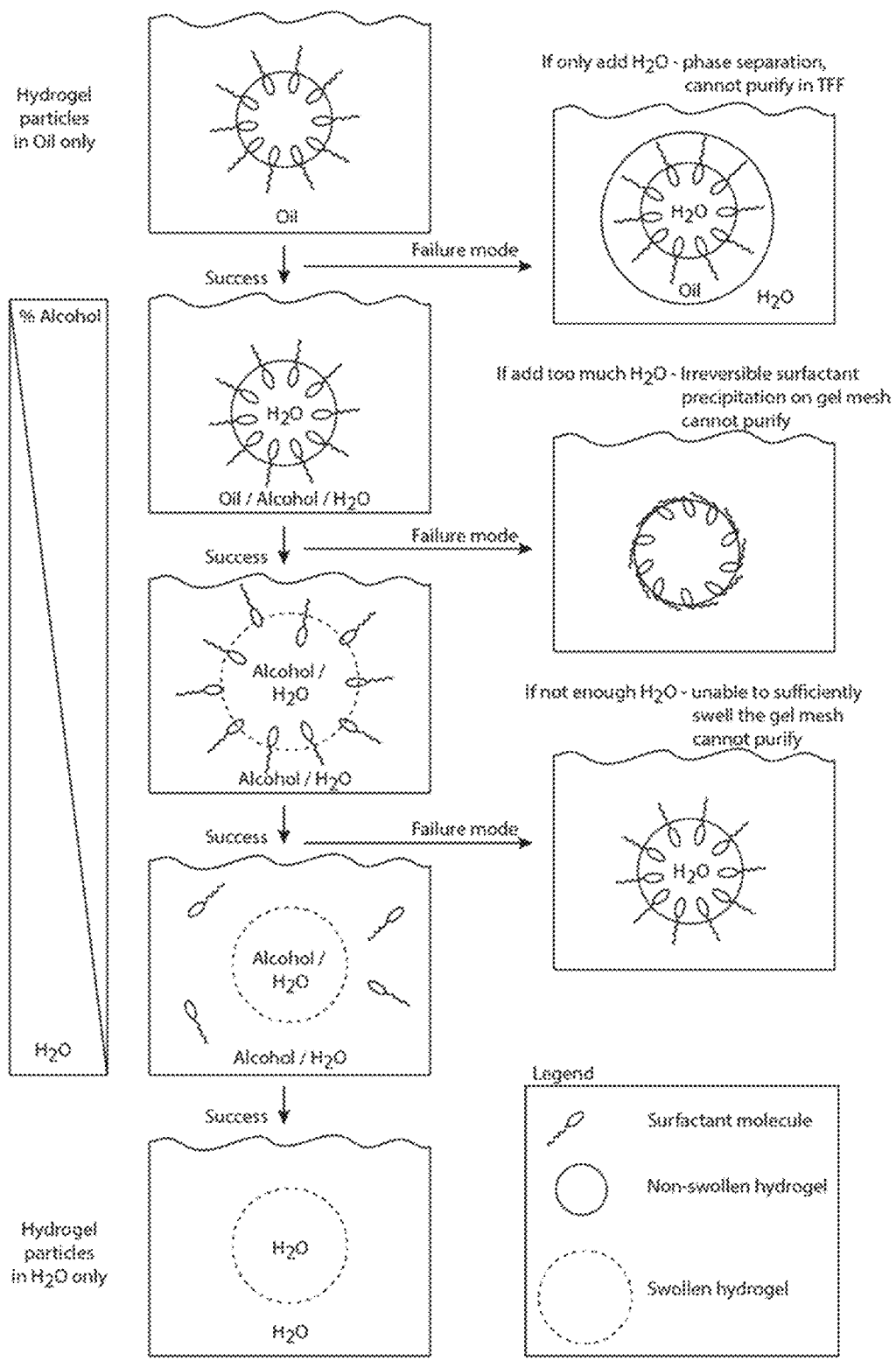
FIG. 9 shows an exemplary workflow of purifying flowable microgel particles, aiming to maintain one miscible continuous phase with isopropanol, which is miscible with both oil and water, as an intermediate solvent to transfer the particles, initially dispersed in oil, into water, and finally to an aqueous buffer.

Methods may comprise ensuring that there is only one miscible continuous phase to allow TFF to proceed by using an intermediate solvent (e.g. isopropanol (IPA)) which is miscible with both mineral oil and water, and capable of substantially swelling the particle mesh when mixed with either the mineral oil or the water. This can enable the transfer of the oil-dispersed particles from the oil into water, while removing surfactant and finally to an aqueous buffer, while never creating more than one miscible continuous phase. See, e.g., FIG. 9.

In some instances, methods comprise performing membrane filtration or membrane separation to concentrate the flowable microgel particles to a particle concentration in a solution, fluid, or solvent described herein. The shear rate occurring on the inside face of the membrane filter as solution passes by may affect the capability of concentrated particle suspensions to flow, and become increasingly difficult to maintain flow at high concentrations. In some instances, the shear rate may be between $1\ s^{-1}$ and $100\ s^{-1}$. In some instances, the shear rate may be between $100\ s^{-1}$ and $500\ s^{-1}$. In some instances, the shear rate may be between $500\ s^{-1}$ and $1,000\ s^{-1}$. In some instances, the shear rate may be between $1,000\ s^{-1}$ and $5,000\ s^{-1}$. In some instances, the shear rate may be between $5,000\ s^{-1}$ and $10,000\ s^{-1}$. The concentration may be about 1% v/v to about 100% v/v. The concentration may be about 1% v/v to about 10% v/v. The concentration may be about 10% v/v to about 20% v/v. The concentration may be about 20% v/v to about 30% v/v. The concentration may be about 30% v/v to about 40% v/v. The concentration may be about 40% v/v to about 50% v/v. The concentration may be about 50% v/v to about 60% v/v. The concentration may be about 60% v/v to about 70% v/v. The concentration may be about 70% v/v to about 80% v/v. The concentration may be about 80% v/v to about 90% v/v. The concentration may be about 90% v/v to about 99% v/v. The concentration may be about 90% v/v to about 100% v/v. Additionally or alternatively, flowable microgel particles are concentrated by centrifugation.

In some instances, methods comprise contacting the flowable microgel particles with at least one solvent to purify the particles. In some instances, methods comprise contacting the flowable microgel particles with a gradient of solvents. In some instances, the solvent is selected from an alcohol solution, water, and an aqueous buffer. In some instances, the solvent is an organic solvent (including alcohol solutions). Organic solvents may be suitable for transitioning flowable microgel particles from an oil phase to an aqueous phase. Organic solvents include, but are not limited to, isopropyl alcohol (IPA), methanol, ethanol, glycerol, acetone, acetonitrile, hexane, tetrahydrofuran, and 1,4-dioxane. In some instances, a combination of various organic solvents can be used. By way of non-limiting example, a combination of organic solvents may comprise hexane and IPA. In some instances, the alcohol solution comprises IPA, also referred to as isopropanol. In some instances, the alcohol solution consists of IPA and water. In some instances, the alcohol solution is about 30%, about 35%, about 40%, about 45%, about 50%, about 55%, about 60%, about 65%, about 70%, about 75%, about 80%, about 85%, or about 90% alcohol. In some instances, the alcohol solution is about 90%, about 92%, about 95%, about 98%, or about 99% alcohol. In some instances, methods comprise performing diafiltration with a 95% IPA solution. In some instances, methods comprise performing diafiltration with a 50% IPA solution. In some instances, methods comprise performing diafiltration with 100% pure water. Non-limiting examples of aqueous buffers include phosphate buffers, HEPES buffers, MES buffers, Tris buffers, Tricine buffers, PIPES buffers, borate buffers, MOPS buffers, and combinations thereof. In some instances, the aqueous buffer has a pH of about 6.6, about 6.0, about 6.2, about 6.4, about 6.6, about 6.8, about 7.0, about 7.2, about 7.4, about 7.6, about 7.8, about 8.0, about 8.2, about 8.4, about 8.6, about 8.8, or about 9.0. By way of non-limiting example, the aqueous buffer may comprise 10 mM phosphate buffer, 100 mM NaCl, and 5 µM Eosin Y, with a pH of 7.4.

In some instances, methods do not comprise initially adding only water to oil in which the flowable microgel particles are present. Adding water directly to oil would likely create two immiscible phases, in which the particles stick at an interface (along with precipitated surfactant), and foul separation membranes. In some instances, methods comprise initially adding an organic solvent and gradually transitioning to water through a gradient of solutions comprising decreasing amounts of organic solvent in water. In this way, a single miscible phase is maintained.

In some instances, methods of producing microgel particles comprise producing a mesh of polymers, peptides, or a combination thereof within the microgel particles. The mesh may be described as a three dimensional network formed by intracrosslinks within the microgel particle. The mesh is porous, resulting in pores within the particles. Pores within the microgel particles are generally nanoscopic pores, as opposed to the microscopic pores between the particles. Nanoscopic may be considered to be less than one micron in its greatest dimension. Microgel particles may swell in size when they are transitioning from organic solvent into water. Since the microparticles grow in size when they swell, polymer chains that make up the microgel particle may unfold in the water, thereby increasing the spacing within the 3D network (the mesh) and increasing the space between each neighboring polymer in the mesh (the pore size).

Annealing Flowable Microgel Particles

In some instances, the methods comprise annealing two or more flowable microgel particles together. This may be referred to as particle—particle annealing. Particle-particle annealing includes intercrosslinking. In some instances, annealing results in formation of at least one bond. In some instances, the bond is a covalent bond. Non-limiting examples of a covalent bond are bonds found in an amide, ester, C—C bond through Michael addition, carbamate, disulfide bond, oxime, thiourea, hydrazone, and imine. In some instances, the bond is a non-covalent bond. Non-limiting examples of non-covalent bonds are those found in an interaction such as, electrostatic interactions, hydrogen bonding, cation-π, π-π stacking, metal-ligand binding, and van der Waals interactions. In some instances, the methods comprise linking two or more flowable microgel particles together. Non-limiting examples of linking reactions include Michael addition, amide bond coupling, "click" chemistry (e.g. Diels-Alder cycloaddition, Huisgen 1,3-dipolar cycloaddition), reductive amination, carbamate linkage, ester linkage, thioether linkage, disulfide bonding, hydrazone bonding, oxime coupling, and thiourea coupling.

In some instances, methods disclosed herein comprise mixing flowable microgel particles that contain at least one annealing component. In general, annealing components comprise a reactive moiety. Non-limiting examples of annealing components include catechol (e.g., L-DOPA, dopamine), sialic acid (e.g., neuraminic acid), boronic acid (e.g., 3-aminophenylboronic acid), a molecular cage (e.g., cyclodextrins, cucurbiturils, calixarenes, pillararenes, crown ethers, cavitands, cryptands, carcerands), adamantane, biotin, and streptavidin. Additional examples of annealing components are described herein. In some instances, the at least one annealing component is part of a backbone polymer of a microgel particle. In some instances, the at least one annealing component is initially separate from the backbone polymer. In some instances, the at least one annealing component is part of the intracrosslinker of a microgel particle. In some instances, methods comprise adding the at least one annealing component to the flowable microgel particle, which may be referred to herein as "functionalizing" the flowable microgel particle or producing a "functionalized microgel particle." In some instances, mixing may occur in vitro. In some instances, mixing may occur ex vivo. In some instances, mixing may occur in vitro immediately before being applied to a subject or medical device. In some instances, mixing may occur ex vivo immediately before being applied to a subject or medical device. In some instances, mixing may occur in situ. In some instances, methods comprise applying multiple flowable microgel particles, annealing components, and additional system components described herein (e.g., therapeutic agents, annealing agents, etc.) with a multi-compartment applicator (e.g., multi-barrel syringe) to keep these components separate until application or immediately there before.

Methods disclosed herein may comprise annealing a first flowable microgel particle to a second flowable microgel particle, wherein the first flowable microgel particle and the second flowable microgel particle are the same. This may be referred to as "homo-annealing." An advantage to homo-annealing is that only one type of flowable microgel particle needs to be synthesized, simplifying the overall manufacturing process. Furthermore, homo-annealing does not require a two-compartment container to keep the flowable microgel particles separate until use, again simplifying the overall manufacturing process, as well as storage conditions. The first flowable microgel particle and the second flowable microgel particle may be connected by an annealing agent. In some instances, the annealing agent is a crosslinking agent. In some instances, the annealing agent initiates annealing between the first flowable microgel particle and the second flowable microgel particle but does not participate in the linkage or become a part of a resulting connection or linkage between the first flowable microgel particle and the second flowable microgel particle. The linkage may be covalent. The linkage may be non-covalent. A non-limiting example of an annealing agent may be a combination of thrombin and factor XIII. Another non-limiting example of an annealing agent may be a combination of eosin Y and light. Yet another non-limiting example of an annealing agent is an oxidizing agent (e.g., silver nitrate). Additional annealing agents are described herein. Alternatively, or additionally, the first flowable microgel particle and the second flowable microgel particle may be connected by a crosslinker. The crosslinker may participate in the linkage between microgel particles and become part of the resultant linkage. The crosslinker may be described as a molecule that contains two or more reactive ends capable of chemically attaching to the flowable microgel particles. In general, the linkage is covalent.

Methods disclosed herein may comprise annealing a first flowable microgel particle to a second flowable microgel particle, wherein the first flowable microgel particle has a first functional group (first annealing component) and the second flowable microgel particle has a second functional group (second annealing component), wherein the first functional group and the second functional group are different. Methods may comprise mixing the first flowable microgel particle and the second flowable microgel particle such that the first functional group reacts with the second functional group to form a bond. This may be referred to as "hetero-annealing." One advantage to hetero-annealing is that an external annealing agent or crosslinker is not required.

In some instances, the annealing component is part of the intracrosslinking component. In some instances, the annealing component is part of the intracrosslinker of a microgel particle. In some instances, the second annealing component is part of the backbone polymer of a microgel particle. In some instances, the intracrosslinking component is part of the annealing component. In some instances, the intracrosslinker of a microgel particle is part of the annealing component. In some instances, the backbone polymer of a microgel particle is part of the second annealing component.

Figure 4:
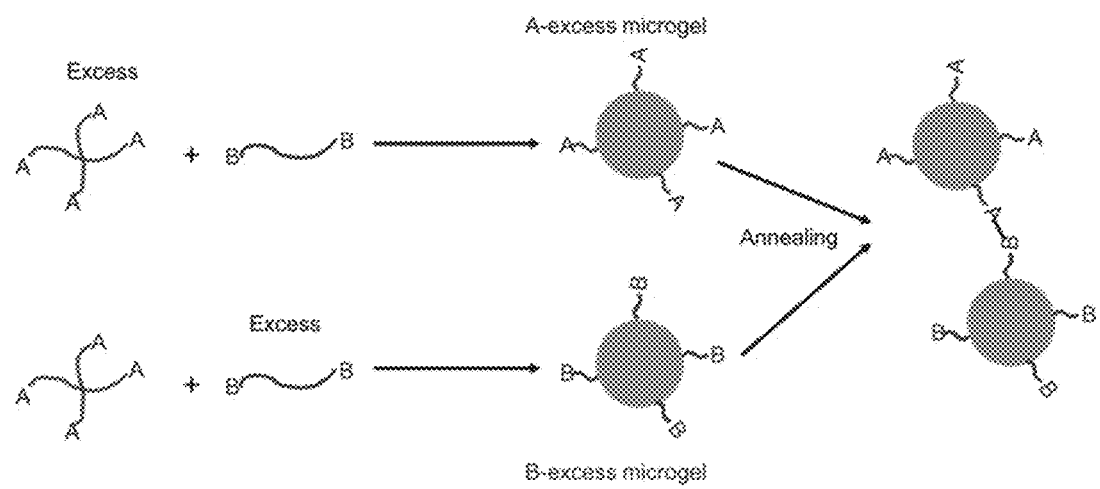
FIG. 4 shows an exemplary schematic representation of pre-functionalization of flowable microgel particles.

In some instances, methods disclosed herein comprise synthesizing flowable microgel particles in the presence of at least one annealing component. This may be referred to as pre-functionalization of the flowable microgel particles. The annealing component may be part of the intracrosslinking component. The first annealing component may be part of the intracrosslinker of a microgel particle. The second annealing component may be part of the backbone polymer of a microgel particle. In some instances, the methods comprise incorporating the first annealing component on to a first flowable microgel particle and incorporating the second annealing component on to a second flowable microgel particle. In some instances, the methods comprise mixing the first annealing component with the second annealing component, such that there is an excess of the first annealing component (e.g., ratio of first annealing component to second annealing component is greater than 1). In some instances, the methods comprise mixing the first annealing component with the second annealing component, such that there is an excess of the second annealing component (e.g., ratio of first annealing component to second annealing component is less than 1). The ratio of first annealing component to second annealing component may be about 0.1, about 0.2, about 0.3, about 0.5, about 0.8, about 1, about 1.2, about 1.5, about 1.8, or about 2. In some instances, there is a difference between an amount of the first annealing component and the second annealing component. In some instances, the difference is at least about 1%. In some instances, the difference is at least about 5%. In some instances, the difference is at least about 10%. In some instances, the difference is at least about 20%. In some instances, the difference is at least about 50%. In some instances, the difference is at least about 100%. In some instances, the methods further comprise annealing the first flowable microgel particle and the second flowable microgel particle via the first annealing component and second annealing component. In some instances, annealing occurs in situ. In some instances, annealing occurs in vitro. A schematic diagram is presented in FIG. 4 to depict an example of pre-functionalization of flowable microgel particles. Non-limiting examples of annealing components used for pre-functionalization include functional groups such as vinyl sulfone, thiol, amine, imidazole, aldehyde, ketone, hydroxyl, azide, alkyne, vinyl, alkene, maleimide, carboxyl, N-hydroxysuccinimide (NHS) ester, isocyanate, isothiocyanate, hydroxylamine, thione. By way of non-limiting example, microgel particles containing an excess of vinyl sulfone groups can covalently react with microgel particles containing an excess of thiol groups by Michael addition to create a microporous scaffold. Additional examples of annealing components are described herein. In some instances, pre-functionalization is desirable because it does not require further modification of particles after synthesis.

Figure 5:
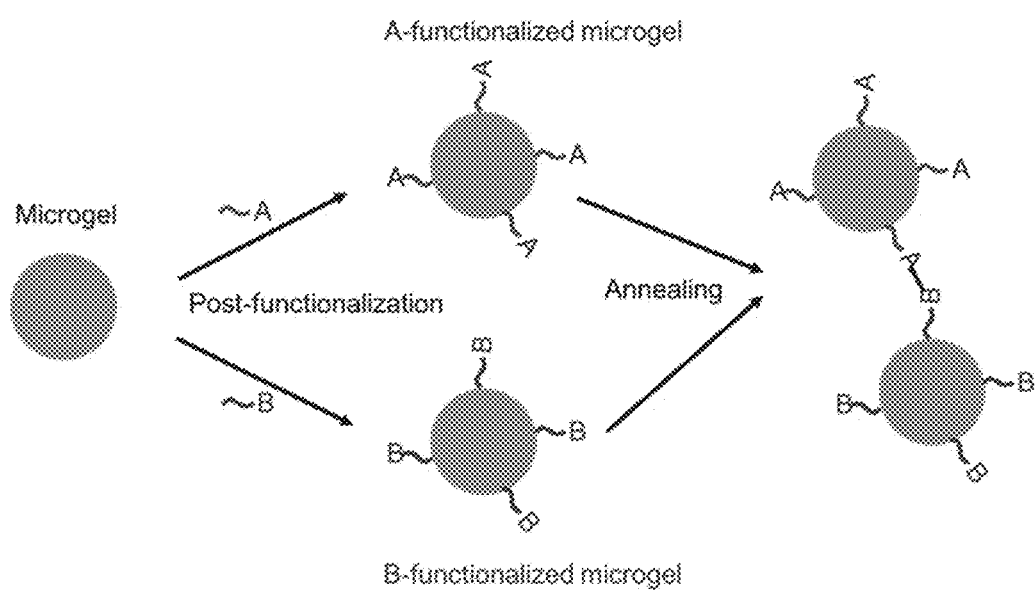
FIG. 5 shows an exemplary schematic representation of post-functionalization of flowable microgel particles.

In some instances, methods disclosed herein comprise synthesizing a flowable microgel particle and subsequently connecting an annealing component on to the microgel particle. This may be referred to as post-functionalization of the flowable microgel particles. A schematic diagram is presented in FIG. 5 to depict an example of post-functionalization of flowable microgel particles. In some instances, the methods comprise adding a first annealing component (A in FIG. 5) to a first flowable microgel particle and adding a second annealing component (B in FIG. 5) on to a second flowable microgel particle. Subsequently, the first flowable microgel particle (e.g., first functionalized microparticle) is mixed with the second flowable microgel particle (e.g., second functionalized microparticle) to anneal the first flowable microgel particle and the second flowable microgel particle via the first annealing component and second annealing component. Non-limiting examples of connections that can be formed between a first annealing component and a second annealing component include a covalent bond (e.g., amide, ester, C—C bond through Michael addition, carbamate, disulfide bond, oxime, thiourea, hydrazone, imine), a non-covalent bond through interaction such as (e.g., electrostatic interactions, hydrogen bonding, cation-π, π-π stacking, metal-ligand binding, van der Waals interactions). Another non-limiting example of an interaction that links or connects a first annealing component and a second annealing component is a non-covalent host-guest inclusion complex (driven by electrostatic interactions, hydrogen bonding, cation-π, π-π stacking, metal-ligand binding, or van der Waals interactions). In some instances, the first flowable microgel particle and the second flowable microgel particle are mixed immediately before microgel application (e.g., in a subject). In some instances, the first flowable microgel particle and the second flowable microgel particle are mixed during microgel application (e.g., from a multi-barrel syringe applied directly to a subject). In some instances, annealing occurs in situ. In some instances, the mixture anneals in situ to form a porous network. In some instances, annealing occurs in vitro.

A non-limiting example of post-functionalization, as described herein, is flowable microgel particles functionalized with DOPA reacting with flowable microgel particles functionalized with phenylboronic acid. Complexation of these flowable microgel particles form cyclic boronate esters, thereby creating a microporous scaffold. Another non-limiting example is flowable microgel particles functionalized with beta-cyclodextrin interacting with flowable microgel particles functionalized with adamantane. Complexation of these flowable microgel particles form a host-guest inclusion complex, thereby creating a microporous scaffold. In some instances, post-functionalization is advantageous because it allows more functionality options than pre-functionalization. Post-functionalization may not be as simple and easy as pre-functionalization as it may require an extra step after particle synthesis. However, some annealing components cannot be added with the pre-functionalization method. For instance, some annealing components are unstable during particle synthesis and cannot be used to pre-functionalize, but can be added after particle synthesis (post-functionalization). So the post-functionalization may allow one to functionalize flowable microgel particles with a wider array of annealing components.

Figure 6:
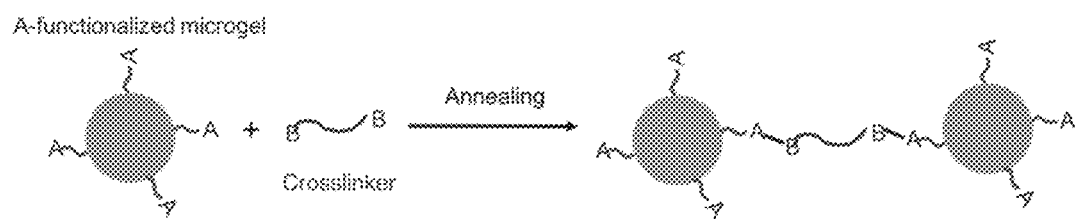
FIG. 6 shows an exemplary schematic representation of in situ addition of a crosslinking agent.

In some instances, methods disclosed herein comprise annealing a first functionalized microgel particle to a second functionalized microgel particle using a crosslinker. At least one of the first functionalized microgel particle and the second functionalized microgel particle may be a pre-functionalized microgel particle, as described herein. At least one of the first functionalized microgel particle and the second functionalized microgel particle may be a post-functionalized microgel particle, as described herein. In some instances, the first functionalized microgel particle and the second functionalized microgel particle are the same. In some instances, the first functionalized microgel particle and the second functionalized microgel particle are different. A schematic diagram is presented in FIG. 6 to depict an example of annealing flowable microgel particles with the use of a crosslinker. In some instances, methods disclosed herein comprise crosslinking the first functionalized microgel particle to the second functionalized microgel particle, wherein the crosslinking comprises linking at least one of the first functionalized microgel particle and the second functionalized microgel particle with a crosslinker (B in FIG. 6). In some instances, the methods comprise contacting at least one of the first functionalized microgel particle and the second functionalized microgel particle with a crosslinker after synthesizing the flowable microgel particles. In some instances, the contacting occurs in situ. In some instances, the contacting occurs in situ when the flowable microgel particles are being applied to tissue of a subject. The crosslinker may be functionalized with two or more functional groups. Non-limiting examples of crosslinker functional groups are vinyl sulfone, thiol, amine, imidazole, aldehyde, ketone, hydroxyl, azide, alkyne, vinyl, alkene, maleimide, carboxyl, N-Hydroxysuccinimide (NHS) ester, isocyanate, isothiocyanate, hydroxylamine, and thione. The crosslinker can be homofunctional (same functional groups) or heterofunctional (different functional groups). Examples of crosslinking reactions using crosslinkers, include, but are not limited to, Michael addition, amide bond coupling, "click" chemistry (e.g. Diels-Alder cycloaddition, Huisgen 1,3-dipolar cycloaddition), reductive amination, carbamate linkage, ester linkage, thioether linkage, disulfide bond, hydrazone bond, oxime coupling, and thiourea coupling.

Figure 7:
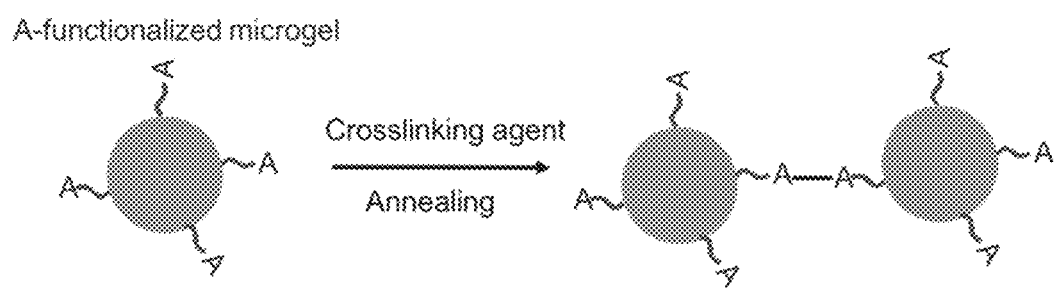
FIG. 7 shows an exemplary schematic representation of in situ addition of a crosslinking agent.

In some instances, methods disclosed herein comprise annealing a first functionalized microgel particle to a second functionalized microgel particle, using a crosslinking agent. See, e.g., FIG. 7. At least one of the first functionalized microgel particle and the second functionalized microgel particle may be a pre-functionalized microgel particle, as described herein. At least one of the first functionalized microgel particle and the second functionalized microgel particle may be a post-functionalized microgel particle, as described herein. In some instances, the first functionalized microgel particle and the second functionalized microgel particle are the same. In some instances, the first functionalized microgel particle and the second functionalized microgel particle are different. In some instances, the crosslinking agent is added after synthesizing the functionalized microgel particles. In some instances, the crosslinking agent is added during in situ application of the microgel particles to the tissue. In some instances, the crosslinking agent is a reducing agent. Non-limiting examples of reducing agents are dithiothreitol, dithioerythritol, L-glutathione, and tris (2-carboxyethyl) phosphine hydrochloride). In some instances, the crosslinking agent is an oxidizing agent. The oxidizing agent may be a metal complexing agent. The oxidizing agent may be a catalyst. Non-limiting examples of oxidizing agents are horseradish peroxidase (HRP), sodium periodate, and silver nitrate. In some instances, the crosslinking agent induces self-crosslinking of the annealing components present on the flowable microgel particles. The resulting crosslinkage may comprise at least one of a covalent bond, a coordination complex, a hydrogen bonding, an electrostatic interaction, a cation-π interaction, a π-π stacking, and a van der Waals interaction. By way of non-limiting example, DOPA-functionalized microgel particles may be crosslinked using silver nitrate as an oxidizing agent, wherein silver nitrate oxidizes the catechol of the DOPA moieties into reactive quinones that can further react with another DOPA group.

In some instances, methods comprise in situ triggered release of a crosslinker. In some instances, methods comprise in situ triggered release of an annealing agent. Functionalized microgel particles, as described herein, may be annealed using a crosslinker, annealing agent, or a crosslinking agent described herein that is released upon a trigger during in situ application of the flowable microgel particles to the tissue. Functionalized microgel particles, as described herein, may be annealed using a crosslinker, annealing agent or crosslinking agent described herein that is released upon a trigger after in situ application of the flowable microgel particles to the tissue. In some instances, a crosslinker, annealing agent or crosslinking agent is entrapped in a nanoparticle which is embedded in a microgel particle during microparticle synthesis. In some instances, the annealing agent, crosslinker or crosslinking agent is released by an internal trigger. Non-limiting examples of internal triggers are tissue mediated hydrolysis, enzyme mediated hydrolysis, hydrolysis not mediated by tissue or enzymes, enzymolysis, redox change (e.g. oxidative stress), pH change, and temperature change. In some instances, the annealing agent, crosslinker or crosslinking agent is released by an external trigger. Non-limiting examples of external triggers are temperature, light, electromagnetic field, and ultrasound.

Methods of producing microporous gel systems disclosed herein may comprise incorporating a therapeutic agent into a scaffold. Incorporating the therapeutic agent may comprise diffusing the therapeutic agent into a collection of flowable microgel particles. Incorporating the therapeutic agent may comprise attaching the therapeutic agent to the flowable microgel particles. The therapeutic agent may be attached to a flowable microgel particle via a covalent bond. The therapeutic agent may be attached to a flowable microgel particle via a non-covalent bond. Incorporating the therapeutic agent may comprise photo-caging the therapeutic agent to the microparticles.

Further provided herein are methods of producing a microporous gel system disclosed herein, comprising encapsulating a therapeutic agent in a nanoparticle, and mixing the therapeutic agent and the nanoparticle with flowable microgel particles. The nanoparticle and the therapeutic agent may be lyophilized. Methods may comprise dissolving the nanoparticle and the therapeutic agent (e.g., in an aqueous buffer) prior to mixing the nanoparticle and the therapeutic agent with the flowable microgel particles.

Methods of Treatment and Uses

Provided herein are methods of treating a site of a medical device in a tissue of a subject comprising administering to the site: a collection of flowable microgel particles comprising a backbone polymer and an annealing component; an annealing agent that links the flowable microgel particles together via the annealing component to form a stabilized scaffold of microgel particles having interstitial spaces therein. The medical device may be any medical device disclosed herein. The medical device may be a surgical device, a medical implant or a biomaterial disclosed herein.

Provided herein are methods of treating a cardiac arrhythmia comprising administering to a chest region of a subject in need thereof a medical device, wherein the medical device is a cardiac implantable electronic device; a collection of flowable microgel particles comprising a backbone polymer and an annealing component; and an annealing agent that links the flowable microgel particles together via the annealing component to form a stabilized scaffold of microgel particles having interstitial spaces therein.

Provided herein are methods of treating a neurological condition, comprising administering to a spinal region or a brain region of a subject in need thereof, a medical device, wherein the medical device is a neural implantable electronic device; a collection of flowable microgel particles comprising a backbone polymer and an annealing component; and an annealing agent that links the flowable microgel particles together via the annealing component to form a stabilized scaffold of microgel particles having interstitial spaces therein.

The methods comprise administering the medical device to a tissue of the subject. The tissue may be skin. The tissue may be muscle. The tissue may be fascia. The tissue may be brain tissue. The tissue may be intestinal tissue. The tissue may be adipose tissue. The tissue may also be characterized as a tissue at a location of the subject. The location may a brain, a skull, a spine, an ear, an eye, a nasal sinus, a neck, a chest, an abdomen, a stomach, a shoulder, a hip, a pelvis, a leg, an arm, a knee, an elbow, a hand, a foot, a heart, an organ.

The methods may comprise administering the collection of flowable microgel particles to the site before the medical device contacts the site. The methods may comprise administering the collection of flowable microgel particles to the site after the medical device contacts the site. The methods may comprise co-administering the collection of flowable microgel particles and the medical device to the site. The methods may comprise administering the annealing agent to the site before administering the flowable microgel particles to the site. The methods may comprise administering the annealing agent to the site after administering the flowable microgel particles to the site. The methods may comprise co-administering the collection of flowable microgel particles and the annealing agent to the site. The collection of flowable microgel particles and the annealing agent may be coating the device or contained in and/or on the medical device before the medical device is implanted.

The methods may comprise administering a therapeutic agent disclosed herein, a backbone polymer disclosed herein, a degradable crosslinker disclosed herein, a cell adhesive peptide, or any combination thereof, to the site. The methods may comprise administering the therapeutic agent, the degradable crosslinker, the cell adhesive peptide, or any combination thereof, to the site after, before or concurrently with the medical device, flowable microgel particles or annealing agent. The methods may comprise applying the therapeutic agent, the degradable crosslinker, the cell adhesive peptide, or any combination thereof, to the medical device.

The methods may comprise applying a stimulus to the site, wherein the stimulus forms the stabilized scaffold. By way of non-limiting example, the stimulus may be a chemical, an enzyme, an agent that alters the pH of the site or the microporous gel system, a redox stress, heat, cold, magnetic field, light, ultrasound, electrical field, radiation, and combinations thereof. Although the effects of the stimulus may last longer, the stimulus may be applied for about 1 second, about 2 seconds, about 3 seconds, about 4 seconds, about 5 seconds, about 10 seconds, about 30 seconds, about 1 minute, about 2 minutes, about 5 minutes, about 10 minutes, about 15 minutes, about 20 minutes, about 30 minutes, about 1 hour, about 2 hours, about 8 hours, about 12 hours, or about 1 day. The stimulus may be applied for 1 second, 2 seconds, 3 seconds, 4 seconds, 5 seconds, 10 seconds, 30 seconds, 1 minute, 2 minutes, 5 minutes, 10 minutes, 15 minutes, 20 minutes, 30 minutes, 1 hour, 2 hours, 8 hours, 12 hours, or 1 day. In some cases, the stimulus is applied for more than one day. The stimulus may be applied for about 1 second to about 1 day. The stimulus may be applied for about 5 seconds to about 1 day. The stimulus may be applied for about 10 seconds to about 1 day. The stimulus may be applied for about 30 seconds to about 1 day. The stimulus may be applied for about 1 minute to about 1 day. The stimulus may be applied for about 5 minutes to about 1 day. The stimulus may be applied for about 15 minutes to about 1 day. The stimulus may be applied for about 30 minutes to about 1 day. The stimulus may be applied for about 1 hour to about 1 day. The stimulus may be applied for 1 second to 1 day. The stimulus may be applied for 5 seconds to 1 day. The stimulus may be applied for 10 seconds to 1 day. The stimulus may be applied for 30 seconds to 1 day. The stimulus may be applied for 1 minute to 1 day. The stimulus may be applied for 5 minutes to 1 day. The stimulus may be applied for 15 minutes to 1 day. The stimulus may be applied for 30 minutes to 1 day. The stimulus may be applied for 1 hour to 1 day. The stimulus may be applied for about 1 second to about 12 hours. The stimulus may be applied for about 5 seconds to about 12 hours. The stimulus may be applied for about 10 seconds to about 12 hours. The stimulus may be applied for about 30 seconds to about 12 hours. The stimulus may be applied for about 1 minute to about 12 hours. The stimulus may be applied for about 5 minutes to about 12 hours. The stimulus may be applied for about 15 minutes to about 12 hours. The stimulus may be applied for about 30 minutes to about 12 hours. The stimulus may be applied for about 1 hour to about 12 hours. The stimulus may be applied for 1 second to 12 hours. The stimulus may be applied for 5 seconds to 12 hours. The stimulus may be applied for 10 seconds to 12 hours. The stimulus may be applied for 30 seconds to 12 hours. The stimulus may be applied for 1 minute to 12 hours. The stimulus may be applied for 5 minutes to 12 hours. The stimulus may be applied for 15 minutes to 12 hours. The stimulus may be applied for 30 minutes to 12 hours. The stimulus may be applied for 1 hour to 12 hours. The stimulus may be applied for about 1 second to about 1 hour. The stimulus may be applied for about 5 seconds to about 1 hour. The stimulus may be applied for about 10 seconds to about 1 hour. The stimulus may be applied for about 30 seconds to about 1 hour. The stimulus may be applied for about 1 minute to about 1 hour. The stimulus may be applied for about 5 minutes to about 1 hour. The stimulus may be applied for about 15 minutes to about 1 hour. The stimulus may be applied for about 30 minutes to about 1 hour. The stimulus may be applied for about 1 hour to about 1 hour. The stimulus may be applied for 1 second to 1 hour. The stimulus may be applied for 5 seconds to 1 hour. The stimulus may be applied for 10 seconds to 1 hour. The stimulus may be applied for 30 seconds to 1 hour. The stimulus may be applied for 1 minute to 1 hour. The stimulus may be applied for 5 minutes to 1 hour. The stimulus may be applied for 15 minutes to 1 hour. The stimulus may be applied for 30 minutes to 1 hour.

Methods of treatment and uses described herein may result in a tissue remodeling or cellular effect in the subject. In some instances, use of microporous gel system to microporous scaffold disclosed herein results in eliminating inflammation at a wound or surgical site. Elimination of inflammation may be evidenced by an absence of MNGC at the wound or surgical site. Elimination of inflammation may be evidenced by a similar number of MNGC at the wound or surgical site as compared to a non-wound site (e.g., healthy, non-damaged tissue). Elimination of inflammation may be evidenced by a reduction or absence of neutrophils or macrophages at the wound or surgical site. Elimination of inflammation may be evidenced by a similar number of neutrophils or macrophages at the wound or surgical site as compared to a non-wound site (e.g., healthy, non-damaged tissue). In some instances, tissue of the subject integrates with the microporous scaffold. In some instances, at least a portion of the microporous scaffold degrades in situ. In some instances, at least about 10% of the microporous scaffold degrades in situ. In some instances, at least about 30% of the microporous scaffold degrades in situ. In some instances, at least about 60% of the microporous scaffold degrades. In some instances, at least about 90% of the microporous scaffold degrades in situ. In some instances, the microporous scaffold completely degrades in situ. In some instances, at least one of a wound site and a microporous scaffold is vascularized after administration of a gel disclosed herein. Vascularization may result in the presence of large vessels with intimal walls. Large vessels may be vessels, wherein at least a portion of the blood vessel has a diameter greater than about 10 µm. In some instances, the wound site develops a web-like dermal tissue, which indicates non-fibrous tissue formation. In some instances, the wound site does not develop fibrous tissue.

The extent of any tissue remodeling or cellular effect described herein, (e.g., elimination of inflammation, integration of tissue, degradation of the microporous scaffold, and vascularization of the microporous scaffold), may occur within a time range from the time the gel was administered. The time range may depend upon the tissue to which the microporous scaffold is administered. The time range may be about 5 days to about 10 days. The time range maybe about 10 days to about 20 days. The time range may be about 20 days to about 30 days. The time range may be about 30 days to about 40 days. The time range may be about 40 days to about 50 days. The time range may be about 50 days to about 100 days.

Methods of administering a microporous gel system and device to a subject may result in microgel particle—substrate annealing, wherein a bond forms between a flowable microgel particle and a substrate (medical device or tissue of the subject). The bond can be covalent. The bond can be non-covalent. In some instances, the bond forms between a flowable microgel particle and a device coating. In some instances, the medical device is pre-coated with a functional group that is capable of binding to at least one flowable microgel particle of a collection of flowable microgel particles. In some instances, the substrate binds to a first layer of flowable microgel particles, the latter of which binds to a second layer of microgel particles. The first layer of flowable microgel particles may comprise the same type of flowable microgel particles as the second layer of flowable microgel particles. The first layer of flowable microgel particles may comprise a different type of flowable microgel particles as the second layer of flowable microgel particles. In some instances, microgel particle-substrate annealing occurs simultaneously with particle-particle annealing. In some instances, microgel particle-substrate annealing occurs before particle-particle annealing. In some instances, microgel particle-substrate annealing occurs after particle-particle annealing.

Diseases and Conditions

Provided herein are methods and systems for the treatment of a condition or disease in a subject, comprising administering any combination of microporous gel systems, medical devices and therapeutic agents disclosed herein. The condition or disease may be an acute condition or disease. By way of non-limiting example, the acute condition or disease may be a dermal wound, a deep surgical wound, an amputation, or a stroke. The condition or disease may be a chronic condition or disease. By way of non-limiting example, the chronic condition or disease may be a non-healing wound, heart arrhythmia, epilepsy, or osteoarthritis. The condition or disease may be a degenerative disease. By way of non-limiting example, the degenerative disease may be a neurodegenerative disease (e.g., Alzheimer's, Parkinson's or multiple sclerosis) or a cancer. The condition or disease may be a metabolic condition or disease (e.g., diabetes). By way of non-limiting example, the metabolic condition or disease may be diabetes or obesity. The condition or disease may be an orthopedic disorder (e.g., musculoskeletal trauma, arthritis, fractures, infections, osteoporosis, ligament injuries).

Provided herein are methods and systems for the treatment of a cardiovascular condition, a cardiovascular disease, a heart condition or a heart disease disclosed herein. A cardiovascular condition or cardiovascular disease is a condition or disease wherein vasculature of the subject is affected. The heart condition or heart disease may be a condition or disease that affects the function of the heart, such as the electrical function, pumping function or valve function, without affecting the health of the vasculature of the heart or cardiovascular system. The methods and systems disclosed herein provide for treatment of both heart and cardiovascular diseases and conditions, and combinations thereof. However, these terms may be used interchangeably herein, unless otherwise specified. Heart conditions include, but are not limited to atrial fibrillation, ventricular fibrillation, chronic heart failure, coronary artery disease, myocarditis, peripheral arterial occlusive disease, cardiomyopathy, pericarditis, myocarditis, endocarditis, a congenital heart defect, atherosclerosis, and combinations thereof. Heart conditions include cardiac arrhythmias. The cardiac arrhythmia may be acute. The cardiac arrhythmia may be chronic. The cardiac arrhythmia may be environmentally induced. The cardiac arrhythmia may be exercise induced. The cardiac arrhythmia may be caused by a genetic mutation. The cardiac arrhythmia may be caused by an infection.

Provided herein are methods and systems for the treatment of a neurological disease or a neurological condition disclosed herein. The neurological condition may be chronic. The neurological condition may be acute. The neurological condition may be due to an injury. By way of non-limiting example, the neurological disease or neurological condition may be Parkinson's Disease, Alzheimer's Disease, tremor, dystonia, chronic pain, major depression, obsessive compulsive disorder, schizophrenia, epilepsy, addictions, stroke, multiple sclerosis, traumatic brain injury, spinal cord injury, encephalitis, cerebral ischemia, or an intestinal condition. The neurological condition may be speech defect, hearing defect, paralysis, or partial-paralysis.

Various embodiments contemplated herein may include, but need not be limited to, one or more of the following, and combinations thereof:

Embodiment 1

A system comprising: a collection of flowable microgel particles, wherein the flowable microgel particles comprise a backbone polymer; at least one annealing component; and a medical device, wherein the flowable microgel particles are capable of being linked together via the at least one annealing component to form a stabilized scaffold having interstitial spaces therein.

Embodiment 2

A system comprising: a collection of flowable microgel particles, wherein the flowable microgel particles comprise a backbone polymer; at least one annealing component; and a medical device, wherein the flowable microgel particles are linked together via the at least one annealing component to form a stabilized scaffold having interstitial spaces therein.

Embodiment 3

The system of embodiment 1 or 2, comprising an intercrosslinker that links the flowable microgel particles together via the at least one annealing component.

Embodiment 4

The system of embodiment 1 or 2, comprising an annealing agent that links the flowable microgel particles together via the at least one annealing component.

Embodiment 5

The system of embodiment 4, wherein the annealing agent is an intercrosslinking agent.

Embodiment 6

The system of embodiment 1 or 2, comprising a first annealing component and a second annealing component.

Embodiment 7

The system of embodiment 6, wherein the first annealing component and the second annealing component are the same.

Embodiment 8

The system of embodiment 6, wherein the first annealing component and the second annealing component are different.

Embodiment 9

The system of embodiment 1 or 2, wherein the at least one annealing component is a substrate for an enzyme of a mammalian subject.

Embodiment 10

The system of embodiment 1 or 2, a first annealing component and a second annealing component are linked together when exposed to a condition in a mammalian subject.

Embodiment 11

The system of any one of embodiments 1-10, wherein the medical device is a medical implant.

Embodiment 12

The system of any one of embodiments 1-10, wherein the medical device comprises an electrode.

Embodiment 13

The system of any one of embodiments 1-10, wherein the medical device comprises an electrical component.

Embodiment 14

The system of any one of embodiments 1-10, wherein the medical device comprises a coating, wherein the coating comprises at least one of the annealing component and an annealing agent.

Embodiment 15

The system embodiment 11, wherein the medical implant is a cardiac implantable electronic device.

Embodiment 16

The system of embodiment 15, wherein the cardiac implantable electronic device is a pacemaker.

Embodiment 17

The system of embodiment 15, wherein the cardiac implantable electronic device is a defibrillator.

Embodiment 18

The system of embodiment 11, wherein the medical implant is a neural implantable electronic device.

Embodiment 19

The system of embodiment 1 or 2, wherein the stabilized scaffold maintains placement of the medical device in a surgical void of a subject.

Embodiment 20

The system of embodiment 2, wherein the stabilized scaffold has a custom form determined by the medical device and the surgical void.

Embodiment 21

The system of embodiment 2, wherein the stabilized scaffold comprises non-covalent bonds between the flowable microgel particles.

Embodiment 22

The system of embodiment 2, wherein the stabilized scaffold comprises covalent bonds between the flowable microgel particles.

Embodiment 23

The system of any preceding embodiment, comprising a therapeutic agent.

Embodiment 24

The system of embodiment 23, wherein the therapeutic agent is an anti-inflammatory agent, an antimicrobial agent, or an analgesic.

Embodiment 25

The system of embodiment 23, wherein the therapeutic agent is incorporated in the stabilized scaffold.

Embodiment 26

The system of embodiment 2, comprising a therapeutic agent, wherein the stabilized scaffold releases the therapeutic agent from the stabilized scaffold when the stabilized scaffold is present in a mammalian subject.

Embodiment 27

The system of embodiment 26, wherein the stabilized scaffold releases at least a portion of the therapeutic agent from the stabilized scaffold in less than one day from its initial presence in the mammalian subject.

Embodiment 28

The system of embodiment 26, wherein the stabilized scaffold releases the therapeutic agent from the stabilized scaffold over a period of less than 1 day to 100 days.

Embodiment 29

The system of embodiment 25, comprising a therapeutic agent releasing agent that releases the therapeutic agent from the stabilized scaffold.

Embodiment 30

The system of embodiment 25, wherein the therapeutic agent is released by tissue mediated hydrolysis.

Embodiment 31

The system of embodiment 25, wherein the therapeutic agent is released by passive hydrolysis.

Embodiment 32

The system of embodiment 25, wherein the therapeutic agent is released by a temperature change.

Embodiment 33

The system of any preceding embodiment, comprising a nanoparticle.

Embodiment 34

The system of embodiment 33, wherein the therapeutic agent is connected to or contained within the nanoparticle.

Embodiment 35

The system of embodiment 33, wherein the nanoparticle is a mesoporous silica nanoparticle.

Embodiment 36

The system of embodiment 33, wherein the nanoparticle comprises poly(lactic-co-glycolic acid).

Embodiment 37

The system of embodiment 33, wherein the nanoparticle comprises chitosan.

Embodiment 38

The system of embodiment 33, wherein the nanoparticle comprises hyaluronic acid.

Embodiment 39

The system of embodiment 33, wherein the nanoparticle comprises a poly(anhydride), a poly(amide), a poly(ortho ester), a polycaprolactone, or a combination thereof.

Embodiment 40

The system of embodiment 33, wherein the nanoparticle comprises a polymer with a lower critical solution temperature (LCST).

Embodiment 41

The system of embodiment 40, wherein the polymer is poly(N-isopropylacrylamide) or a co-polymer thereof.

Embodiment 42

The system of embodiment 33, wherein the nanoparticle comprises a polymer with an upper critical solution temperature (UCST).

Embodiment 43

The system of embodiment 42, wherein the polymer is poly(hydroxyethylmethacrylate), polyethylene oxide, or poly(ethyleneoxide)-poly(propyleneoxide)-poly(ethyleneoxide).

Embodiment 44

The system of embodiment 33, wherein the nanoparticle comprises a self-immolating polymer.

Embodiment 45

The system of embodiment 44, wherein the polymer is poly(p-aminobenzyl oxycarbonyl).

Embodiment 46

The system of embodiment 44, wherein the polymer is capped with a cage that can be released upon a stimulus.

Embodiment 47

The system of embodiment 33, wherein the system comprises a core-shell nanoparticle system.

Embodiment 48

The system of embodiment 47, wherein a first portion of the flowable microgel particles comprises the core-shell nanoparticle system and wherein the second portion of flowable microgel particles comprises a shell-dissolving agent, wherein the shell-dissolving agent is capable of releasing the therapeutic agent when the first portion of the flowable microgel particles is in contact with the second portion of flowable microgel particles.

Embodiment 49

The system of embodiment 48, comprising a first container containing the first portion and a second container containing the second portion.

Embodiment 50

The system of embodiment 3, wherein the intercrosslinker is degradable in a mammalian subject.

Embodiment 51

The system of any preceding embodiment, comprising a cell adhesive peptide.

Embodiment 52

The system of embodiment 4, wherein the annealing agent comprises a light source.

Embodiment 53

The system of embodiment 1, wherein the collection of flowable microgel particles and annealing agent are stored or administered from a single container.

Embodiment 54

The system of embodiment 1, wherein at least two of the flowable microgel particles are present in separate containers.

Embodiment 55

The system of embodiment 8, wherein the first annealing component and the second annealing component are present in separate containers.

Embodiment 56

The system of embodiment 1, comprising an application device, wherein the application device is configured to apply the flowable microgel particles and the at least one annealing component to a tissue of a subject.

Embodiment 57

The system of embodiment 56, wherein the application device comprises a syringe, a spatula, a squeezable tube or a cannula.

Embodiment 58

The system of embodiment 56, wherein the application device comprises a multi-barrel syringe, and wherein at least a first portion of the flowable microgel particles or a first portion of the annealing component is in a first barrel, and a second portion of the flowable microgel particles or a second portion of the annealing component is in a second barrel.

Embodiment 59

The system of embodiment 1, wherein the microporous gel system has a shelf life of at least about one year at room temperature.

Embodiment 60

A system according to any one of embodiments 1-59 for use in the treatment of a wound or surgical site.

Embodiment 61

A method of treating a site of a medical device in a tissue of a subject comprising administering to the site: a collection of flowable microgel particles, wherein the flowable microgel particles comprise a backbone polymer; at least one annealing component and a medical device, wherein the flowable microgel particles are capable of being linked together via the at least one annealing component to form a stabilized scaffold having interstitial spaces therein.

Embodiment 62

A method of reducing or preventing fibrosis at a site of a medical device in a tissue of a subject comprising administering to the site: a collection of flowable microgel particles, wherein the flowable microgel particles comprise a backbone polymer; at least one annealing component; and a medical device, wherein the flowable microgel particles are capable of being linked together via the at least one annealing component to form a stabilized scaffold having interstitial spaces therein.

Embodiment 63

A method of reducing or preventing inflammation at a site of a medical device in a tissue of a subject comprising administering to the site: a collection of flowable microgel particles, wherein the flowable microgel particles comprise a backbone polymer; at least one annealing component; and a medical device, wherein the flowable microgel particles are capable of being linked together via the at least one annealing component to form a stabilized scaffold having interstitial spaces therein.

Embodiment 64

The method of any one of embodiments 61 to 63, wherein the medical device is a surgical device.

Embodiment 65

The method of any one of embodiments 61 to 63, wherein the medical device is a medical implant.

Embodiment 66

The method of any one of embodiments 61 to 63, comprising administering at least one of the annealing component and the flowable microgel particles to the site before administering the medical device to the site.

Embodiment 67

The method of any one of embodiments 61 to 63, comprising administering at least one of the annealing component and the flowable microgel particles to the site after administering the medical device to the site.

Embodiment 68

The method of any one of embodiments 61 to 63, comprising co-administering at least one of the annealing component and the flowable microgel particles, and the medical device to the site.

Embodiment 69

The method of any one of embodiments 61 to 63, comprising administering at least one of the annealing component and the flowable microgel particles with a syringe, cannula, squeezable tube or spatula.

Embodiment 70

The method any one of embodiments 61 to 69, comprising administering an annealing agent.

Embodiment 71

The methods of embodiment 70, comprising administering the annealing agent before administering at least one of the annealing component and the flowable microgel particles.

Embodiment 72

The method of embodiment 70, comprising administering the annealing agent after administering at least one of the annealing component and the flowable microgel particles.

Embodiment 73

The method of embodiment 70, comprising co-administering the annealing agent and at least one of the annealing component and the flowable microgel particles.

Embodiment 74

The method of any one of embodiments 61-73, comprising administering a therapeutic agent to the site.

Embodiment 75

The method of embodiment 74, comprising administering a therapeutic agent releasing agent to the site, wherein the therapeutic agent releasing agent releases the therapeutic agent from the stabilized scaffold to the site or tissue.

Embodiment 76

The method of embodiment 74, comprising incorporating the therapeutic agent into the stabilized scaffold.

Embodiment 77

The method of embodiment 74, wherein the stabilized scaffold comprises a core-shell nanoparticle system wherein the therapeutic agent is connected to or contained within the core-shell nanoparticle system, comprising applying an external stimulus to the stabilized scaffold to release the therapeutic agent to the site or tissue.

Embodiment 78

The method of embodiment 77, wherein the external stimulus selected from light, electromagnetic radiation, or temperature change.

Embodiment 79

The method of embodiment 61, comprising changing a condition of the site after formation of the stabilized scaffold.

Embodiment 80

The method of embodiment 61, comprising changing a condition of the site before formation of the stabilized scaffold.

Embodiment 81

The method of embodiment 79 or 80, wherein changing the condition comprises at least one of changing temperature of the site, changing pH of the site, changing chemistry of the site, applying an exogenous enzyme, activating an endogenous enzyme, applying a magnetic field, applying a form of radiation, applying light, and applying ultrasound.

Embodiment 82

A method of treating a heart condition comprising administering to a subject in need thereof: a collection of flowable microgel particles, wherein the flowable microgel particles comprise a backbone polymer; at least one annealing component; and a cardiac implantable electronic device, wherein the flowable microgel particles are capable of being linked together via the at least one annealing component to form a stabilized scaffold having interstitial spaces therein.

Embodiment 83

The method of embodiment 82, wherein the heart condition is a heart arrhythmia.

Embodiment 84

The method of embodiment 82, wherein the heart condition is a sustained ventricular tachycardia.

Embodiment 85

The method of embodiment 82, wherein the heart condition is a ventricular fibrillation.

Embodiment 86

A method of treating a neurological condition comprising administering to a subject in need thereof: a collection of flowable microgel particles, wherein the flowable microgel particles comprise a backbone polymer; at least one annealing component; and a neural implantable electronic device, wherein the flowable microgel particles are capable of being linked together via the at least one annealing component to form a stabilized scaffold having interstitial spaces therein.

Embodiment 87

A method of producing a microporous scaffold, comprising: synthesizing a first portion of flowable microgel particle in the presence of a first annealing component and a second annealing component, wherein there is more of the first annealing component than the second annealing component to produce a first functionalized microgel particle; synthesizing a second portion of flowable microgel particle in the presence of the first annealing component and the second annealing component, wherein there is more of the second annealing component than the first annealing component to produce a second functionalized microgel particle; combining the first functionalized microgel particle and the second functionalized microgel particle such that the first functionalized microgel particle and the second functionalized microgel particle connect, thereby producing a microporous scaffold of microgel particles having interstitial spaces therebetween.

Embodiment 88

The method of embodiment 87, wherein there is at least 1% more of the first annealing component than the second annealing component in step (a).

Embodiment 89

The method of embodiment 87, wherein there is at least 1% more of the second annealing component than the first annealing component in step (b).

Embodiment 90

The method of embodiment 87, wherein at least one of the first annealing component and the second annealing component comprise a functional group selected from a vinyl sulfone, thiol, amine, imidazole, aldehyde, ketone, hydroxyl, azide, alkyne, vinyl, alkene, maleimide, carboxyl, N-hydroxysuccinimide (NHS) ester, isocyanate, isothiocyanate, hydroxylamine, and thione.

Embodiment 91

The method of embodiment 87, wherein the first functionalized microgel particle and the second functionalized microgel particle connect through a reaction selected from Michael addition, amide bond coupling, Diels-Alder cycloaddition, Huisgen 1,3-dipolar cycloaddition, reductive amination, carbamate linkage, ester linkage, thioether linkage, disulfide bonding, hydrazone bonding, oxime coupling, and thiourea coupling.

Embodiment 92

The method of embodiment 87, wherein the first functionalized microgel particle and the second functionalized microgel particle connect to produce a covalent bond.

Embodiment 93

The method of embodiment 87, wherein the first functionalized microgel particle and the second functionalized microgel particle connect to produce a non-covalent bond.

Embodiment 94

The method of embodiment 87, wherein the first functionalized microgel particle and the second functionalized microgel particle connect to produce a connection selected from a C—C bond, an amide bond, an amine bond, a carbamate linkage, an ester linkage, a thioether linkage, a disulfide bond, a hydrazine bond, an oxime coupling and a thiourea coupling.

Embodiment 95

The method of embodiment 87, wherein at least one step of the method is performed in situ.

Embodiment 96

A method of producing a microporous scaffold, comprising: synthesizing flowable microgel particles; contacting a first portion of the flowable microgel particles with a first annealing component to produce a first functionalized microgel particle; contacting a second portion of the flowable microgel particles with a second annealing component to produce a second functionalized microgel particle; combining the first functionalized microgel particle and the second functionalized microgel particle such that the first functionalized microgel particle and the second functionalized microgel particle connect, thereby producing a microporous scaffold of microgel particles having interstitial spaces therebetween.

Embodiment 97

The method of embodiment 96, wherein at least one of the first annealing component and the second annealing component comprise a reactive moiety selected from a catechol, a sialic acid, a boronic acid, a molecular cage, adamantane, biotin, and streptavidin.

Embodiment 98

The method of embodiment 97, wherein the molecular cage is selected from a cyclodextrin, a cucurbituril, a calixarene, a pillararene, a crown ether, a cavitand, a cryptand, and a carcerand.

Embodiment 99

The method of embodiment 96, wherein the first functionalized microgel particle and the second functionalized microgel particle connect through a covalent bond.

Embodiment 100

The method of embodiment 99, wherein the covalent bond is selected from an amide, ester, C—C bond, carbamate, disulfide bond, oxime, thiourea, hydrazone, and imine.

Embodiment 101

The method of embodiment 96, wherein the first functionalized microgel particle and the second functionalized microgel particle connect through a non-covalent bond.

Embodiment 102

The method of embodiment 101, wherein the non-covalent bond is selected from an electrostatic interaction, a hydrogen bond, a cation-$\pi$, $\pi$-$\pi$ stack, a metal-ligand bond, a van der Waals interaction, and a non-covalent host-guest inclusion complex.

Embodiment 103

The method of embodiment 96, wherein at least one step of the method is performed in situ.

Embodiment 104

The method of any one of embodiments 87-103, comprising contacting the first functionalized microgel particle and the second functionalized microgel particle with an intercrosslinker in order to connect the first functionalized microgel particle and the second functionalized microgel particle.

Embodiment 105

The method of embodiment 104, wherein the contacting occurs in situ.

Embodiment 106

The method of embodiment 104, wherein the contacting occurs after synthesizing the flowable microgel particles.

Embodiment 107

The method of embodiment 104, wherein the intercrosslinker comprises at least one functional group.

Embodiment 108

The method of embodiment 104, wherein the intercrosslinker comprises at least two functional groups.

Embodiment 109

The method of embodiment 107 or 108, wherein at least one functional group is selected from a vinyl sulfone, a thiol, an amine, an imidazole, an aldehyde, a ketone, a hydroxyl, an azide, an alkyne, a vinyl, an alkene, a maleimide, a carboxyl, a N-Hydroxysuccinimide (NHS) ester, an isocyanate, an isothiocyanate, ahydroxylamine, and a thione.

Embodiment 110

The method of embodiment 104, wherein the connecting the first functionalized microgel particle and the second functionalized microgel particle comprises a reaction selected from Michael addition, amide bond coupling, Diels-Alder cycloaddition, Huisgen 1,3-dipolar cycloaddition, reductive amination, carbamate linkage, ester linkage, thioether linkage, disulfide bond, hydrazone bond, oxime coupling, and thiourea coupling.

Embodiment 111

The method of any one of embodiments 87-110, comprising contacting the first functionalized microgel particle and the second functionalized microgel particle with an intercrosslinking agent.

Embodiment 112

The method of embodiment 111, wherein the intercrosslinking agent comprises a reducing agent.

Embodiment 113

The method of embodiment 112, wherein the reducing agent comprises at least one of dithiothreitol, dithioerythritol, L-glutathione, and tris (2-carboxyethyl) phosphine hydrochloride.

Embodiment 114

The method of embodiment 110, wherein the intercrosslinking agent comprises an oxidizing agent.

Embodiment 115

The method of embodiment 114, wherein the oxidizing agent comprises at least one of horseradish peroxidase (HRP), sodium periodate, and silver nitrate.

Embodiment 116

The method of embodiment 111, wherein the intercrosslinking agent induces self-crosslinking of functional groups present on at least one of the annealing component flowable microgel particles or annealing components to produce a crosslinkage.

Embodiment 117

The method of embodiment 116, wherein the crosslinkage comprises at least one of a covalent bond, a coordination complex, a hydrogen bond, an electrostatic interaction, a cation-π interaction, a π-π stack, and a van der Waals interaction.

Embodiment 118

The method of embodiment 111, comprising contacting the first functionalized microgel particle and the second functionalized microgel particle with the intercrosslinking agent in situ.

Embodiment 119

The method of any one of embodiments 104-118, comprising applying an external stimulus to the microporous scaffold to release the intercrosslinker.

Embodiment 120

The method of embodiment 119, wherein applying an external stimulus to the microporous scaffold occurs indirectly by applying the external stimulus to tissue around the microporous scaffold.

Embodiment 121

The method of embodiment 119, wherein the external stimulus is selected from light, an electromagnetic field, ultrasound, heat, cooling, and a combination thereof.

Embodiment 122

The method of anyone of embodiments 87-121, comprising incorporating a therapeutic agent into the stabilized scaffold.

Embodiment 123

The method of embodiment 122, wherein incorporating comprises at least one of diffusing the therapeutic agent into the collection of flowable microgel particles; covalently linking the therapeutic agent to the flowable microgel particles; and photo-caging the therapeutic agent to the microgel particles.

Embodiment 124

The method of embodiment 122, wherein incorporating comprises encapsulating the therapeutic agent in a nanoparticle, and mixing the therapeutic agent and the nanoparticle with the flowable microgel particles.

Embodiment 125

The method of embodiment 124, wherein the nanoparticle and the therapeutic agent are lyophilized, comprising dissolving the nanoparticle and the therapeutic agent in aqueous buffer prior to mixing the nanoparticle and the therapeutic agent with the flowable microgel particles.

Embodiment 126

The method of embodiment 112, wherein transferring and removing occur substantially simultaneously.

Embodiment 127

A method of purifying flowable microgel particles comprising: obtaining a membrane filtration system; transferring flowable microgel particles from a first solvent to a second solvent, wherein the second solvent is immiscible with the first solvent, by controlled addition of a third solvent to the first solvent such that a single miscible phase containing the flowable microgel particles is maintained; and removing an impurity from the flowable microgel particles.

Embodiment 128

The method of embodiment 127, wherein transferring and removing occur substantially simultaneously.

Embodiment 129

The method of embodiment 127, wherein the membrane filtration system requires a single miscible phase for function.

Embodiment 130

The method of embodiment 127, wherein the membrane filtration system is selected from tangential flow filtration (TFF), ultrafiltration-diafiltration (UFDF), microfiltration-diafiltration (MFDF), or hollow-fiber-diafiltration (HFDF).

Embodiment 131

The method of embodiment 127, wherein the first solvent is a non-polar oil and the second solvent is water.

Embodiment 132

The method of embodiment 127, wherein the third solvent is an alcohol solution.

Embodiment 133

The method of embodiment 127, wherein the impurity is a surfactant.

Embodiment 134

A method of concentrating flowable microgel particles in a solution or suspension comprising: pumping the flowable microgel particles through a membrane filtration system while a continuous phase volume is removed; continually concentrating the flowable microgel particles at a controlled membrane flux; and maintaining a wall shear stress inside the membrane filtration system.

Embodiment 135

The method of embodiment 134, wherein the membrane filtration system is selected from tangential flow filtration (TFF), ultrafiltration-diafiltration (UFDF), microfiltration-diafiltration (MFDF), or hollow-fiber-diafiltration (HFDF).

Embodiment 136

The method of embodiment 134, wherein the membrane flux is controlled between 100 and 1000 L/m2h.

Embodiment 137

The method of embodiment 134, wherein the wall shear stress is maintained between 100 $s^{-1}$ and 10,000 $s^{-1}$.

EXAMPLES

The examples and embodiments described herein are for illustrative purposes only and are not intended to limit the scope of the claims provided herein. Various modifications or changes suggested to persons skilled in the art are to be included within the spirit and purview of this application and scope of the appended claims.

Example 1. Synthesis of Flowable Microgel Particles

Figure 8:
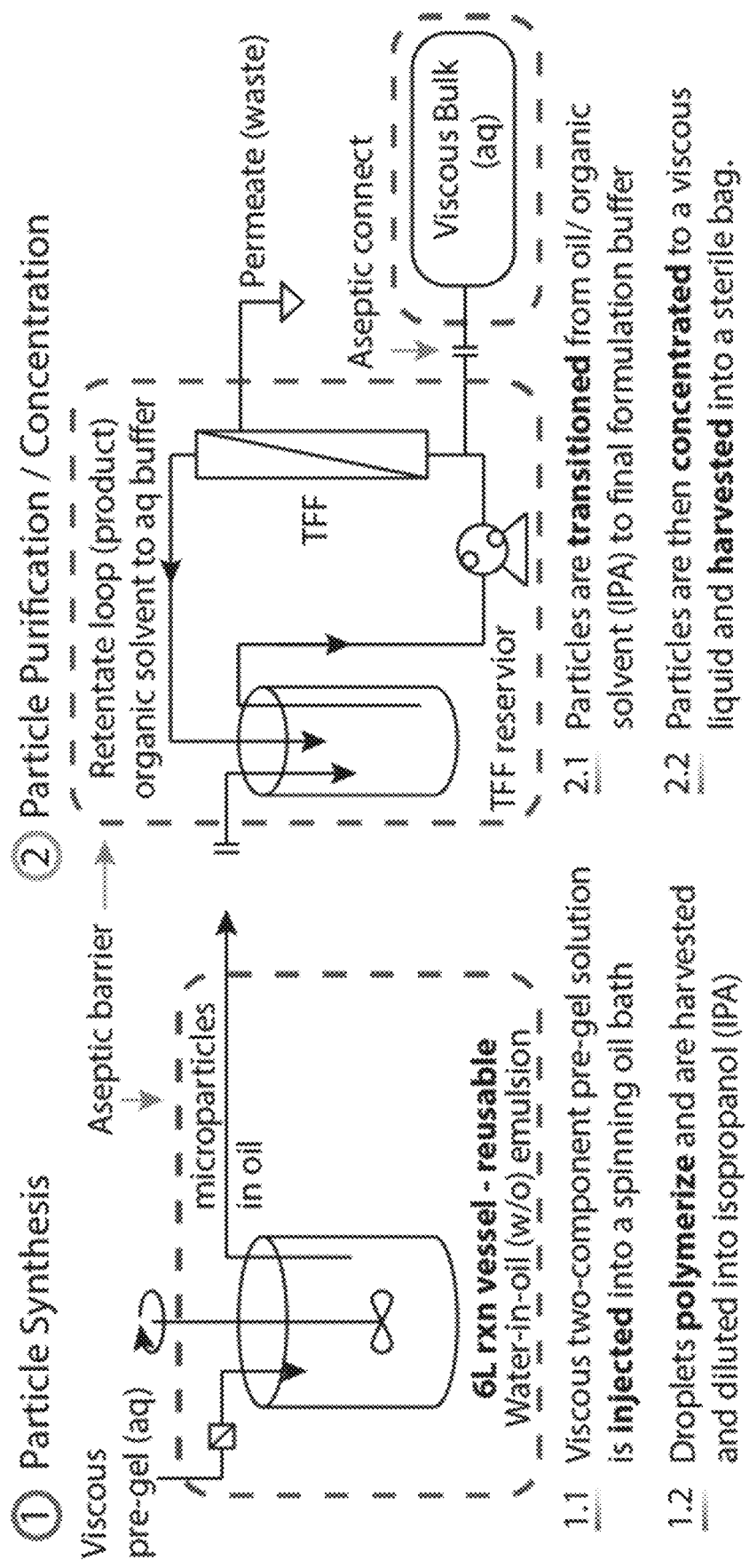
FIG. 8 shows an exemplary schematic diagram of flowable microgel particle synthesis by a water-in-oil emulsion and purification by tangential flow filtration.

Flowable microgel particles were synthesized by a water-in-oil emulsion and purified by tangential flow filtration (TFF) (see FIG. 8). The manufacturing process was performed aseptically. The reaction vessel, glassware, connectors, fittings, filters, tubing and TFF system were depyrogenated and then sterilized using a sterilization technique (e.g., gamma radiation or moist heat (autoclave)). All the prepared solutions were filtered prior to the addition to the reaction vessel. Buffers and solvents used for purification were added to a sterile bag through a 0.2 µm filter.

Oil Phase Preparation:

7 L of light mineral oil (LMO) with 70 mL of span80 (1% v/v) was prepared. 5.7 L of the LMO+span80 mixture was added to a 6-L bioreactor vessel through a 0.2 µm filter and stirred with a 70-mm impeller rod at 800 rpm.

PEG Intracrosslinker Solution Preparation:

an aqueous solution containing 10% w/v 4-arm poly (ethylene glycol) vinyl sulfone (PEG-VS) (20 kDa), 500 µM K-peptide (Ac-FKGGERCG-NH2), 500 µM Q-peptide (Ac-NQEQVSPLGGERCG-NH2) and 1 mM RGD (Ac-RGD-SPGERCG-NH2) was prepared in 300 mM triethanolamine (pH 7.75). The PEG solution was filtered using a 0.22 µm Stericup PES filter.

Peptide Intracrosslinker Solution Preparation:

an 8 mM di-cysteine MMP-sensitive peptide (Ac-GCRDGPQGIWGQDRCG-NH2) aqueous solution was prepared. The crosslinker solution was filtered using a 0.22 µm Stericup PES filter.

Water-in-Oil (w/o) Emulsion:

150 mL of the PEG solution was mixed 1:1 to 150 mL of the crosslinker solution. Immediately after mixing, the aqueous mixture (300 mL, 5% v/v w/o) was injected using a peristaltic pump (135 mL/min) to the stirring oil phase. After 2 h of stirring, the particles were allowed to settle down overnight and accumulated at the bottom of the reaction vessel. Because the particles are denser that LMO, they settled and accumulated at the bottom of the 6-L reaction vessel.

Approximately 80% (~4.8 L) of the oil phase was removed using a peristaltic pump and dip tubes of the vessel.

The particles were redispersed in 4.8 L of 95% isopropanol/5% water (referred to as 95% IPA solution) and stirred for at least 5 min at 450 rpm.

The particles were harvested in a 50 L sterile bag: at the same rate liquid is removed from the 6-L vessel, 95% IPA solution was added to the vessel to keep the volume constant (6 L) during particle harvest until 50 L of 95% IPA solution has been transferred through the 6-L vessel into the harvest bag.

Example 2. Purification of Flowable Microgel Particles

Tangential flow filtration was used to purify and concentrate flowable microgel particles produced as described in Example 1.

The membrane used in this system was a Spectrum hollow fiber mPES membrane (P/N N02-E65U-07-N, pore rating=0.65 µm, lumen ID=0.75 mm, surface area 1,800 $cm^2$).

The TFF system was gamma irradiated for sterilization.

The TFF system was plumbed to a lab stand with a Master Flex pump installed onto the retentate loop (see FIG. 8). Spectrum Labs luer lock pressure transducers were placed on the filter inlet, outlet, and permeate in order to monitor the flows. The 50-L bag containing the harvested microparticles dispersed in 95% IPA solution was connected to the TFF inlet manifold.

The particles were transferred from the bag into the TFF reservoir (V=3.5 L) and circulated through the retentate loop at 5 L/min (permeate valve close).

The particles were slowly concentrated (permeate valve open): the volume in the reservoir (3.5 L) was kept constant by pumping in microparticles as volume is removed through the permeate. The permeate flow was adjusted to target a filtrate flux rate between 200 and 300 LMH.

A gradient of solvents (from 95% isopropanol to 100% water and finally buffer) was used to purify the particles. All the solvents and buffers were stored in a sterile bag. A constant volume diafiltration was performed with 20 L of each of the following solutions: 95% IPA solution, 50% IPA solution, 100% pure water, and final formulation buffer (10 mM phosphate buffer+100 mM NaCl+5 µM Eosin Y, pH 7.4). The permeate flow was adjusted to target a filtrate flux rate between 200 and 300 LMH.

The particles were concentrated by TFF until the material reached the targeted concentration.

The particles were harvested in sterile bags and eventually concentrated further by centrifugation if necessary.

Example 3. Wound Healing in Pigs Using Microporous Gel Systems

Figure 10A:
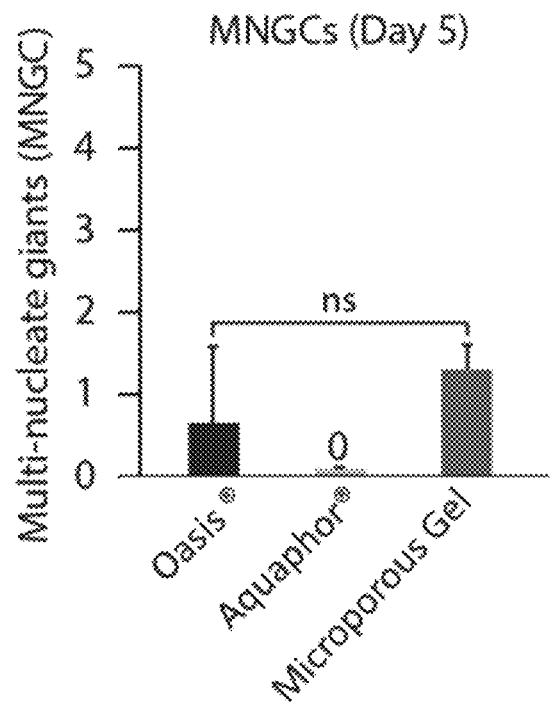
FIG. 10A-10C shows characterization of wounds in pigs treated with a flowable microgel particle system disclosed herein five days after treatment.
Figure 10B:
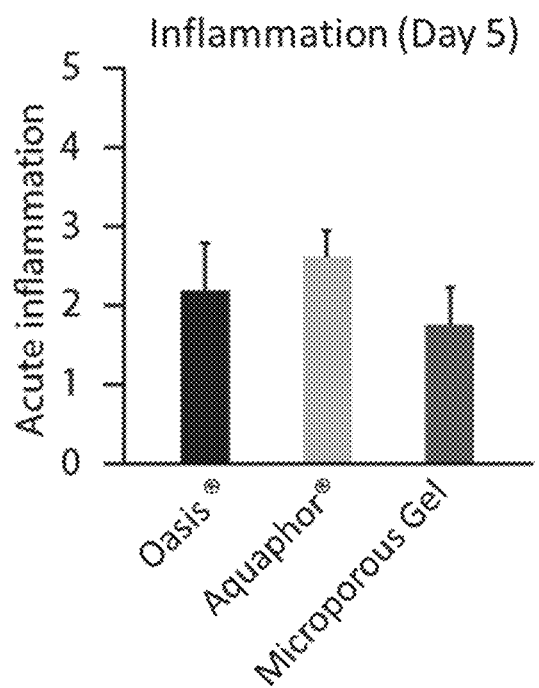
Figure 10C:
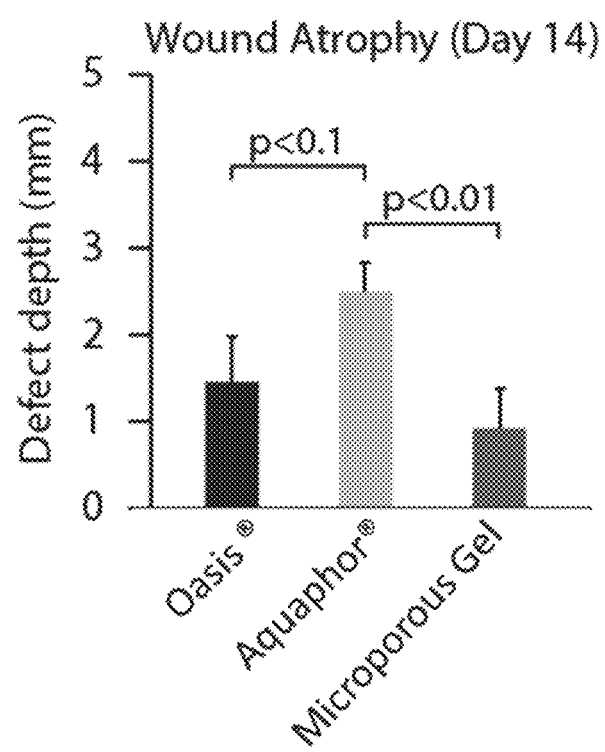

Wound beds in pigs were completely filled by a microporous gel that stabilized into a microporous scaffold. The microporous gel was produced as described in Example 1. Briefly, the microporous gel was made of the backbone polymer 4-ARM-PEG-VS+MMP-degradable peptide+RGD+K+Q peptides in final formulation buffer (PBS+5 uM Eosin Y). The gel was annealed by light with eosin Y as an annealing agent. As controls, pigs with similar defects were treated with an Oasis® SIS matrix and Aquaphor®. Crosssections of the wounds were examined after five days. Granulation tissue was stimulated in all test cases, as measured by tissue staining (data not shown, but available). Oasis® SIS matrix and the microporous gel show similar, low acute multinucleated giant cell (MNGC) formation (while Aquaphor® shows none), see FIG. 10A. Acute inflammation was reduced in the wound beds receiving the microporous gel when compared to Oasis® SIS matrix to Aquaphor®, see FIG. 10B. After 14 days of healing, wound atrophy was reduced by both the Oasis® SIS matrix and the microporous scaffold, see FIG. 10C. Cross-section histology showed the wound beds were completely filled by all the microporous gel 5 days after treating, while defects remain for both the Oasis® SIS matrix and the Aquaphor® treated wounds.

Figure 11A:
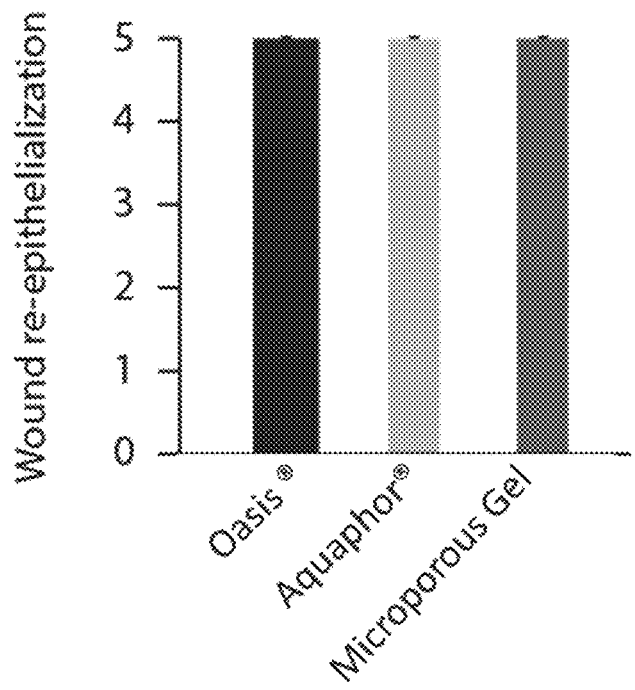
FIG. 11A-11B shows characterization of wounds in pigs treated with a flowable microgel particle system disclosed herein fourteen days after treatment.
Figure 11B:
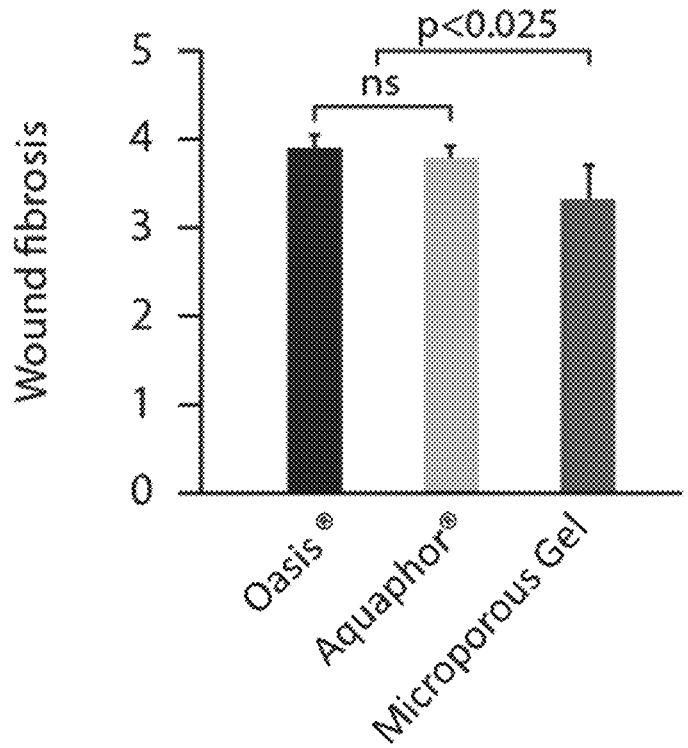

Wound re-epithelialization and tissue fibrosis were examined in tissue after 14 days of healing. Complete re-epithelialization was seen for all wounds treated with Oasis® SIS matrix, Aquaphor®, or the microporous gel, see FIG. 11A. When examining the reformed tissue after 14 days, pathologic scoring indicated that tissue replacing the microporous scaffold exhibited less alignment in the collagen fiber bundles, and less dense bundling, indicative of tissue architecture different than that of fibrous scar tissue, as compared to the other cohorts (Oasis® SIS matrix, Aquaphor®). Quantification of fibrosis scoring is presented in FIG. 11B.

Figure 12A:
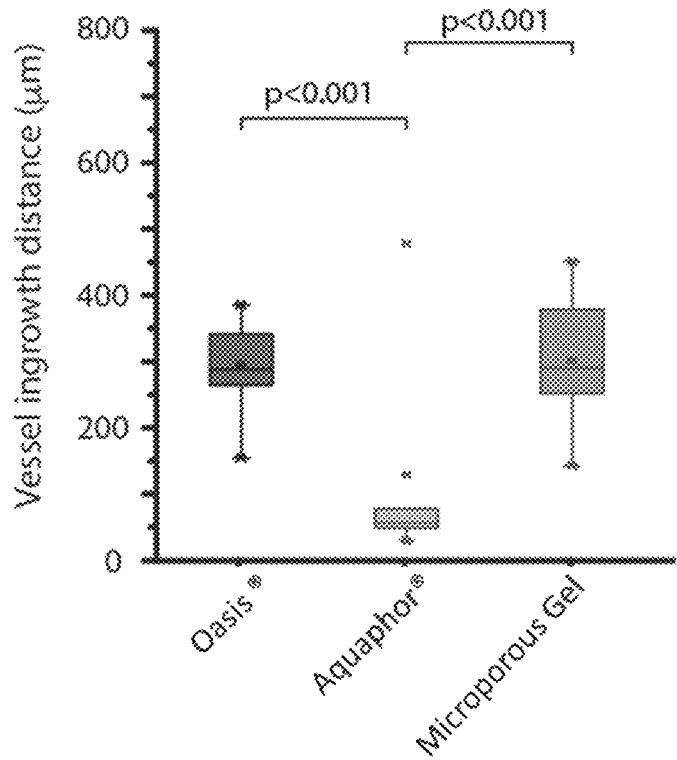
FIG. 12A-12C shows augmentation of wound healing vascularization with a flowable microgel particle system disclosed herein five days after treatment.
Figure 12B:
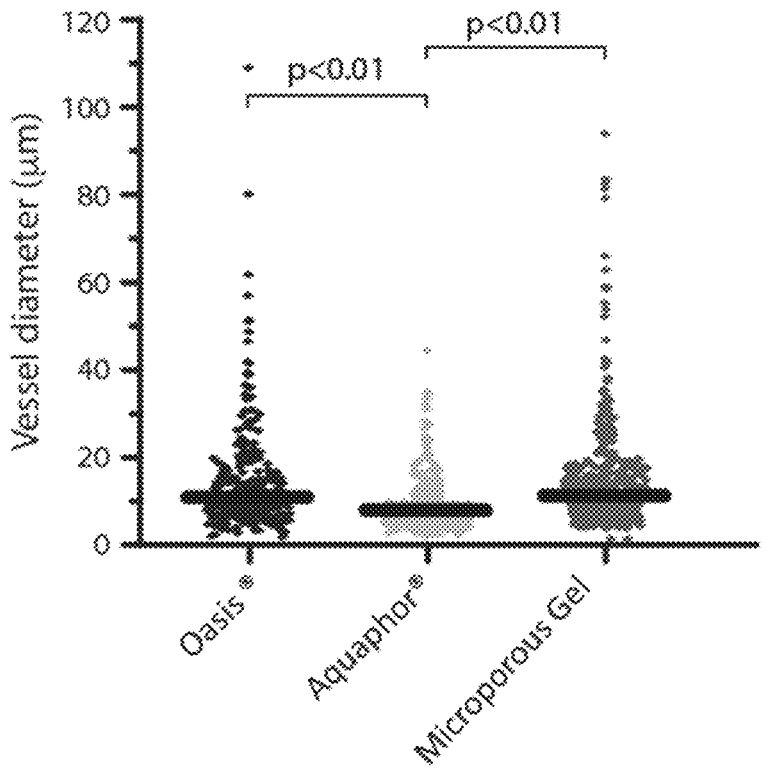
Figure 12C:
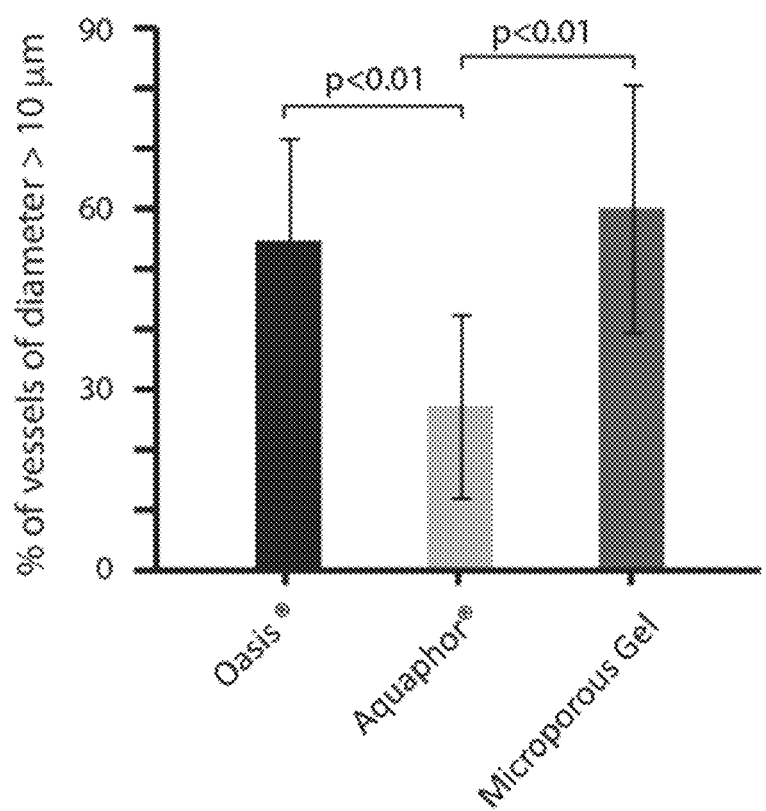

Augmentation of wound healing vascularization by the MAP gel was observed. Measurements of vessel ingrowth 5 days after healing showed that both Oasis® SIS matrix and the microporous scaffold promoted increased depth of vascular penetration into the wound site (or scaffold), compared to Aquaphor® standard care, (data not shown, but available). Vessel ingrowth quantification shows statistically significant augmentation of vascularization by Oasis® SIS matrix and the microporous scaffold, see FIG. 12A. High magnification images showed ingrowing vessels in the Oasis® SIS matrix and microporous scaffold cohorts, (data not shown, but available). Both the Oasis® SIS matrix and microporous scaffold microporous scaffold led to larger caliber vessel formation in healed tissue after 14 days, compared to Aquaphor® treatment, (data not shown, but available). Aquaphor® forms typical scar-like small vessels, averaging 5-10 μm in diameter (~capillary size). Both Oasis® SIS matrix and the microporous scaffold promote larger vessel formation, see FIG. 12B, and while these tissues also contain capillaries, the percentage of vessels larger than 10 μm in diameter significantly increases compared to Aquaphor® treated wounds. See FIG. 12C.

Both microporous gel injections and bilateral non-porous hydrogel injections (chemically identical but no microporous structure) were collected after 38 days in vivo and qualitatively assessed for tissue integration. The non-porous flowable hydrogel (Oasis® SIS matrix) exhibited virtually no tissue ingrowth, with consistent MNGCs surrounding the material edge, typical of the Foreign Body Response. Microporous gel injections showed no detectable inflammation or MNGC presence around the injection periphery, almost complete tissue integration, and significant material degradation. The presence of large vessels with intimal walls, and web-like dermal tissue indicated non-fibrous tissue formation de novo within the injection site (data not shown, but available).

Example 4. Administration of a Microporous Gel to a Site of a Cardiac Pacemaker

A physician performs surgery on a patient to place a pacemaker in the chest of the patient. The physician inserts the pacemaker in the left shoulder area where an incision is made below the collar bone creating a small pocket where the pacemaker battery pack and part of the leads are actually housed in the patient's body. The lead is fed into the heart through a large vein. Either: (i) After the pacemaker is inserted, a solution containing microgel particles and an annealing agent are applied to the incision site or (ii) a solution containing microgel particles and an annealing agent are applied to the incision site, followed by inserting the pacemaker. In either condition (i) or (ii), the solution flows around the pacemaker and fills any void between the pacemaker and surrounding tissue. The solution also contains an antibiotic, an analgesic, an anti-inflammatory agent and an anti-fibrotic agent. The surgical site is exposed to light and the microgel particles anneal to form a microporous scaffold. Alternatively, heteroannealing takes place, and light is unnecessary. The surgical site is sewn up. The patient heals quickly, experiences little pain or discomfort, and does not develop any infection at the surgical site. Eight years later, the physician creates another incision in the chest to replace the battery in the pacemaker. The physician notices that the pacemaker is integrated with the surrounding tissue better than a pacemaker in a patient that does not receive the microporous gel system. The physician also notices that there is less scar tissue around the pacemaker relative to a pacemaker in a patient that does not receive the microporous gel system. It is easier for the physician to remove or replace the pacemaker battery pack or leads, and the surgery time is reduced for this procedure—reducing the risk of infection during the procedure.

Example 5. Spinal Cord Stimulation Implant for Spastic Cerebral Palsy

A surgical implant of electrodes for lateral cord stimulation is employed in patients with spastic cerebral palsy with the aim to improve tonus, motor function and speech. A unilateral hemilaminectomy is performed at C3-C4 level, starting from 4th cervical spinous process. A multicontact electrode is placed on the lateral surface of the spinal cord. The multicontact electrode is connected to a subcutaneously implanted pulse generator (IPG). In order to implant the IPG, a surgical void is created in the torsos of each patient. The IPG is placed within the surgical void. However, there is remaining space in the surgical void that is not filled by the IPG. A solution containing microgel particles and an annealing agent are applied to the incision site. The solution flows around the IPG and fills any void between the IPG and surrounding tissue. Less solution is used in patients where there is less remaining space as compared to more solution used in patients where there is more remaining space. In this way, the microporous gel system adapts the same device (e.g., size, shape) to all patients. Alternatively, a solution containing microgel particles and an annealing agent are applied to the incision site prior to the placement of the IPG, and excess microgel particles are easily removed after IPG placement. The solution also contains an antibiotic, an analgesic, an anti-inflammatory agent and an anti-fibrotic agent. The surgical site is exposed to light and the microgel particles anneal to form a microporous scaffold. Alternatively, heteroannealing takes place, and light is unnecessary. The surgical site is sewn up. A post-operative evaluation is performed every 30 days for the next six months. The patients heal quickly, experience little pain or discomfort, and do not develop any infection at the surgical site. The devices work well, improving tonus, motor function and speech. If the device requires any re-intervention, the physician is able to access the device more easily than a patient that did not receive the microporous system, reducing surgical times and risks associated with that surgery.

Example 6. Cardioverter-Defibrillator Implant for Heart Arrhythmia

A cardioverter-defibrillator is implanted under the skin in the left upper chest of a patient with a ventricular arrhythmia. Either: (i) After the cardioverter-defibrillator is inserted, a solution containing microgel particles and an annealing agent are applied to the incision site or (ii) a solution containing microgel particles and an annealing agent are applied to the incision site, followed by inserting the cardioverter-defibrillator. In either condition (i) or (ii), the solution flows around the cardioverter-defibrillator and fills any void between the cardioverter-defibrillator and surrounding tissue. Risk of a venous obstruction such as upper extremity deep venous thrombosis and pulmonary embolism is historically high in patients receiving these devices. Thus, the solution contains an antithrombotic agent. The surgical site is exposed to light and the microgel particles anneal to form a microporous scaffold. Alternatively, heteroannealing takes place, and light is unnecessary. The surgical site is sewn up. The antithrombotic agent is released from the microporous scaffold over the next few weeks as the patient recovers. The patient does not develop or experience a vascular occlusion.

Example 7. Testing Shelf-Life Stability of a Microporous Gel System

The shelf life and stability of the microporous scaffold is tested and validated using real-time and elevated temperature methods. Shelf life at 25° C., 50° C., and 100° C. are determined by exposing the scaffold to these temperatures followed by undergoing the annealing process and measuring the increase in compressive modulus of the scaffold after annealing (compared to material that has not been exposed to elevated temperature and has been freshly prepared (no time passing since manufacture and measurement). Analytical methods (such as HPLC/DAD to measure peptide and light absorbing chemical components and GPC to measure polymeric chemical components) are also used to quantitate the shelf-life stability of the scaffold. After real-time and elevated temperature treatments, the scaffold is rinsed in aqueous buffer to extract degraded components, and that buffer is tested using the analytical methods to detect degradation products. Elevated temperatures (100° C.) can be used to accelerate the stability process, where stability over short times at 100° C. indicate stability over longer times at 25° C.

What is claimed is:

1. A method comprising:
    a) providing a membrane filtration system comprising a solid support with pores, each pore having a diameter of at most 9 micrometers (μm);
    b) transferring dispersed microgel particles from a first continuous phase to a final continuous phase by controlled addition of an intermediate continuous phase to the first continuous phase, wherein the final continuous phase is immiscible with the first continuous phase;
    c) maintaining a single miscible continuous phase containing the dispersed microgel particles;
    d) applying the single miscible continuous phase containing the dispersed microgel particles to a membrane of the membrane filtration system; and
    e) removing an impurity from the dispersed microgel particles or the single miscible continuous phase using size exclusion filtration by the membrane filtration system, thereby producing purified microgel particles.

2. The method of claim 1, wherein transferring of step (b), the maintaining of step (c), the applying of step (d), and the removing of step (e) occur substantially simultaneously.

3. The method of claim 1, wherein maintaining the single miscible phase is required for the membrane filtration system to remove the impurity from the dispersed microgel particles.

4. The method of claim 1, wherein applying the single miscible phase to the membrane comprises applying the single miscible phase in a direction that is tangential to the membrane.

5. The method of claim 1, wherein the membrane filtration system is selected from tangential flow filtration (TFF), ultrafiltration-diafiltration (UFDF), microfiltration-diafiltration (MFDF), or hollow-fiber-diafiltration (HFDF).

6. The method of claim 1, wherein the first continuous phase comprises a solvent that is a non-polar oil.

7. The method of claim 1, wherein the intermediate continuous phase comprises a solvent that is an alcohol solution.

8. The method of claim 1, wherein the impurity is a surfactant.

9. The method of 1, wherein the purified microgel particles comprise a backbone polymer and annealing components.

10. The method of claim 9, further comprising producing a stabilized scaffold by introducing an annealing agent to the purified microgel particles, the annealing agent linking the annealing components of the purified microgel particles together to form the stabilized scaffold, the stabilized scaffold comprising pores having a median diameter of about 10 μm to about 35 μm.

11. The method of claim 10, wherein between or about 10-40% of a total volume of the stabilized scaffold is made up of the pores.

12. The method of claim 9, wherein annealing components each comprise, independently, a functional group selected from the group consisting of a vinyl sulfone, thiol, amine, imidazole, aldehyde, ketone, hydroxyl, azide, alkyne, vinyl, alkene, maleimide, carboxyl, N-hydroxysuccinimide (NETS) ester, isocyanate, isothiocyanate, hydroxylamine, and thione.

13. The method of claim 9, wherein the annealing components each comprise, independently a reactive moiety selected from the group consisting of a catechol, a sialic acid, a boronic acid, a molecular cage, adamantane, biotin, and streptavidin.

14. The method of claim 10, wherein linking comprises a reaction selected from the group consisting of Michael addition, amide bond coupling, Diels-Alder cycloaddition, Huisgen 1,3-dipolar cycloaddition, reductive amination, carbamate linkage, ester linkage, thioether linkage, disulfide bonding, hydrazone bonding, oxime coupling, and thiourea coupling.

15. The method of claim 10, wherein linking the annealing components is performed by forming a covalent bond between at least two of the annealing components.

16. The method of claim 10, wherein the annealing components comprise a first annealing component and a second annealing component, and wherein the first annealing component and the second annealing component are not the same.

17. The method of claim 16, wherein there is at least 1% more of the second annealing component than the first annealing component in the stabilized scaffold.

18. The method of claim 16, wherein a concentration of the first annealing component and a concentration of the second annealing component in the stabilized scaffold are not the same.

19. The method of claim 10, wherein producing a stabilized scaffold is performed in vivo, at a site of an implanted medical device.

20. The method of claim 1, wherein the final continuous phase comprises a solvent that is water.

* * * * *